United States Patent
Kawamura et al.

(10) Patent No.: US 6,541,129 B1
(45) Date of Patent: Apr. 1, 2003

(54) ORGANIC ELECTROLUMINESCENCE DEVICE AND PHENYLENEDIAMINE DERIVATIVE

(75) Inventors: Hisayuki Kawamura, Sodegaura (JP); Chishio Hosokawa, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 09/530,597

(22) PCT Filed: Sep. 3, 1999

(86) PCT No.: PCT/JP99/04794

§ 371 (c)(1),
(2), (4) Date: May 9, 2000

(87) PCT Pub. No.: WO00/14174

PCT Pub. Date: Mar. 16, 2000

(30) Foreign Application Priority Data

Sep. 9, 1998 (JP) .......................... 10-255563
Feb. 24, 1999 (JP) .......................... 11-047110

(51) Int. Cl.[7] .................. H05B 33/14; C07C 211/54

(52) U.S. Cl. .................. 428/690; 428/917; 428/704; 313/504; 313/506; 257/40; 257/103; 564/307; 564/308; 564/427; 564/428; 564/429; 564/433

(58) Field of Search .................. 428/690, 917, 428/704; 313/504, 506; 257/40, 103; 564/307, 308, 427, 428, 433, 429

(56) References Cited

U.S. PATENT DOCUMENTS

| | | | | |
|---|---|---|---|---|
| 5,536,949 A | * | 7/1996 | Hosokawa et al. | 257/40 |
| 6,259,203 B1 | * | 7/2001 | Kawamura et al. | 313/506 |
| 6,344,283 B1 | * | 2/2002 | Inoue et al. | 428/690 |
| 6,406,804 B1 | * | 6/2002 | Higashi et al. | 428/690 |
| 6,437,373 B1 | * | 8/2002 | Sakai et al. | 257/103 |

FOREIGN PATENT DOCUMENTS

| | | | |
|---|---|---|---|
| EP | 0 891 121 A1 | | 1/1999 |
| JP | 62267749 | * | 11/1987 |
| JP | 394262 | * | 4/1991 |
| JP | 820771 | * | 1/1996 |
| JP | Wo-9622273 | * | 7/1996 |
| JP | 8-259934 | * | 10/1996 |
| JP | 9301934 | * | 11/1997 |
| JP | Wo-9830071 | * | 7/1998 |
| JP | 11054280 A | * | 2/1999 |
| JP | 11167992 | * | 6/1999 |

OTHER PUBLICATIONS

U.S. patent application Ser. No. 09/121,831, filed Jul. 24, 1998, pending.
U.S. patent application Ser. No. 09/424,870, filed Dec. 9, 1999, pending.
U.S. patent application Ser. No. 09/446,905, filed Jan. 3, 2000, pending.
U.S. patent application Ser. No. 09/530,597, filed May 9, 2000, pending.

* cited by examiner

*Primary Examiner*—Deborah Jones
*Assistant Examiner*—Ling Xu
(74) *Attorney, Agent, or Firm*—Oblon, Spivak, McClelland, Maier & Neustadt, P.C.

(57) ABSTRACT

The invention is to provide an organic EL device having a long life time that can reduce the driving voltage of the organic EL device, and to provide a material having a small ionization potential and exhibiting a large hole mobility by using as a layer or a zone. The organic electroluminescence device comprises a pair of electrodes and an organic light emitting layer sandwiched in the electrodes, characterized in that a hole transporting zone provided between the electrodes comprises the phenylenediamine derivative represented by the specific structural formulae, and the phenylenediamine derivative has a hole mobility of $10^{-4}$ cm$^2$/V·s or more upon using as a layer or a zone, with the organic light emitting layer containing a charge injection auxiliary.

8 Claims, 1 Drawing Sheet

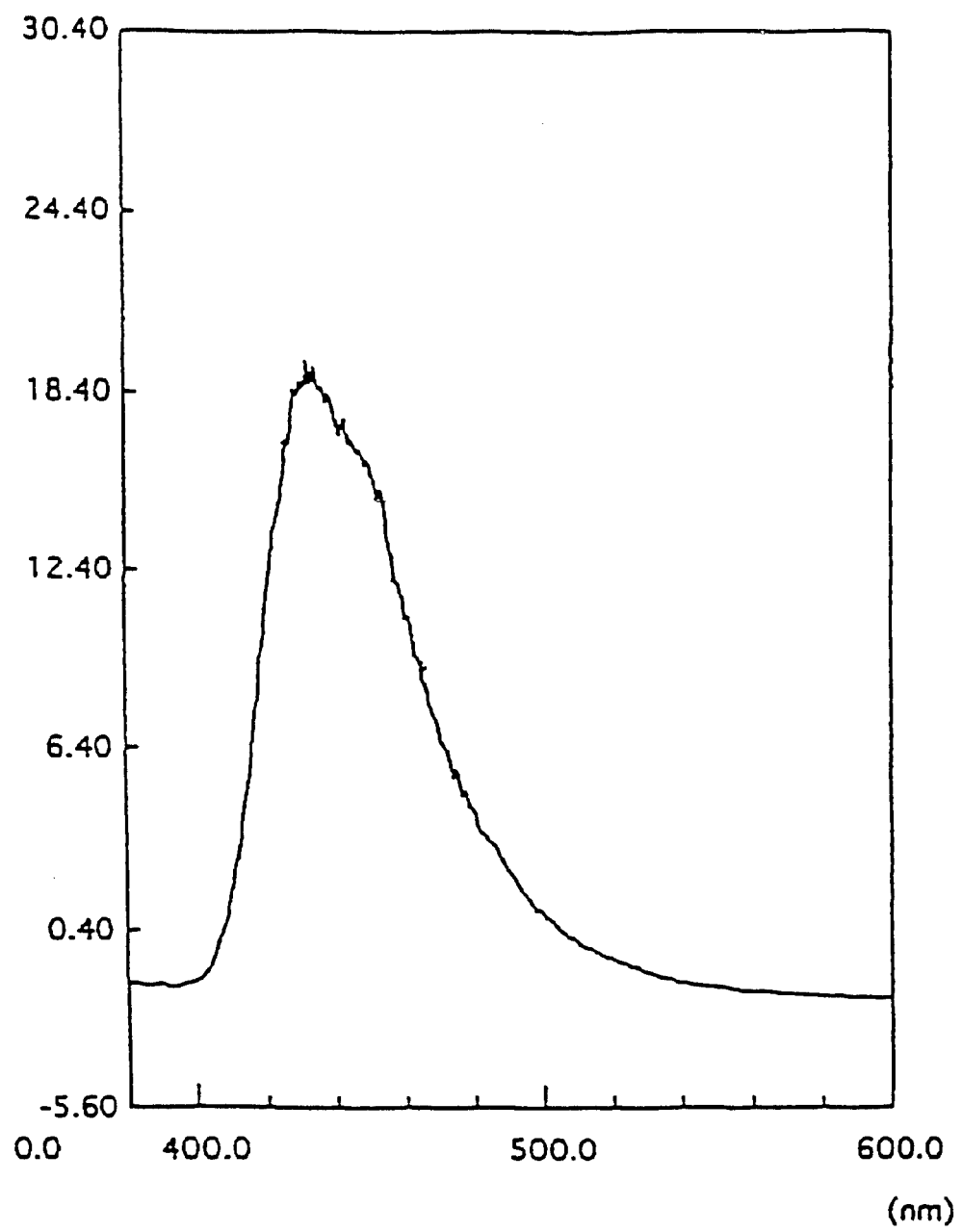

ORGANIC ELECTROLUMINESCENCE DEVICE AND PHENYLENEDIAMINE DERIVATIVE

TECHNICAL FIELD

The present invention relates to an organic electroluminescence device (hereinafter, referred to as organic EL device) and a phenylenediamine derivative, and more particularly, an organic EL device comprising a pair of electrodes and an organic light emitting layer sandwiched in the electrodes, and a phenylenediamine derivative used as a material for the organic EL device and the like.

BACKGROUND ART

An organic EL device is being earnestly studied since it is a complete solid state device and can form a display and an illumination of light-weight and thin-form that is driven at a low voltage.

A problem on applying the organic EL device to a display is to make the driving voltage being a lower voltage. For example, by using a dendrimer of an aromatic amine disclosed in JP-A-4-308688 as a hole injection material, the driving voltage is lowered. The compound has a small ionization potential of 5.2 eV owing to the phenylenediamine skeleton, and exhibits an effect of lowering the driving voltage.

However, the compound having a phenylenediamine skeleton has a small hole mobility of $3\times10^{-5}$ cm$^2$/V·s, and therefore the driving voltage in the region of high electric current injection is insufficiently lowered.

A high molecular weight aromatic amine compound disclosed in JP-A-9-301934 has a small ionization potential of 5.2 eV but has a problem in that the hole mobility is insufficient. It is expected that the hole mobility be lowered due to the mixing of impurities.

That is, in the fluorescent spectrum of the compound disclosed in JP-A-9-301934 (FIG. 1), alight emission component having a maximum fluorescent wavelength peak of 500 nm or higher is observed, which is not present originally. This shows that impurities are mixed. Furthermore, the voltage is increased by 2.7 V with only driving time of 76 hours, which becomes a hindrance of lowering the driving voltage. Accordingly, in the device disclosed in the publication, the hole mobility is lowered and the driving voltage is increased by the impurities.

Furthermore, because it has a green fluorescent component, when the compound is used in the hole transporting zone of a blue light emitting device, blue light emission cannot be obtained due to mixing of green light emission component.

International Patent Publication WO98/30071 (published on Jul. 9, 1998) discloses an organic electroluminescence device using a compound similar to the present invention, but fails to disclose an effect in that a particular low voltage can be obtained on combining with a light emitting layer containing a charge injection auxiliary.

DISCLOSURE OF THE INVENTION

An object of the invention is to provide an organic EL device having a long life time that can decrease the driving voltage of the organic EL device.

Another object of the invention is to provide a material having a small ionization potential and exhibits a large hole mobility when it is used as a layer or a zone.

The invention is an organic electroluminescence device comprising a pair of electrodes and an organic light emitting layer sandwiched in the electrodes, characterized in that a hole transporting zone provided between the electrodes comprises a phenylenediamine derivative represented by the general formula (I), the general formula (II) or the general formula (II)', the phenylenediamine derivative exhibits a hole mobility of at least $10^{-4}$ cm$^2$/V·s on using as a layer or a zone, and the organic light emitting layer contains a charge injection auxiliary.

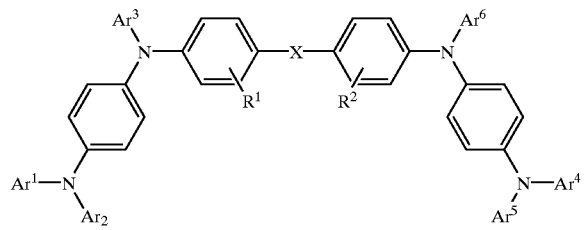

General formula (I)

($Ar^1$ to $Ar^6$ represent an aryl group having from 6 to 24 nucleus carbon atoms, which may be substituted with a hydrogen atom, an alkyl or an alkoxy group having from 1 to 6 carbon atom(s), an aryl group having from 6 to 24 nucleus carbon atoms, or a styryl group. X represents a linking group, which is a single bond, arylene having from 6 to 24 nucleus carbon atoms, alkylene having from 1 to 6 carbon atom(s), diphenylmethylene, an ether bond, a thioether bond, a substituted or unsubstituted vinyl bond, or an aromatic heterocyclic ring. $R^1$ and $R^2$ represent an alkyl group having from 1 to 6 carbon atom(s), an alkoxy group, or a hydrogen atom, which may be bonded to each other to form a substituted or unsubstituted saturated 5-membered ring or a saturated 6-membered ring.)

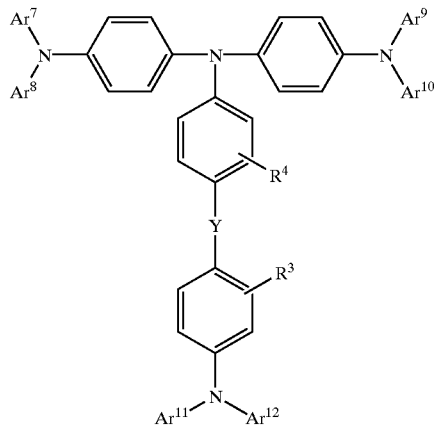

General formula (II)

($Ar^7$ to $Ar_{12}$ represent an aryl group having from 6 to 24 nucleus carbon atoms, which may be substituted with hydrogen atoms, an alkyl or an alkoxy group having from 1 to 6 carbon atom(s), an aryl group having from 6 to 24 nucleus carbon atoms, or a styryl group. Y represents a linking group, which is a single bond, arylene having from 6 to 24 nucleus carbon atoms, alkylene having from 1 to 6 carbon atom(s), diphenylmethylene, an ether bond, a thioether bond, an aromatic heterocyclic ring, or a substituted or unsubstituted vinyl bond. $R^3$ and $R^4$ represent an alkyl group having from 1 to 6 carbon atoms, an alkoxy group, or a hydrogen atom, which may be bonded to each other to form a substituted or unsubstituted saturated 5-membered ring or a saturated 6-membered ring.)

General formula (II′)

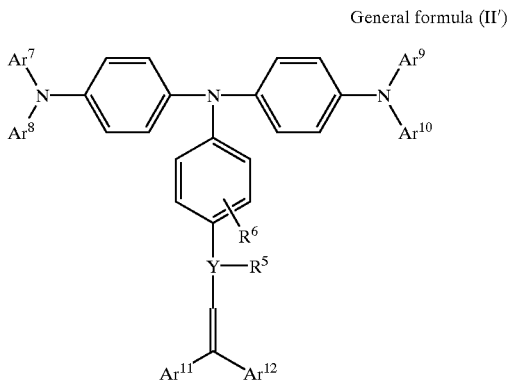

($Ar^7$ to $Ar^{12}$ represent an aryl group having from 6 to 24 nucleus carbon atoms, which may be substituted with a hydrogen atom, an alkyl or an alkoxy group having from 1 to 6 carbon atom(s), an aryl group having from 6 to 24 nucleus carbon atoms, or a styryl group. Y represents a linking group, which is a single bond, arylene having from 6 to 24 nucleus carbon atoms, alkylene having from 1 to 6 carbon atom(s), diphenylmethylene, an ether bond, a thioether bond, an aromatic heterocyclic ring, or a substituted or unsubstituted vinyl bond. $R^5$ and $R^6$ represent an alkyl group having from 1 to 6 carbon atom(s), an alkoxy group, or a hydrogen atom, which may be bonded to each other to form a substituted or unsubstituted saturated 5-membered ring or a saturated 6-membered ring.)

The hole transporting zone herein means a region of the organic EL device that has a function of transporting a hole from an anode. The function of transporting a hole is that it has a hole mobility of $10^{-4}$ cm$^2$/V·s or more under an electric field of from $10^4$ to $10^6$ V/cm. Specific examples of the hole transporting zone include a hole injecting layer, a hole transporting layer and the like, and a light emitting layer may be included in some cases.

In the invention, the compound represented by the general formulae (I), (II) and (II)′ has a phenylenediamine skeleton and has a small ionization potential, and furthermore an excellent hole mobility can be ensured by the central skeleton shown by X and Y. In the invention, because the phenylenediamine derivative suitable as a hole injecting and transporting material is contained in the hole transporting zone, the driving voltage of the organic EL device can be decreased, and the increase of the driving voltage due to continuous driving can be suppressed.

Furthermore, in the invention, a light emitting layer containing a charge injection auxiliary is necessarily used.

The charge injection auxiliary herein means a compound having an ionization energy that is smaller than-the ionization energy of the main material forming the light emitting layer, and preferably a material assisting hole injection by adding in an amount of from 0.1 to 20 wt % into the light emitting layer. By the addition of the charge injection auxiliary, the organic EL device of the invention can lower the driving voltage and also can stabilize the driving voltage. The use of the phenylenediamine and the addition of the charge injection auxiliary into the light emitting layer bring about the effect that has not been obtained.

As the charge injection auxiliary, a compound, such as a styrylamine derivative, a distyrylarylene derivative, a tristyrylarylene derivative, a diamine derivative and the like, can be used, and particularly, a compound having an ionization energy of from 5.0 to 5.6 eV is preferred. The charge injection auxiliary may emit light in response to the recombination of a hole and an electron occurring in the light emitting layer, or may exhibit the effect of assisting charge injection without emission of light.

The hole transporting zone preferably has a hole injection layer containing the phenylenediamine derivative represented by the general formula (I), the general formula (II) or the general formula (II)′.

Alternatively, the hole transporting zone may have a hole transporting layer containing the phenylenediamine derivative represented by the general formula (I), the general formula (II) or the general formula (II)′.

In the foregoing, at least one of $Ar^1$ to $Ar^6$ in the general formula (I) is preferably a condensed aromatic ring having from 10 to 24 nucleus carbon atoms. According to this, the low voltage driving can be realized, and further the life time of the device can be prolonged.

On the other hand, the compound of the invention is a phenylenediamine derivative represented by the general formula (III).

General formula (III)

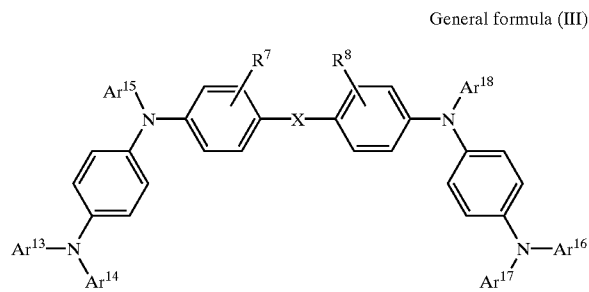

($Ar^{13}$ to $Ar^{18}$ represent an aryl group having from 6 to 24 nucleus carbon atoms, which may be substituted with a hydrogen atom, an alkyl or an alkoxy group having from 1 to 6 carbon atoms, an aryl group having from 6 to 24 nucleus carbon atoms, or a styryl group. X represents a linking group, which is a single bond, arylene having from 6 to 24 nucleus carbon atoms, alkylene having from 1 to 6 carbon atoms, diphenylmethylene, an ether bond, a thioether bond, a substituted or unsubstituted vinyl bond, or an aromatic heterocyclic ring. $R^7$ and $R^8$ represent an alkyl group having from 1 to 6 carbon atom(s), an alkoxy group, or a hydrogen atom, which may be bonded to each other to form a substituted or unsubstituted saturated 5-membered ring or a saturated 6-membered ring.)

Furthermore, the compound of the invention is a phenylenediamine derivative represented by the general formula (IV).

General formula (IV)

(Ar$^{19}$ to Ar$^{24}$ represent an aryl group having from 6 to 24 nucleus carbon atoms, which may be substituted with a hydrogen atom, an alkyl or an alkoxy group having from 1 to 6 carbon atom(s), an aryl group having from 6 to 24 nucleus carbon atoms, or a styryl group. Y represents a linking group, which is a single bond, arylene having from 6 to 24 nucleus carbon atoms, alkylene having from 1 to 6 carbon atom(s), diphenylmethylene, an ether bond, a thioether bond, an aromatic heterocyclic ring, or a substituted or unsubstituted vinyl bond. R$^9$ and R$^{10}$ represent an alkyl group having from 1 to 6 carbon atoms, an alkoxy group, or a hydrogen atom, which may be bonded to each other to form a substituted or unsubstituted saturated 5-membered ring or a saturated 6-membered ring.)

Alternatively, the compound of the invention is a phenylenediamine derivative represented by the general formula (V).

General formula (V)

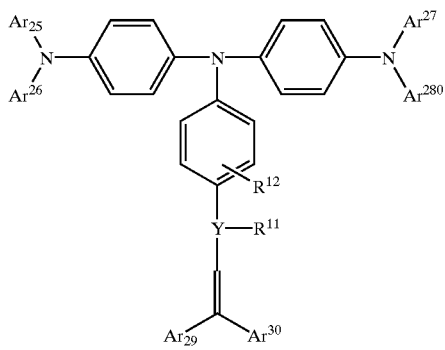

(Ar$^{25}$ to Ar$^{30}$ represent an aryl group having from 6 to 24 nucleus carbon atoms, which may be substituted with a hydrogen atom, an alkyl or an alkoxy group having from 1 to 6 carbon atom(s), an aryl group having from 6 to 24 nucleus carbon atoms, or a styryl group. Y represents a linking group, which is a single bond, arylene having from 6 to 24 nucleus carbon atoms, alkylene having from 1 to 6 carbon atom(s), diphenylmethylene, an ether bond, a thioether bond, an aromatic heterocyclic ring, or a substituted or unsubstituted vinyl bond. R$^{11}$ and R$^{12}$ represent an alkyl group having from 1 to 6 carbon atoms, an alkoxy group, or a hydrogen atom, which may be bonded to each other to form a substituted or unsubstituted saturated 5-membered ring or a saturated 6-membered ring.)

BRIEF DESCRIPTION OF THE DRAWING

FIG. 1 is a diagram showing a fluorescent spectrum of the phenylenediamine derivative of the invention, STBA-1.

BEST MODE FOR CARRYING OUT THE INVENTION

Embodiments of the invention will be described below.

(Organic EL Device)

(A) Phenylenediamine Derivative

The phenylenediamine derivative used in the organic EL device of the invention is a compound represented by the general formulae (I), (II) and (II)'.

In the general formulae (I), (II) and (II)', examples of the aryl group having from 6 to 24 nucleus carbon atoms include a phenyl group, a biphenyl group, a naphthyl group, an anthranyl group, a terphenyl group, a pyrenyl group and the like. In particular, a phenyl group and a naphthyl group are preferred.

Examples of the alkyl group having from 1 to 6 carbon atoms include methyl, ethyl, n-propyl, i-propyl, n-butyl, s-butyl, t-butyl, n-pentyl, n-hexyl and the like.

Examples of the alkoxy group having from 1 to 6 carbon atom(s) include methoxy, ethoxy, n-propyloxy, i-propyloxy, n-butoxy, s-butoxy, t-butoxy, n-pentyloxy, n-hexyloxy groups and the like.

Examples of the styryl group include 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl groups and the like. In particular, a 2,2-diphenylvinyl-1-yl group is preferred.

X in the general formula (I), Y in the general formula (II) and Y in the general formula (II)' each is a linking group, which is a single bond, arylene having from 6 to 24 nucleus carbon atoms, alkylene having from 1 to 6 carbon atom(s), diphenylmethylene, an ether bond, a thioether bond or an aromatic heterocyclic ring.

Examples of the arylene having from 6 to 24 nucleus carbon atoms include phenylene, biphenylene, naphtylene, anthranylene, terphenylene, pyrenylene and the like.

Examples of the alkylene having from 1 to 6 carbon atoms include methylene, isopropylene, cyclopropylene, cyclohexylene, cyclopentalene and the like.

The diphenylmethylene may be substituted with the alkyl having from 1 to 6 carbon atom(s) or an alkoxy group. Examples of the aromatic heterocyclic ring include pyrrole, furan, thiophene, schirole, triazine, oxadiazole, triazole, oxazole, quinoline, quinoxaline, pyrimidine and the like.

In the compound of the general formula (I), at least one of Ar$^1$ to Ar$^6$ preferably represents a condensed aromatic ring having from 10 to 24 nucleus carbon atoms or a phenyl group substituted with a styryl group. Examples of the condensed aromatic ring include naphthyl, anthranyl, pyrenyl, phenanthryl and the like, and in particular, a naphthyl group is preferred.

Examples of the styryl group include 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl groups and the like, and in particular, 2,2-diphenylvinyl-1-yl is preferred.

Because the compound of the invention is contained in the hole transporting zone of the device, it has a hole mobility of $10^{-4}$ cm$^2$/V·s or more under an electric field of from $10^4$ to $10^6$ V/cm.

Specific examples of the phenylenediamine derivative represented by the general formula (I) include the following compounds shown by (PD-01) to (PD-59) and (STBA-1). The invention is not limited to them.

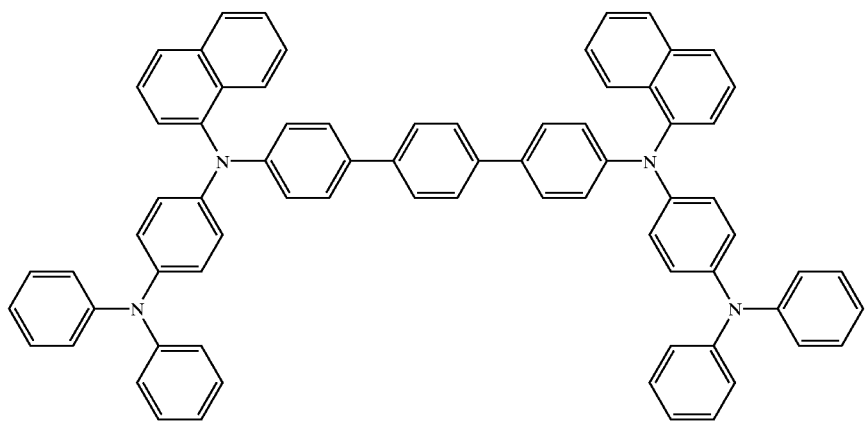
PD-01
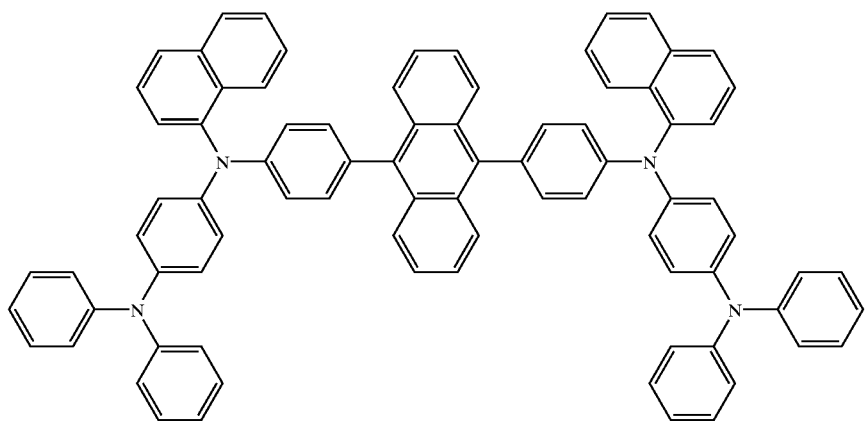
PD-02
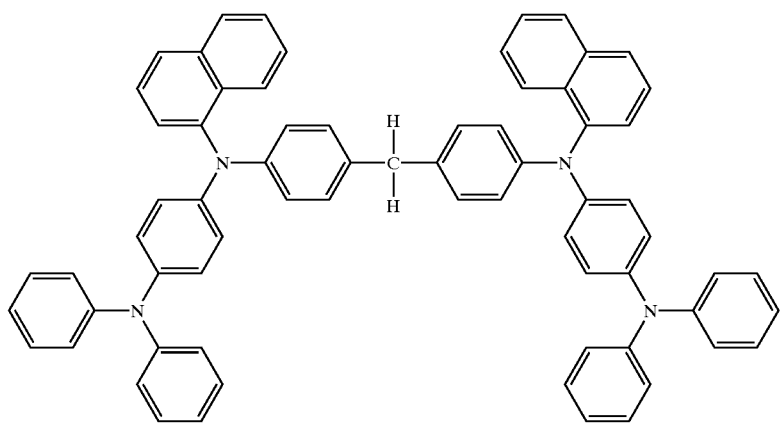
PD-03

-continued
PD-04
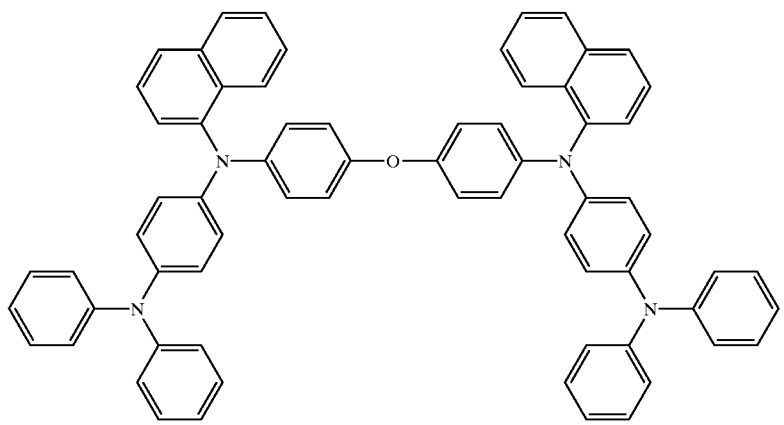
PD-05
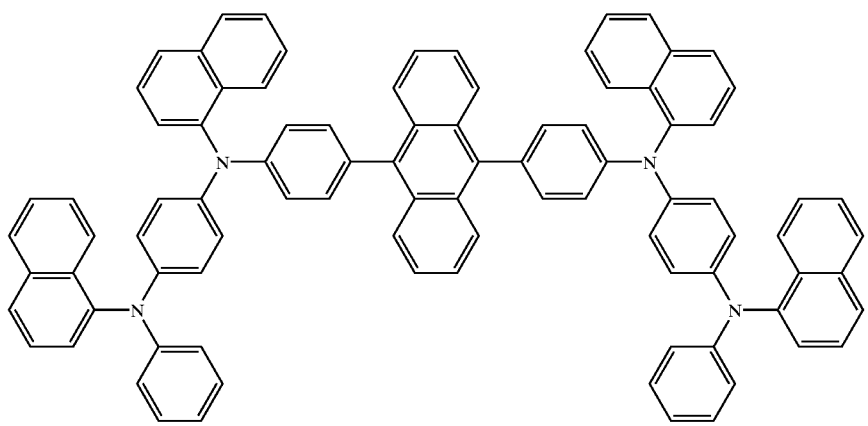
STBA-1
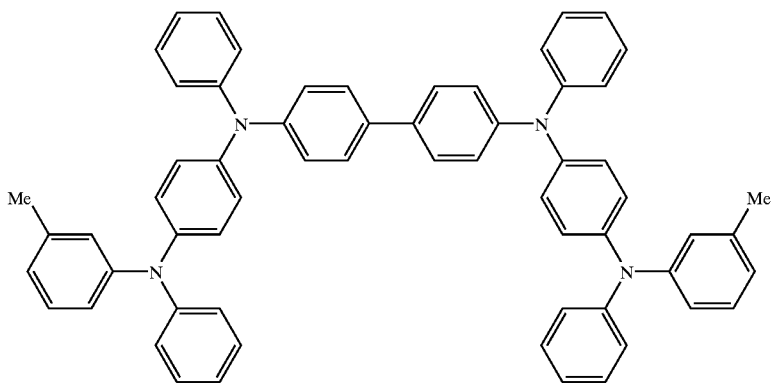
PD-06          PD-07
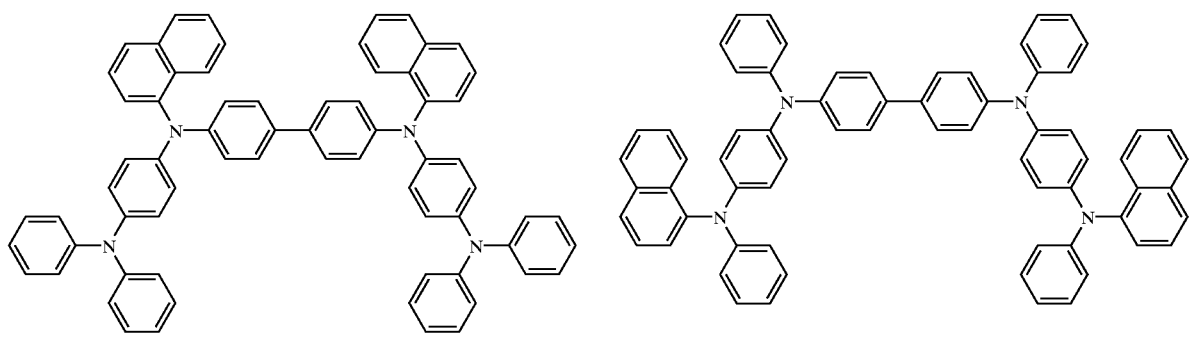

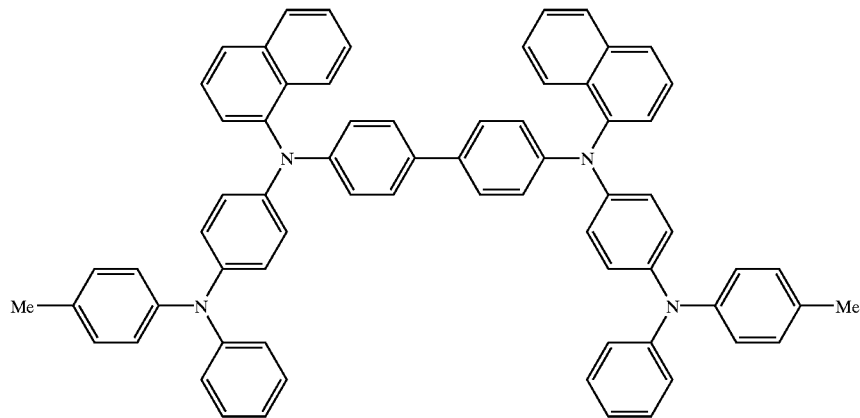
PD-08
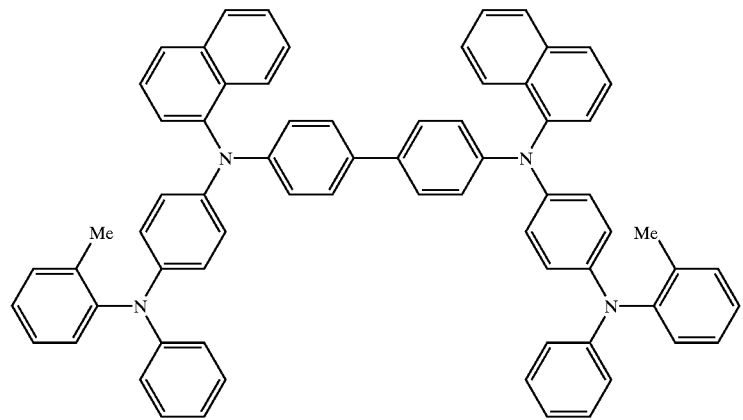
PD-09
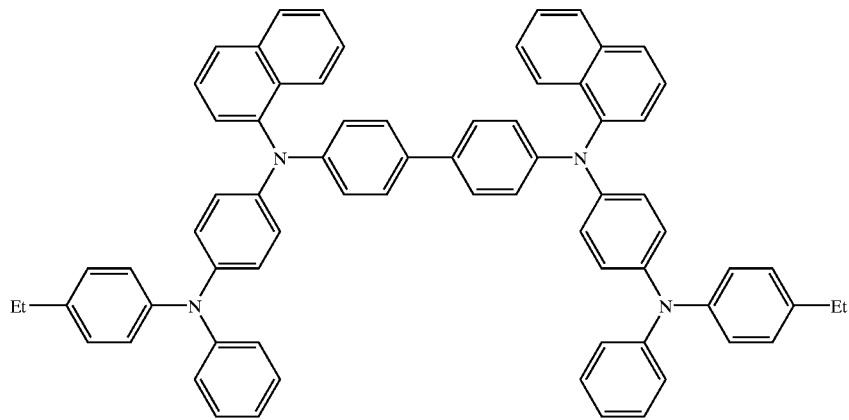
PD-10

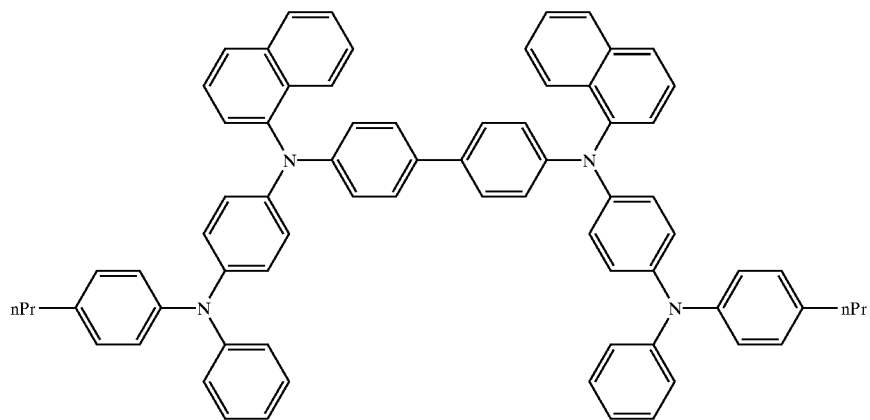
PD-11
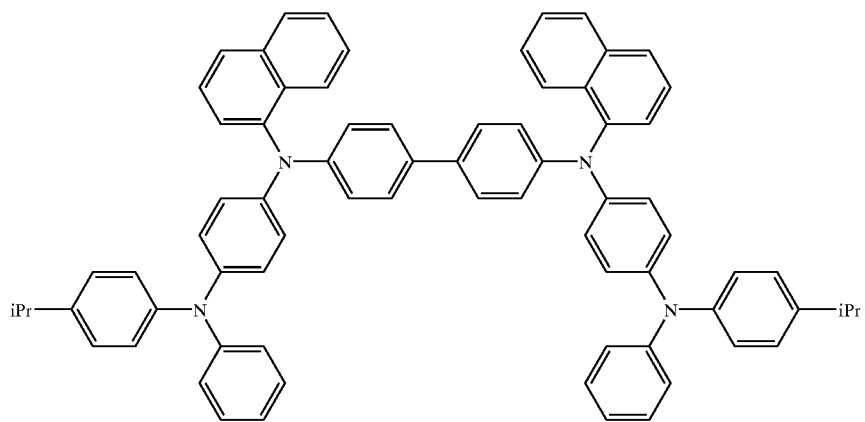
PD-12
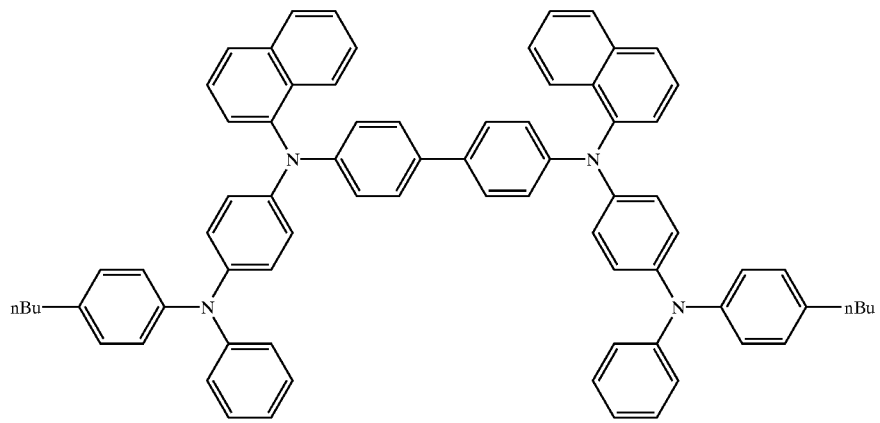
PD-13

-continued
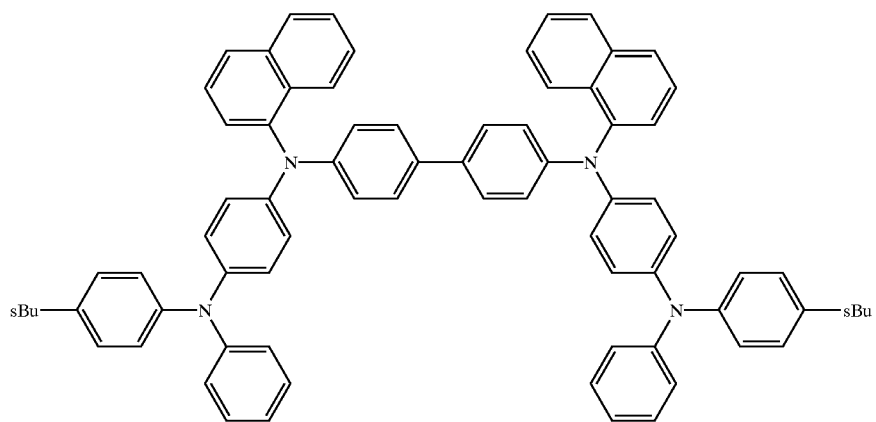
PD-14
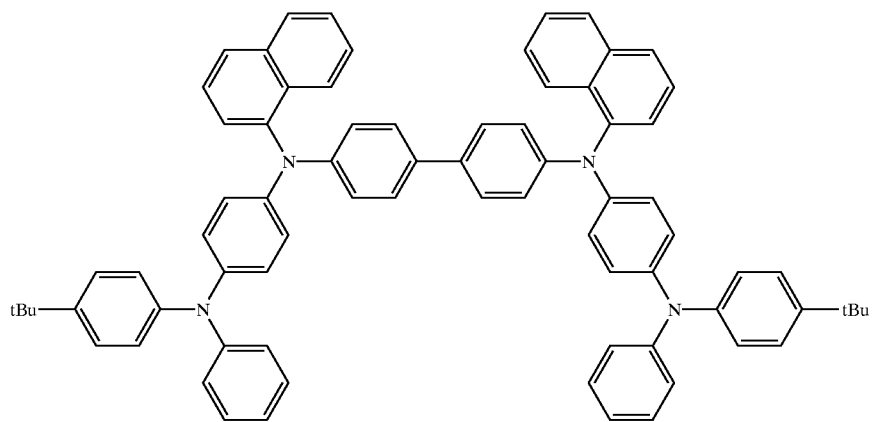
PD-15
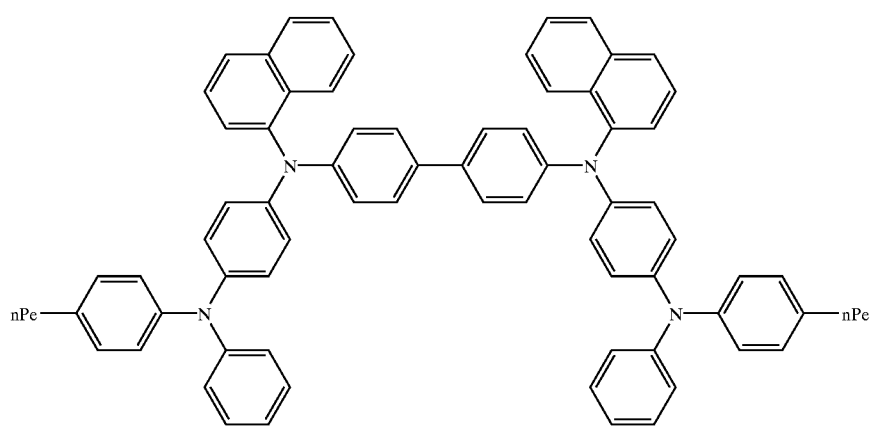
PD-16

-continued
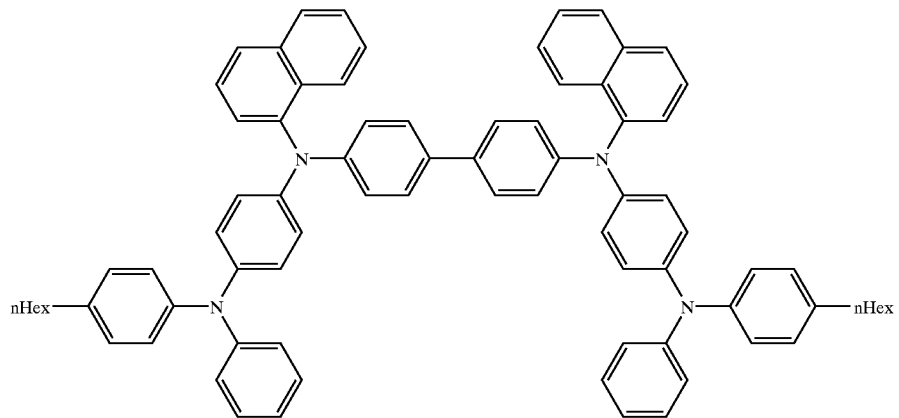
PD-17
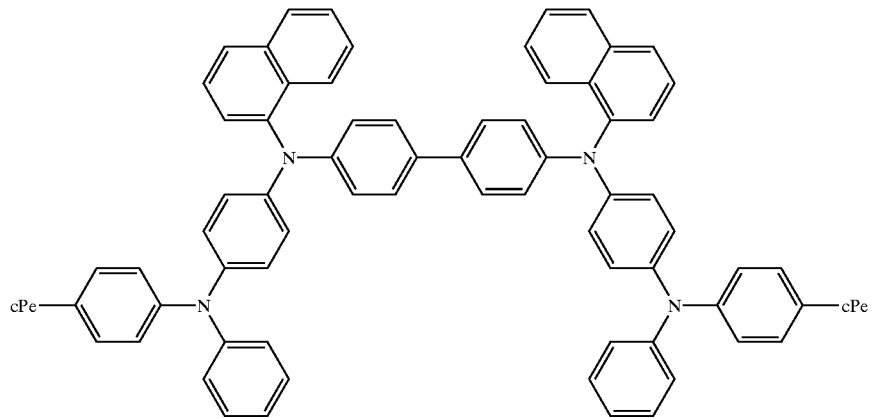
PD-18
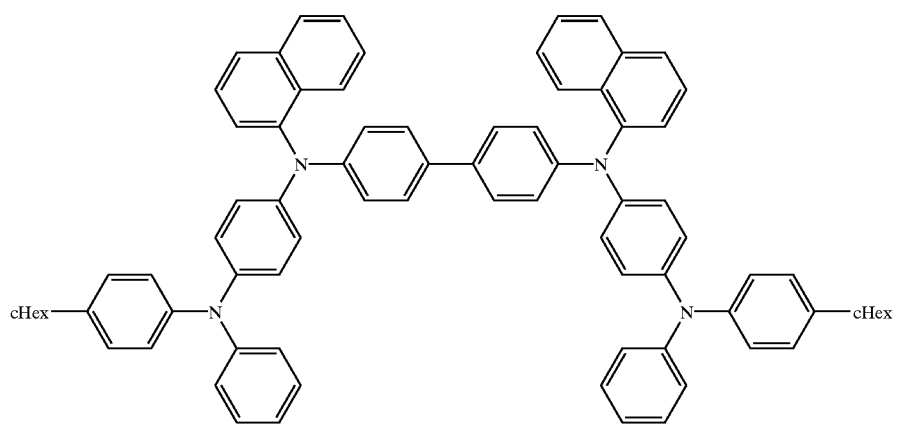
PD-19

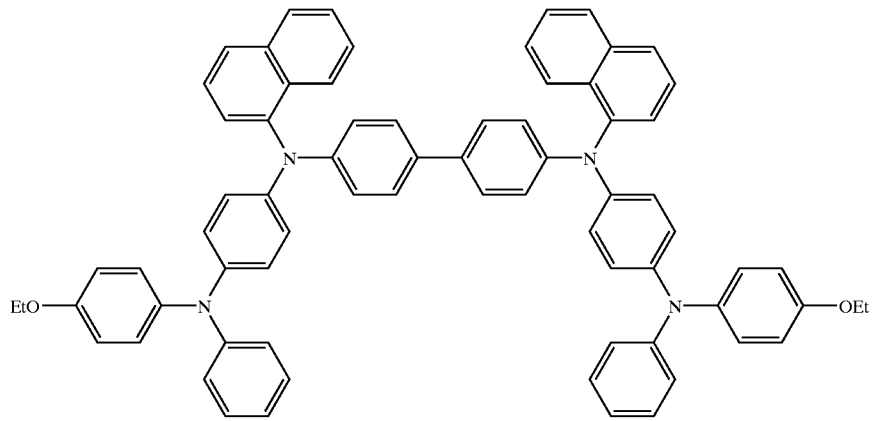
PD-20
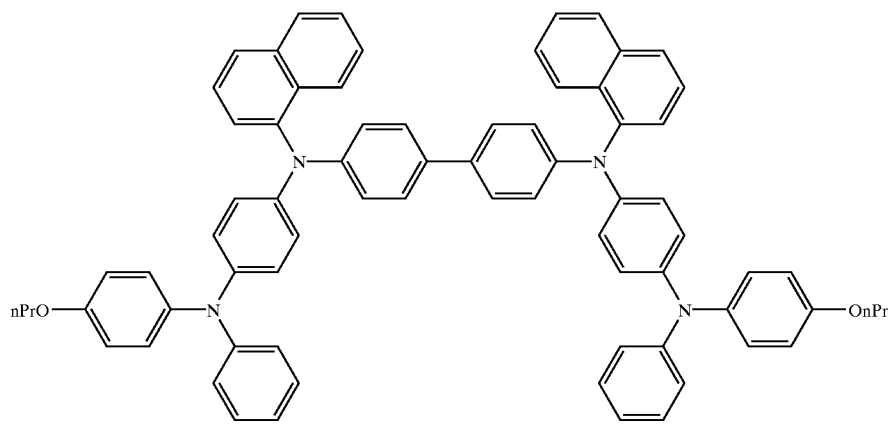
PD-21
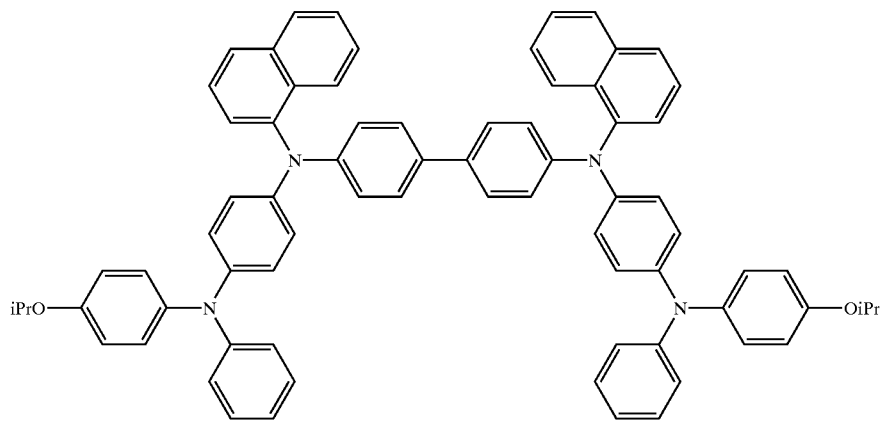
PD-22

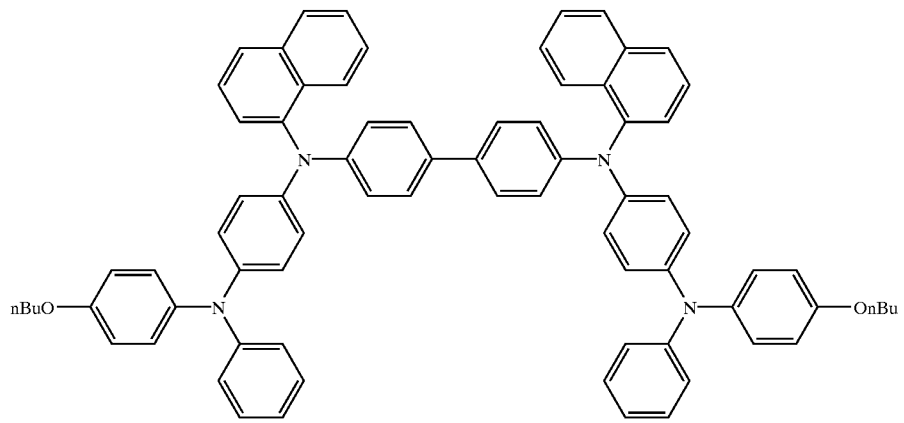
PD-23
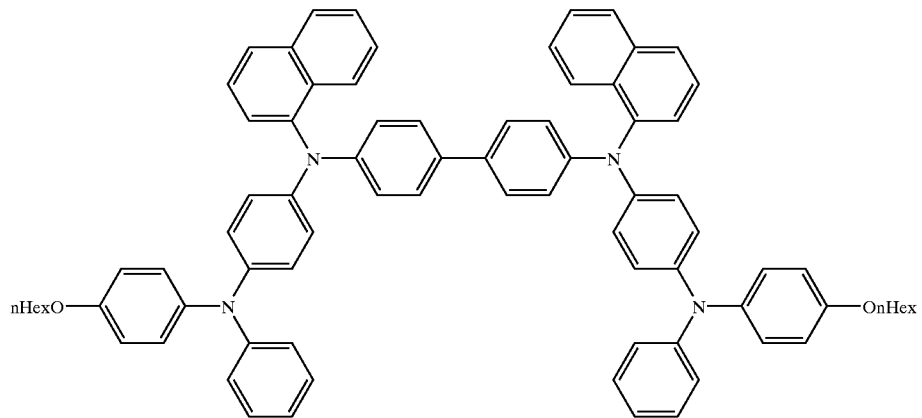
PD-27
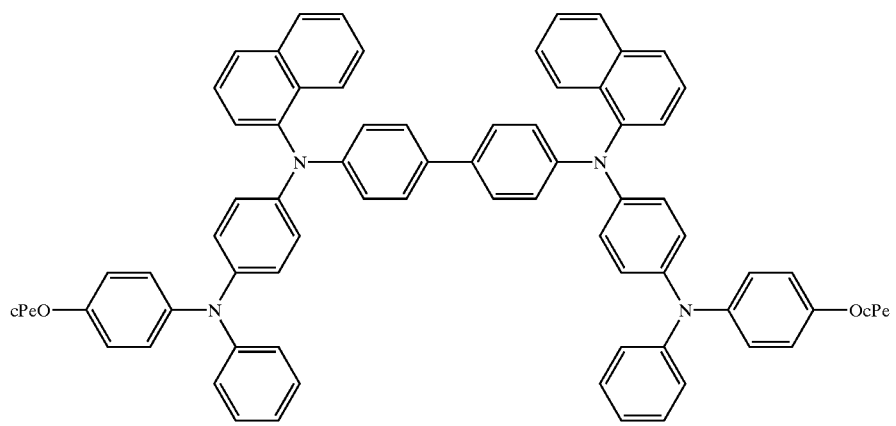
PD-28

-continued
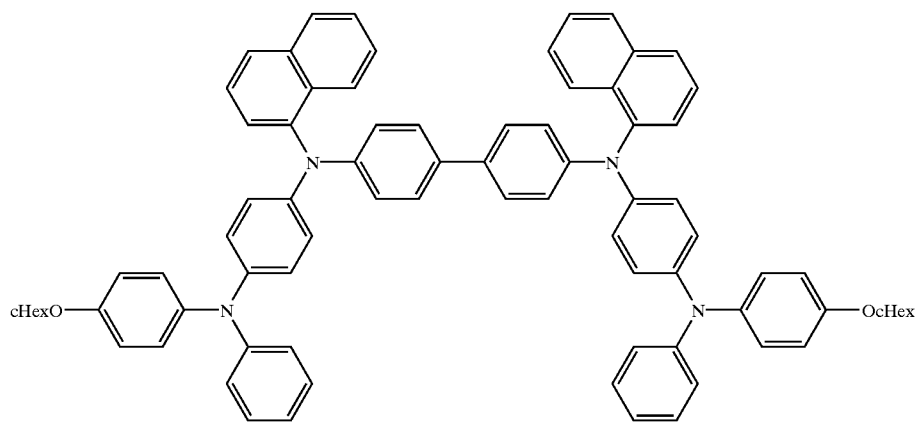
PD-29
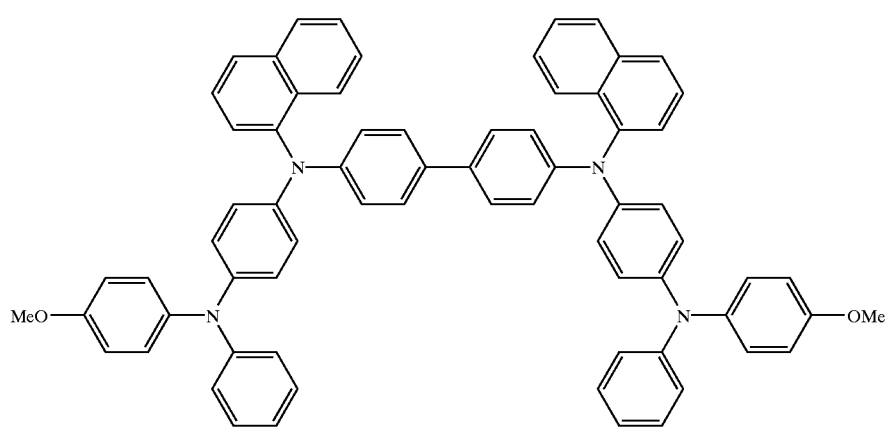
PD-30
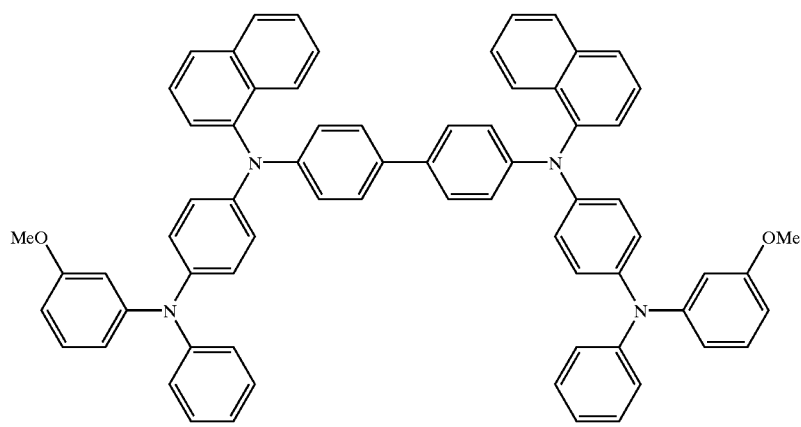
PD-31
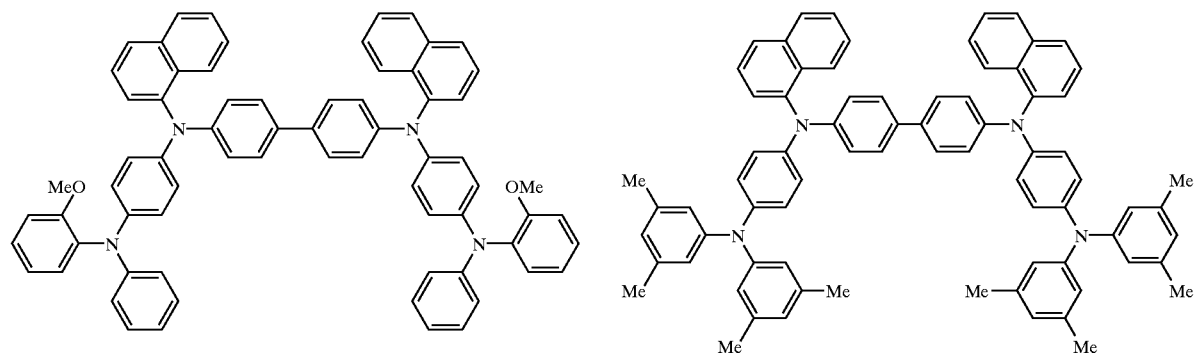
PD-32  PD-33

-continued
PD-34
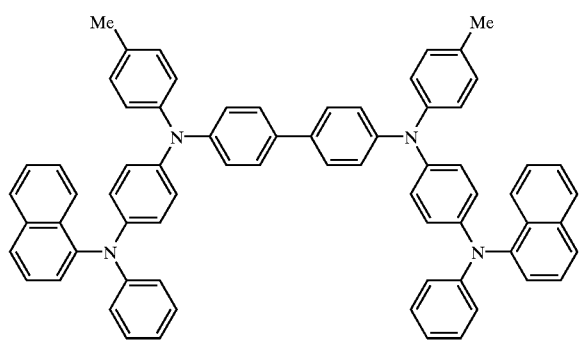
PD-35
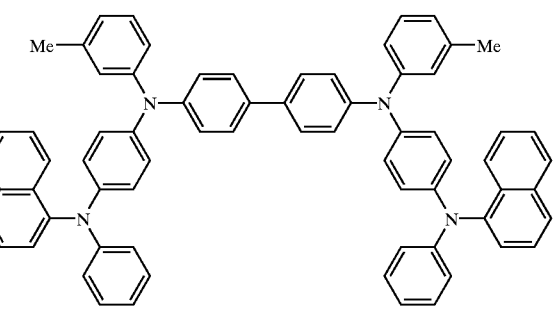
PD-36
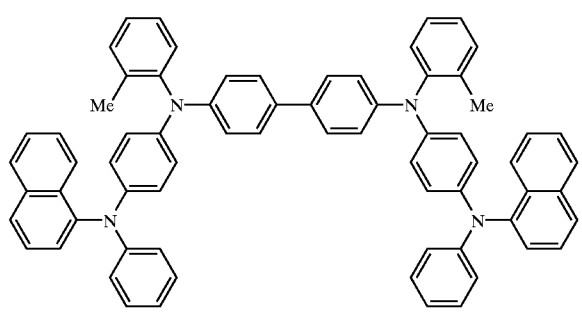
PD-37
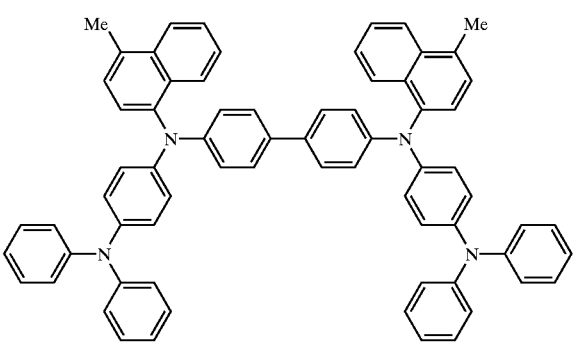
PD-38
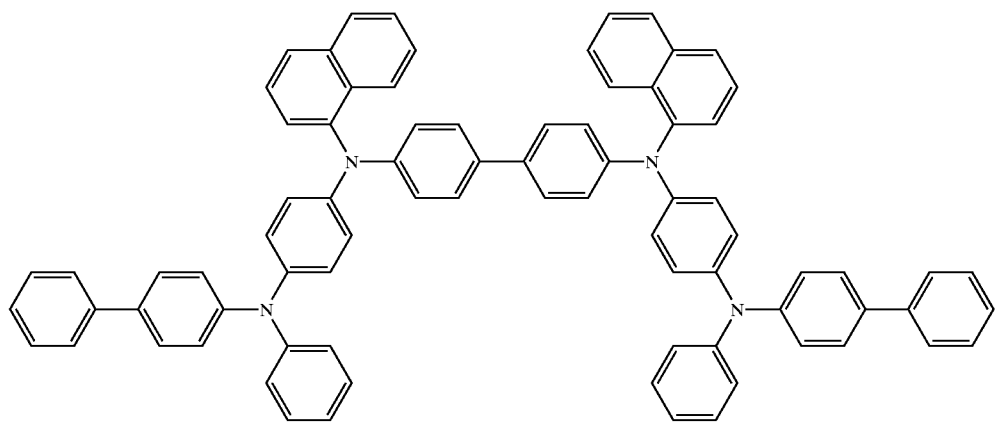
PD-39
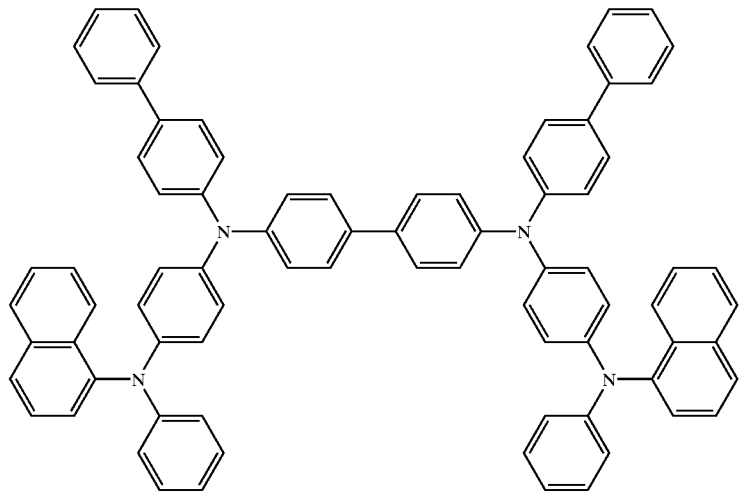

-continued
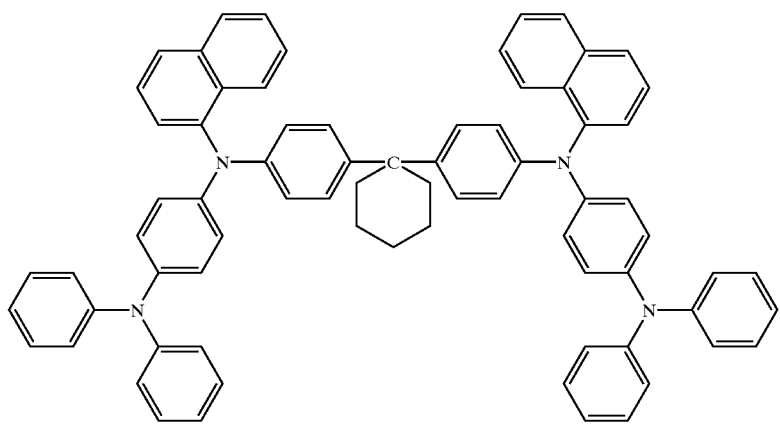
PD-40
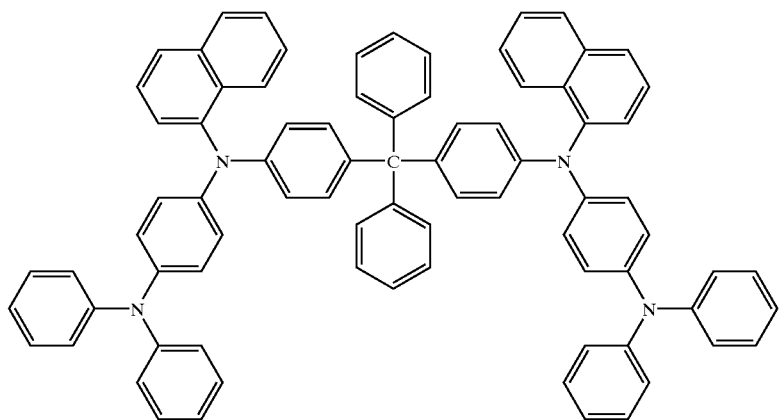
PD-41
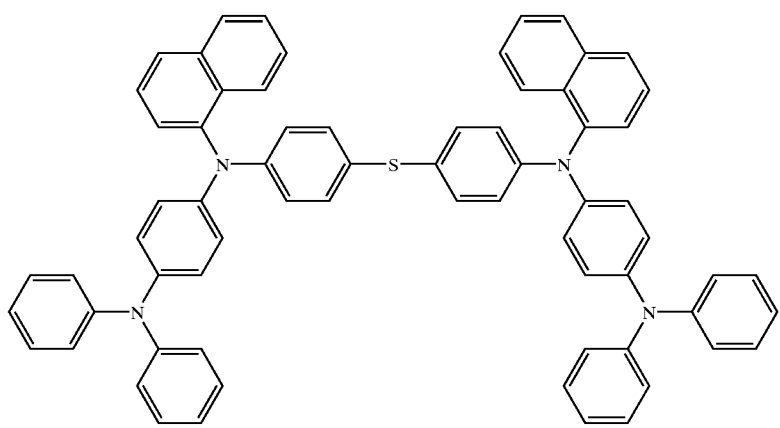
PD-42

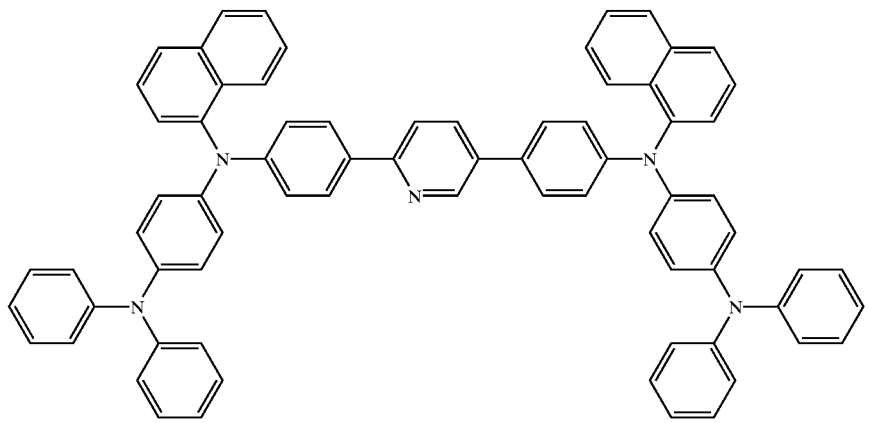
PD-43
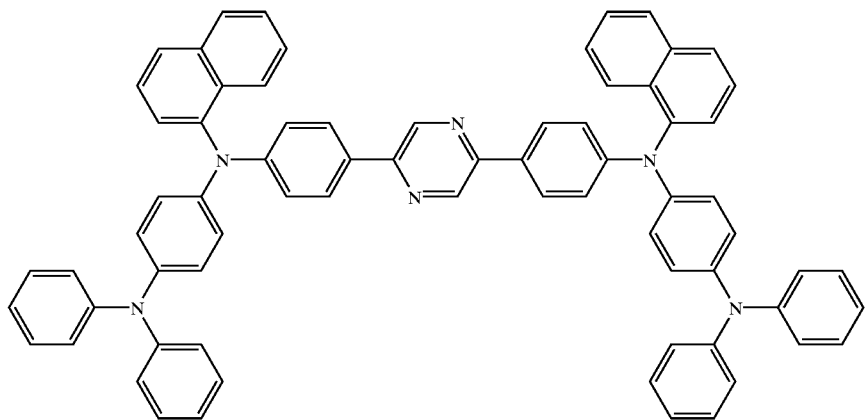
PD-44
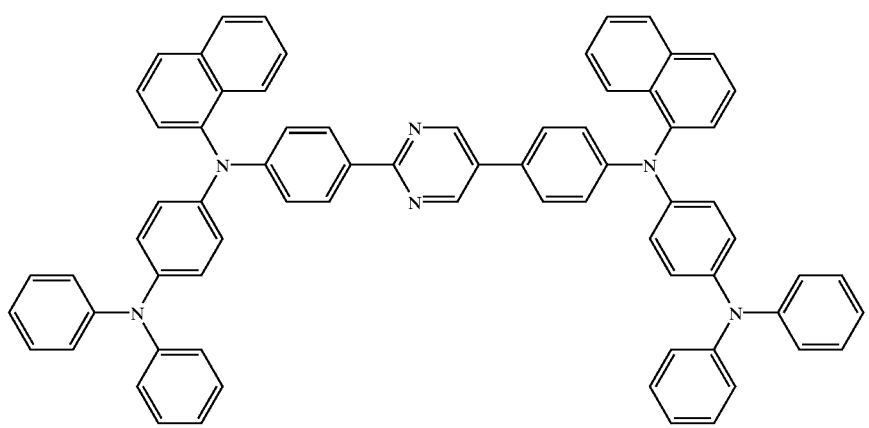
PD-45

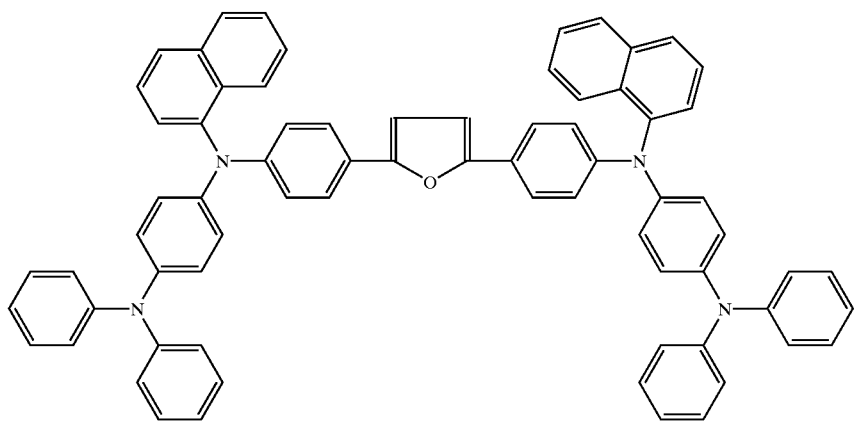
PD-46
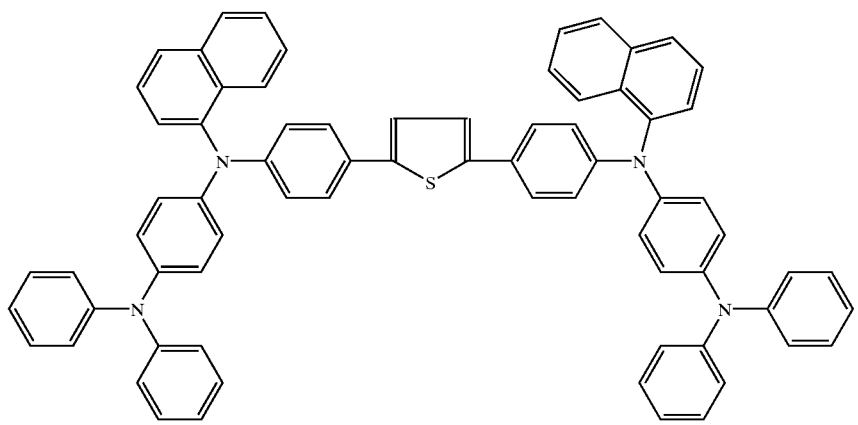
PD-47
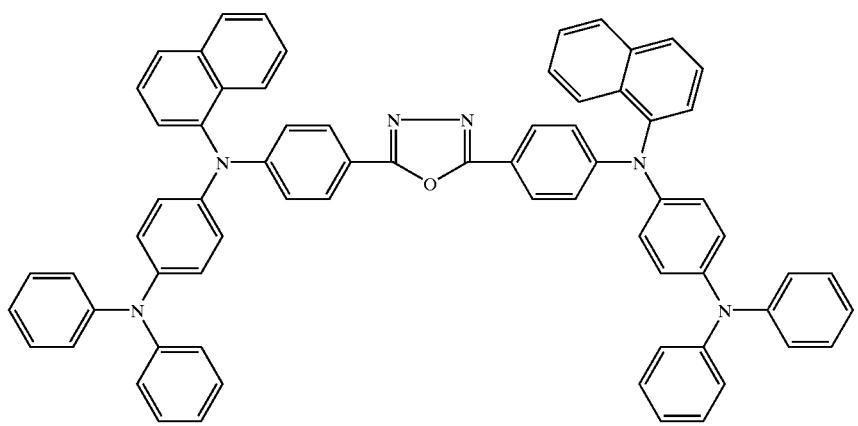
PD-48

-continued
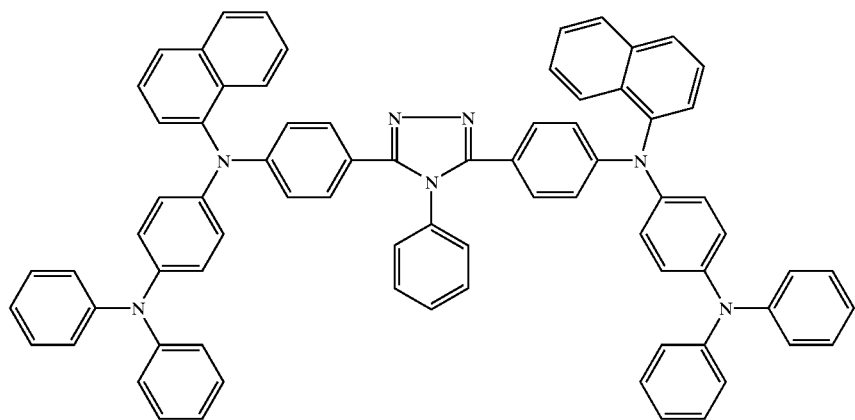
PD-49
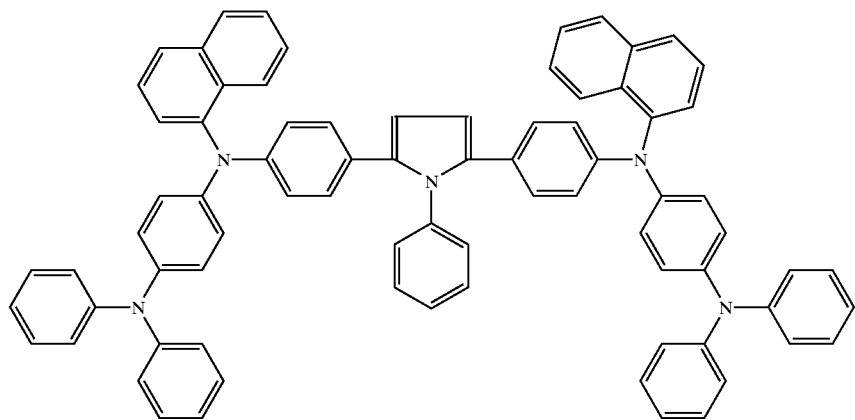
PD-50
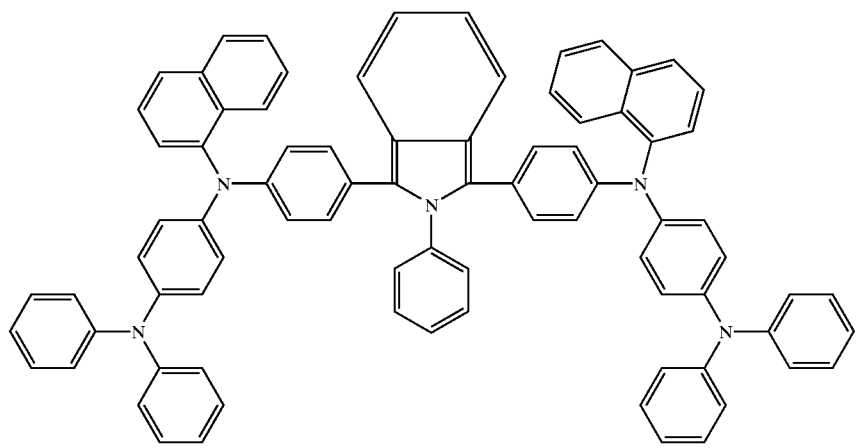
PD-51

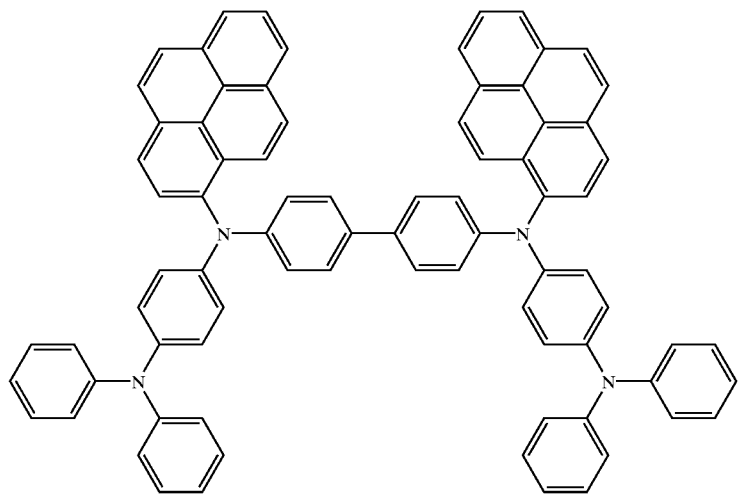
PD-52
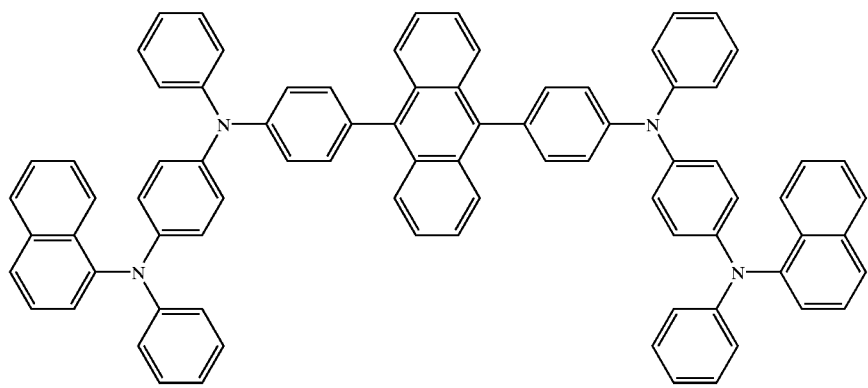
PD-53
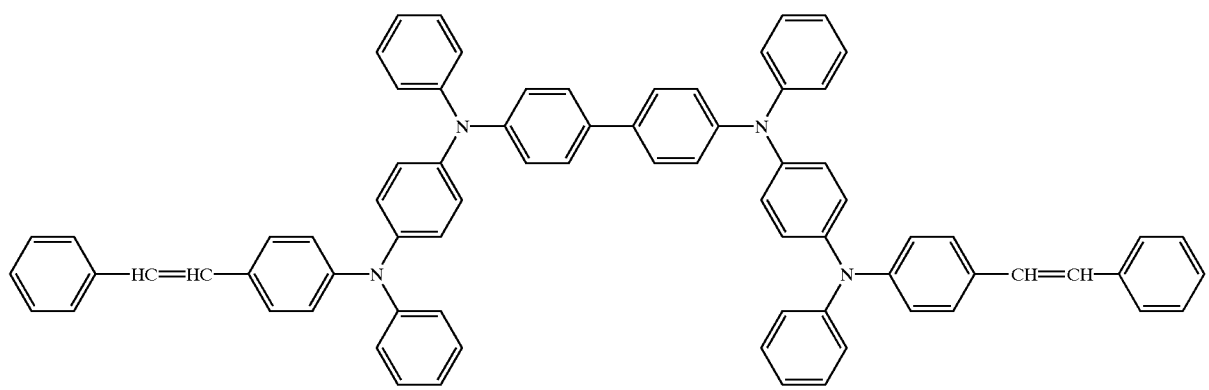
PD-54

-continued
PD-55
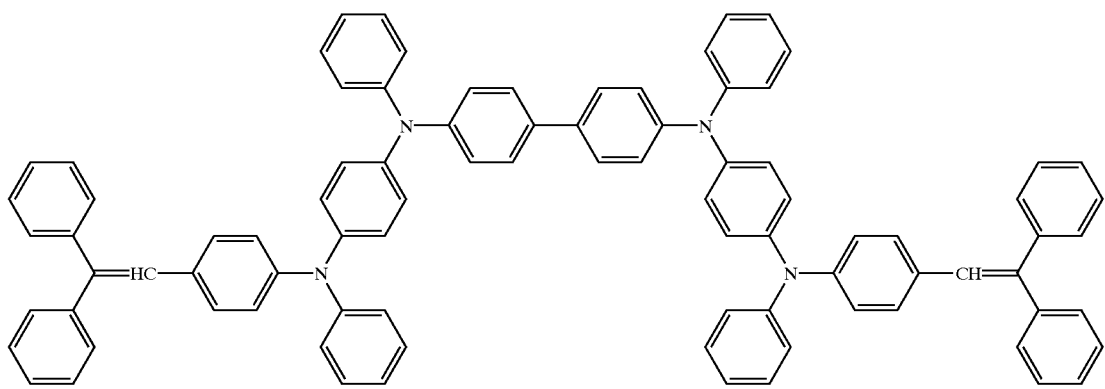
PD-56
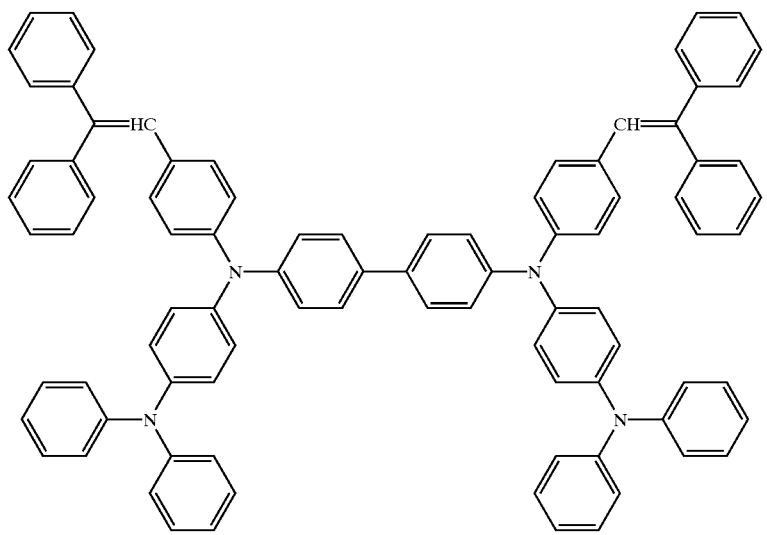
PD-57
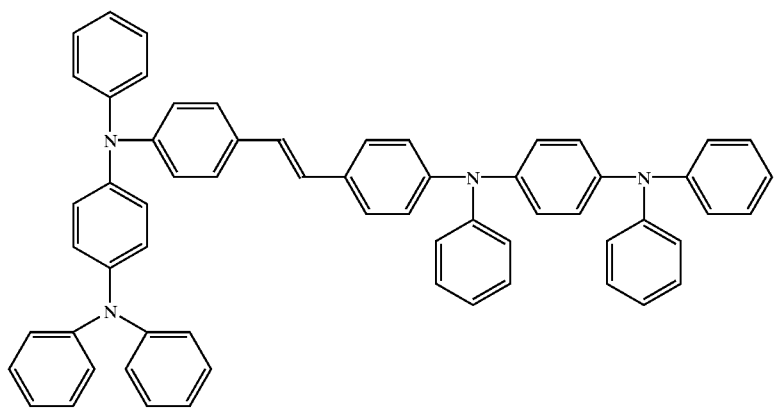
PD-58
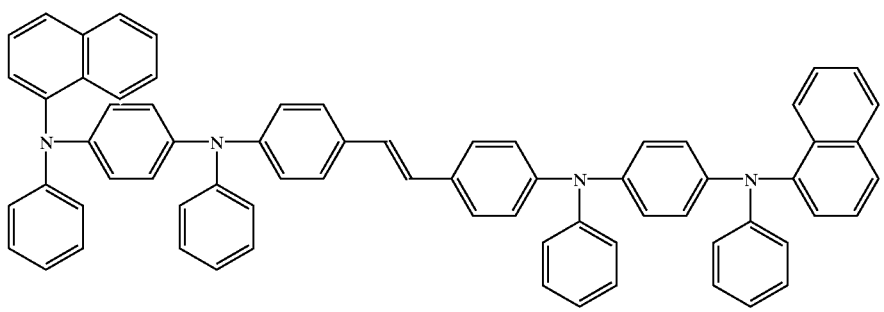

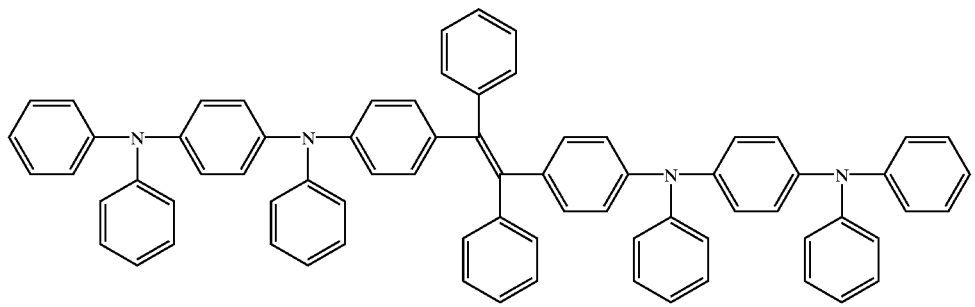
PD-59
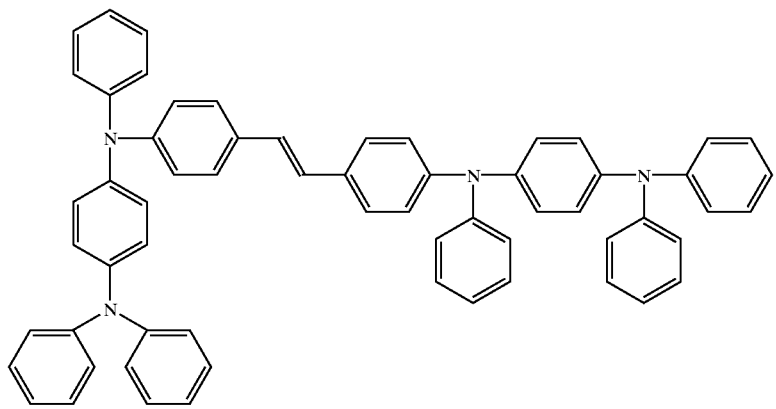
PD-57
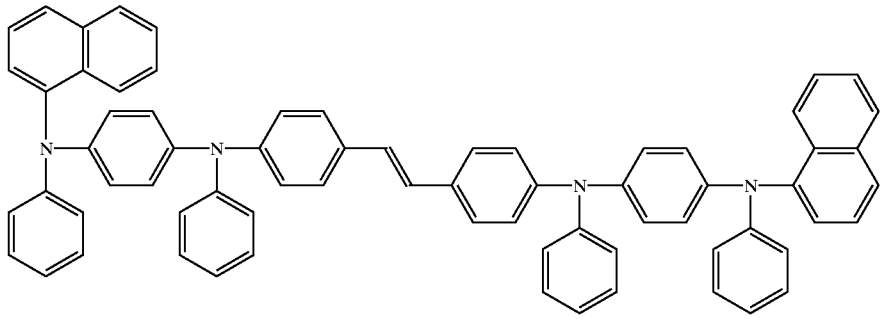
PD-58
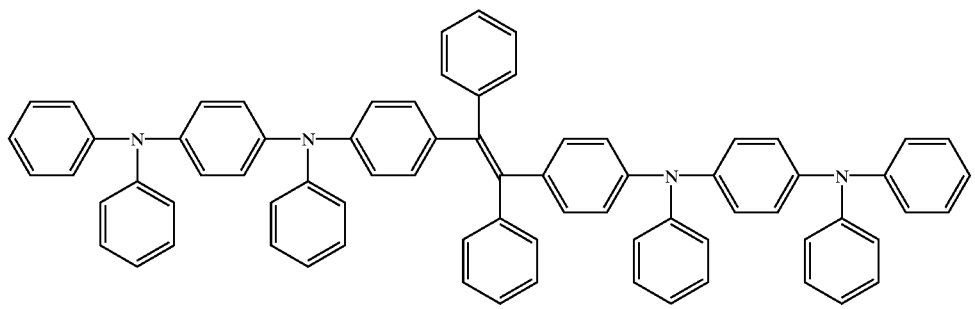
PD-59

Specific examples of the phenylenediamine derivative represented by the general formula (II) include the following compounds shown by (PT-01) to (PT-31). The invention is not limited to them.
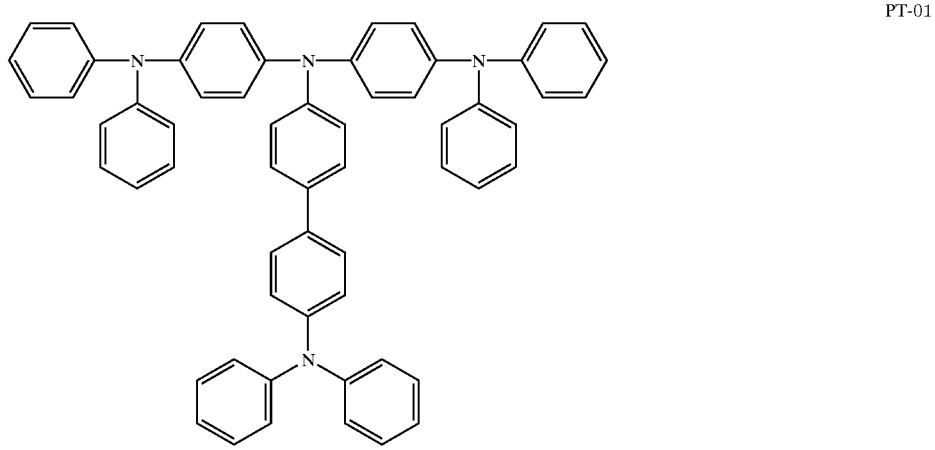
PT-01
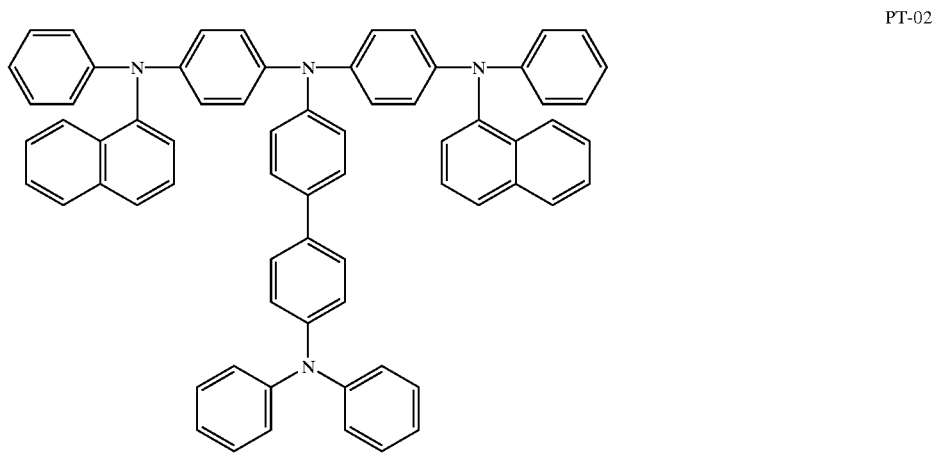
PT-02
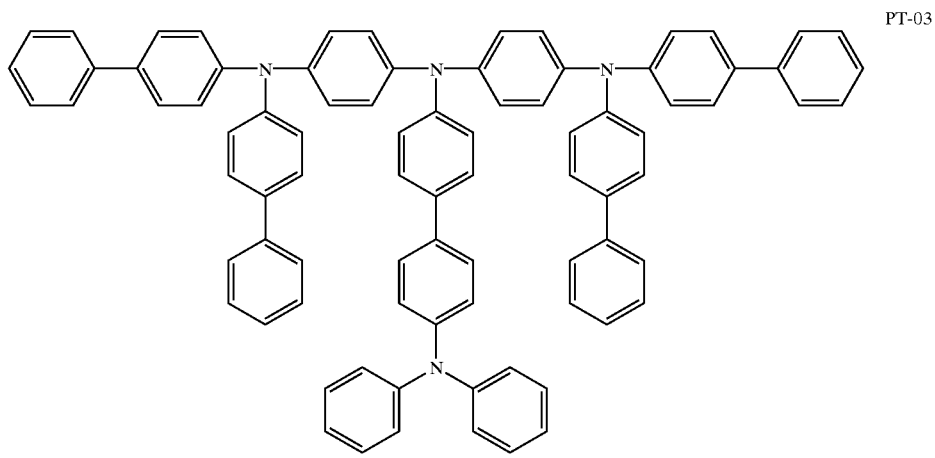
PT-03

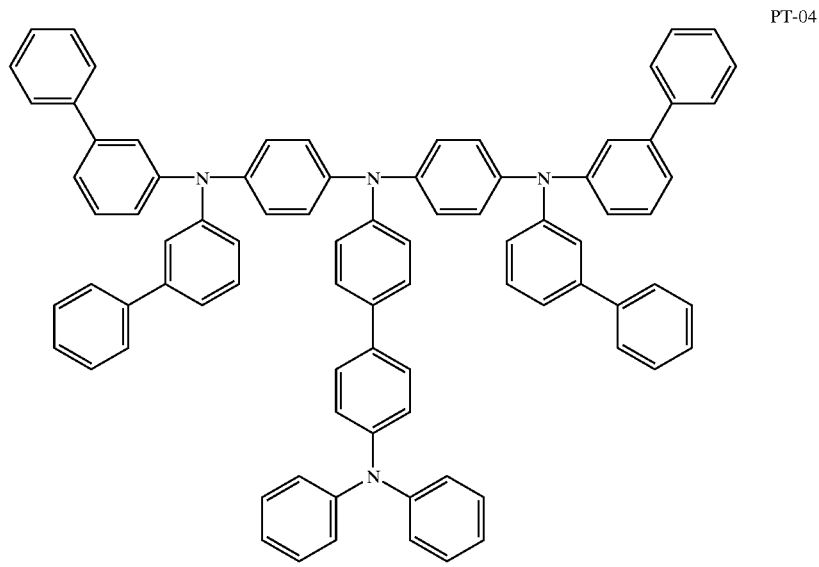
PT-04
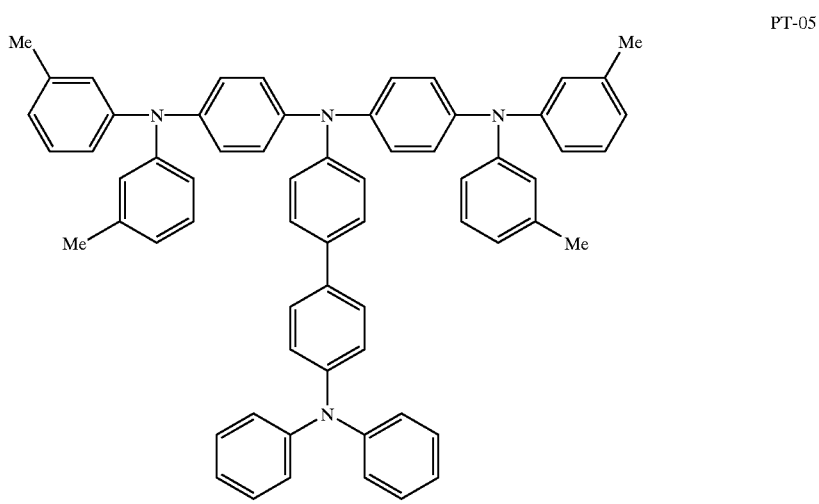
PT-05
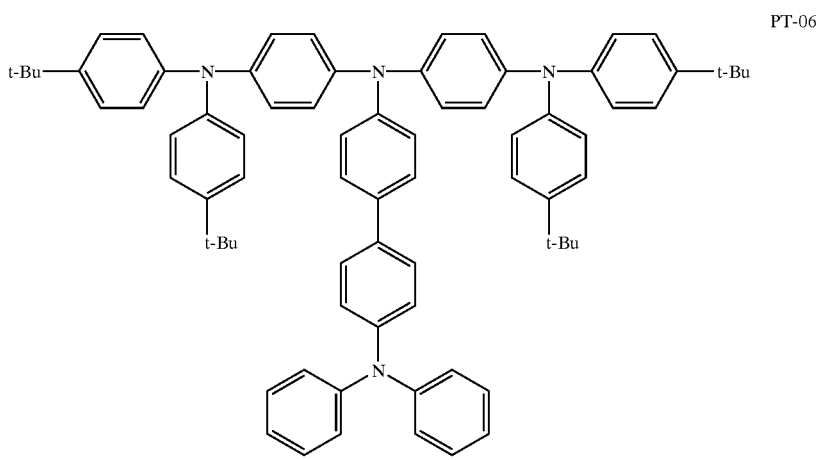
PT-06

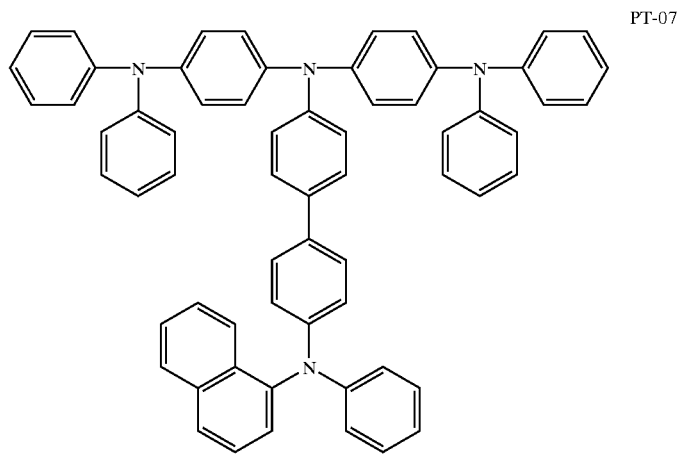
PT-07
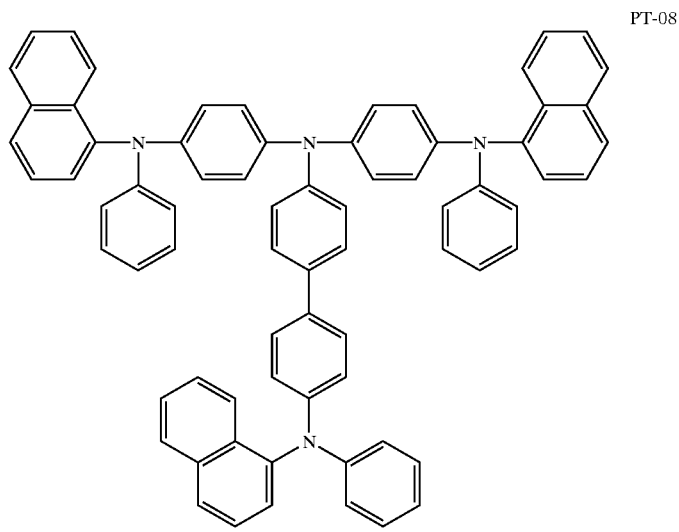
PT-08
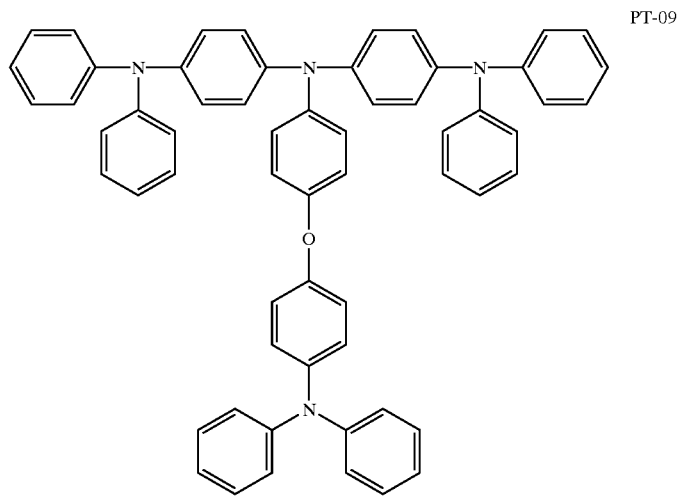
PT-09

-continued
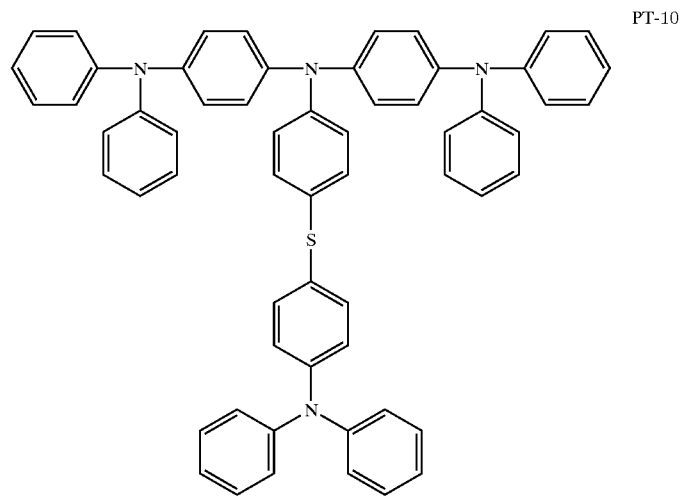
PT-10
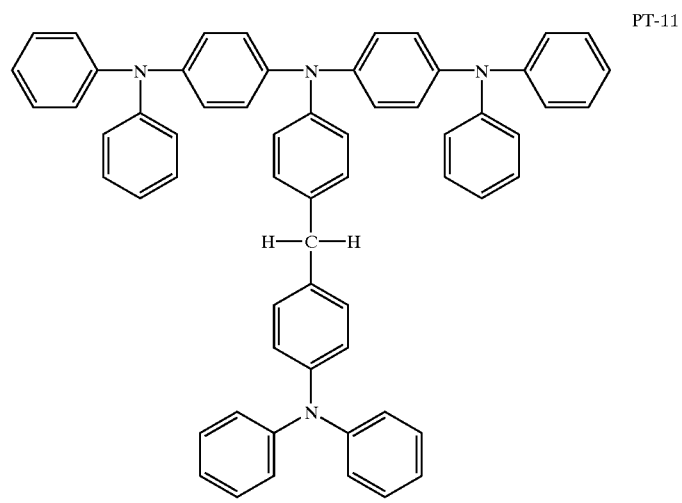
PT-11
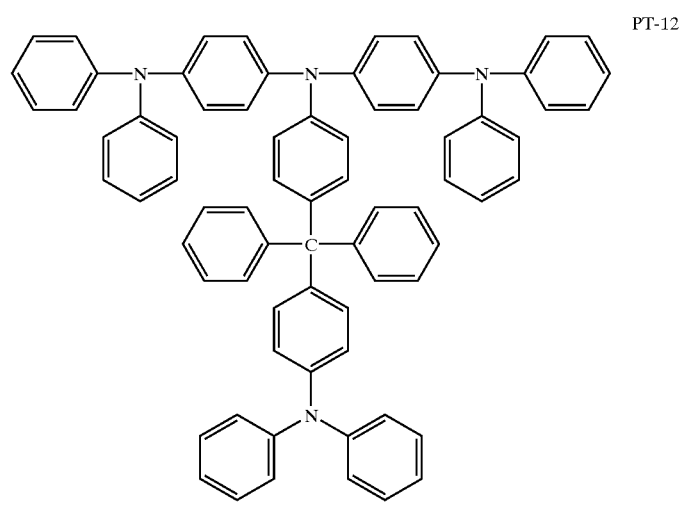
PT-12

-continued
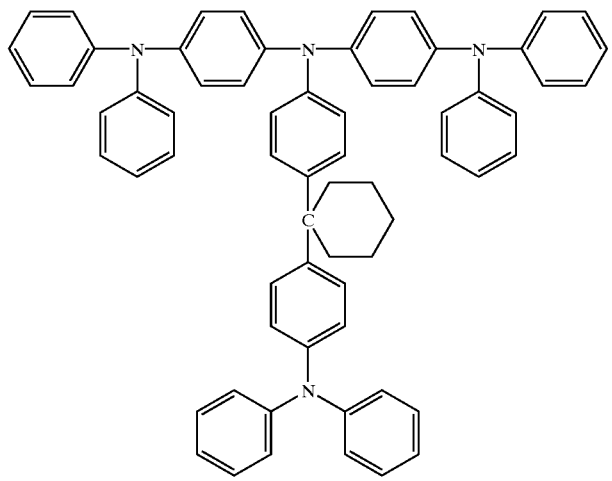
PT-13
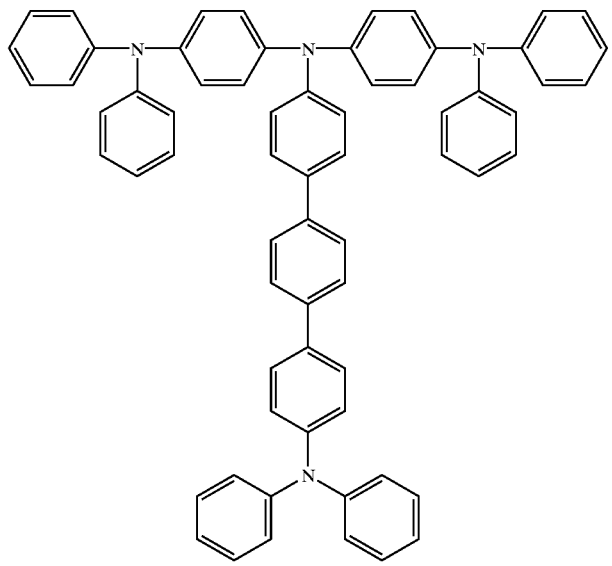
PT-14
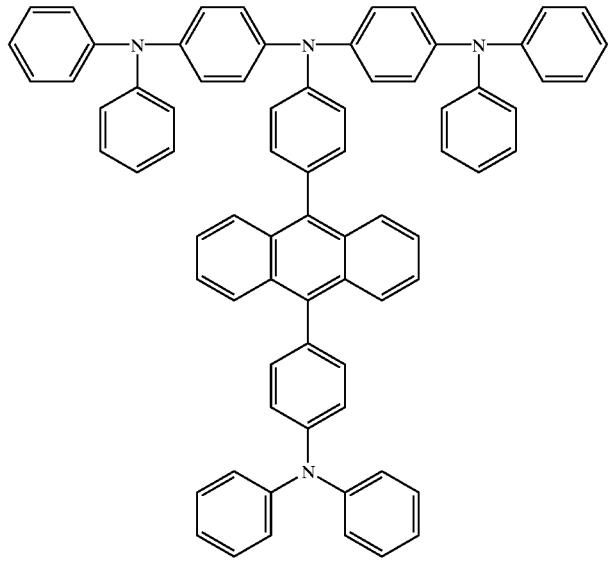
PT-15

-continued
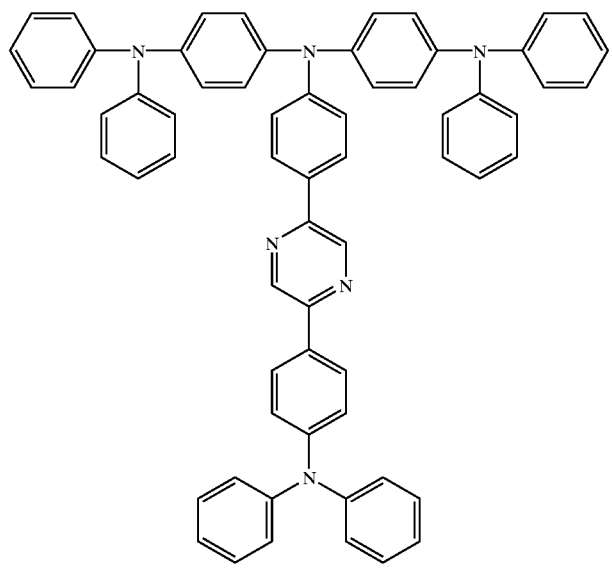
PT-16
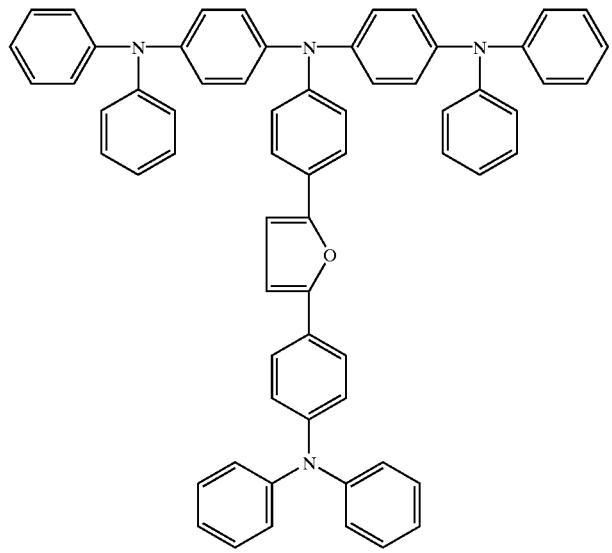
PT-17
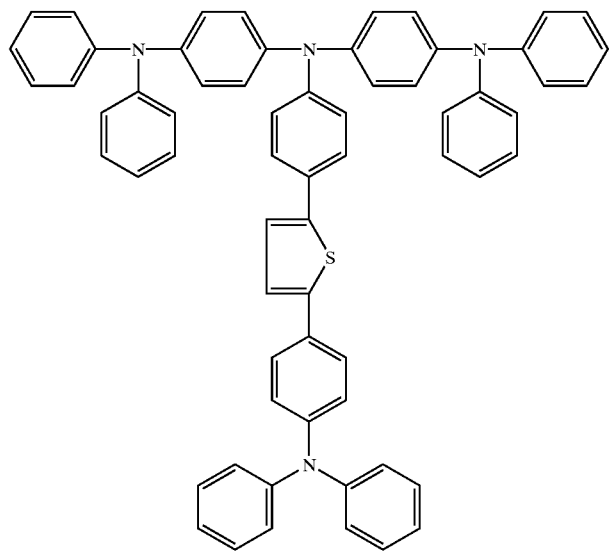
PT-18

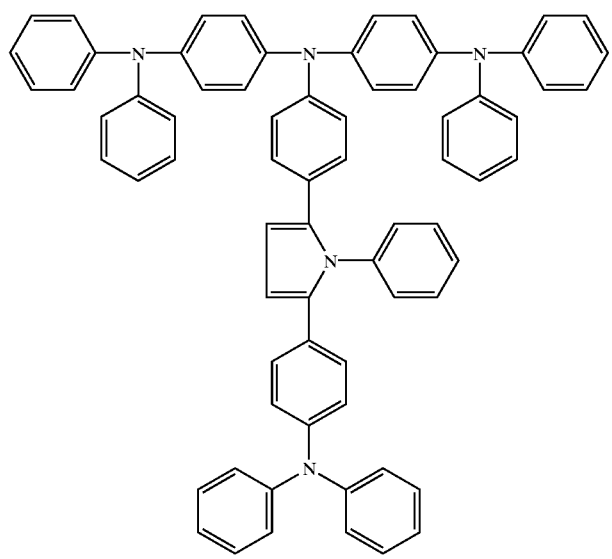
PT-19
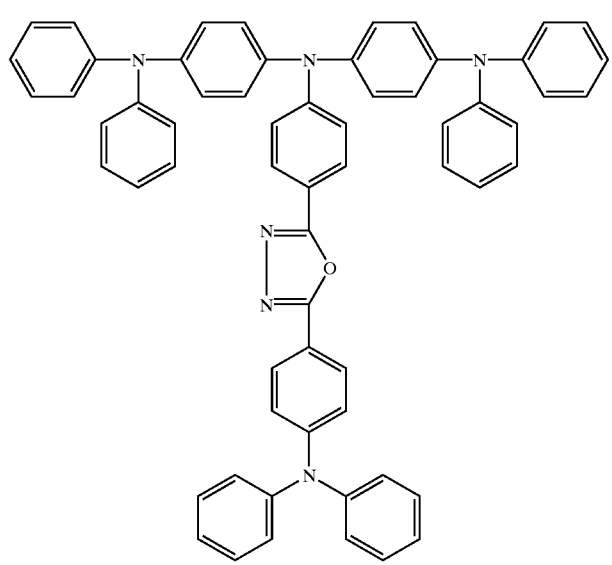
PT-20
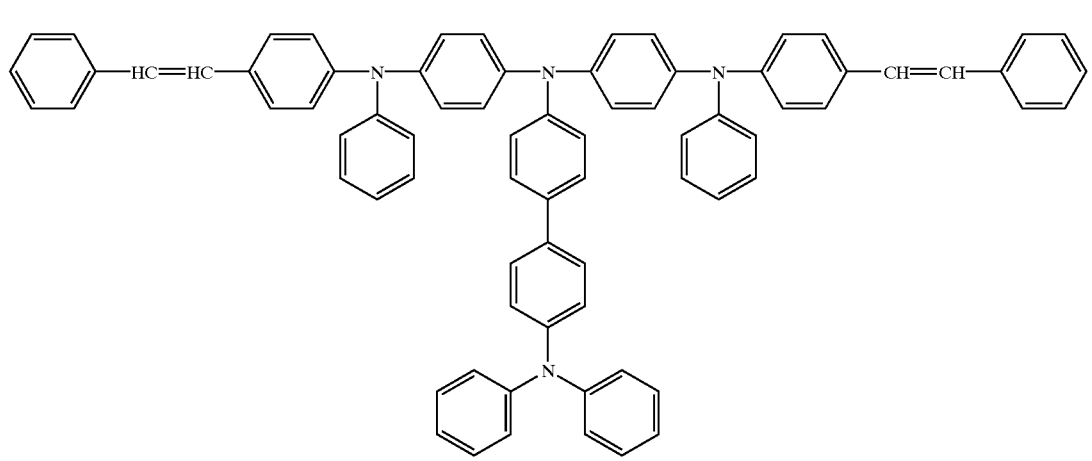
PT-21

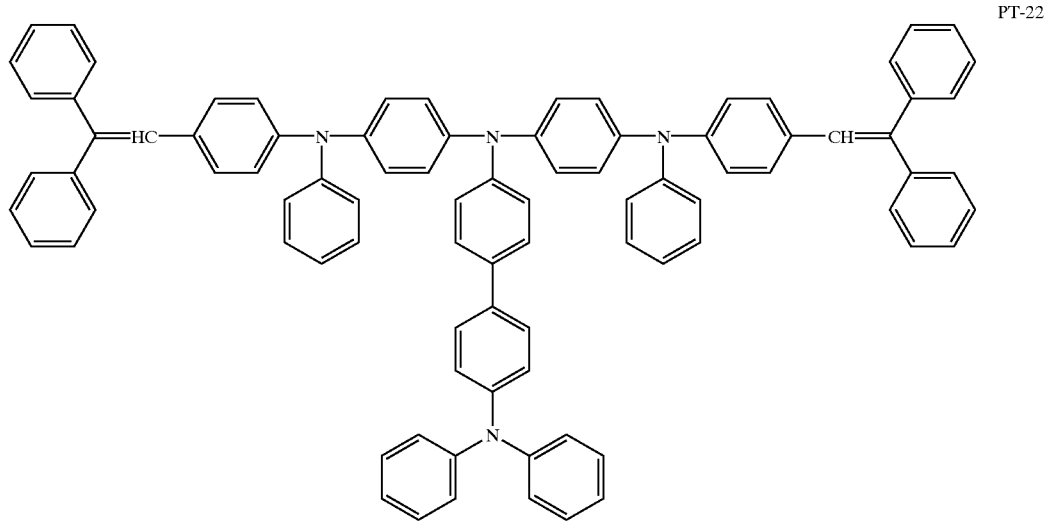
PT-22
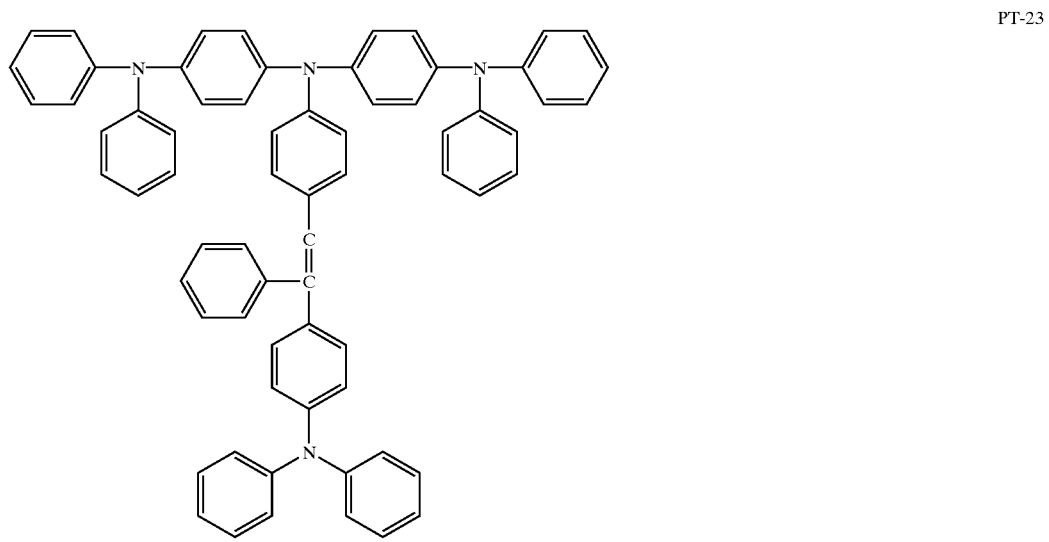
PT-23
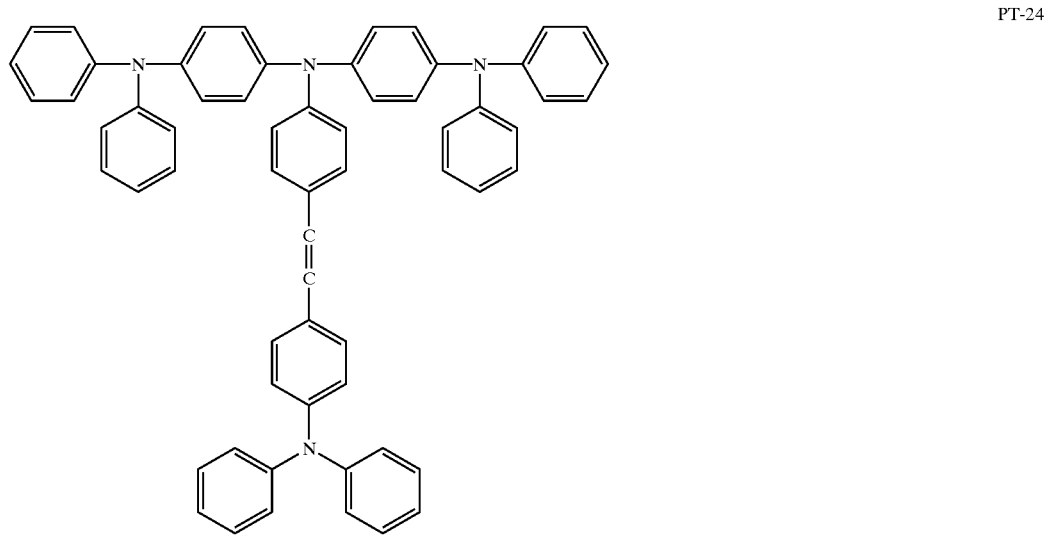
PT-24

PT-25
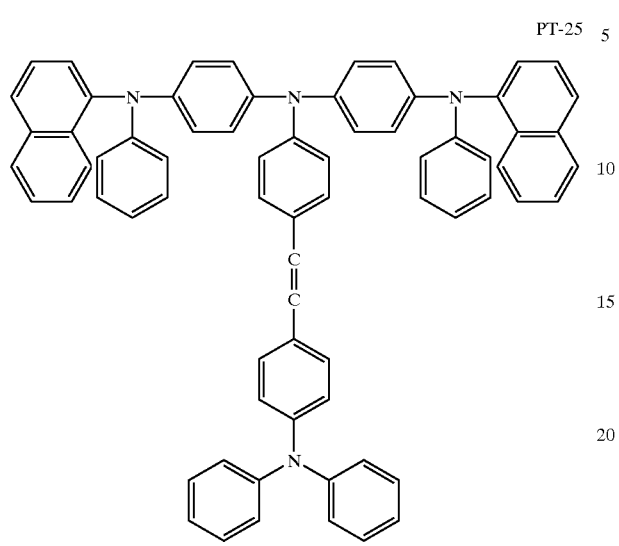
PT-26
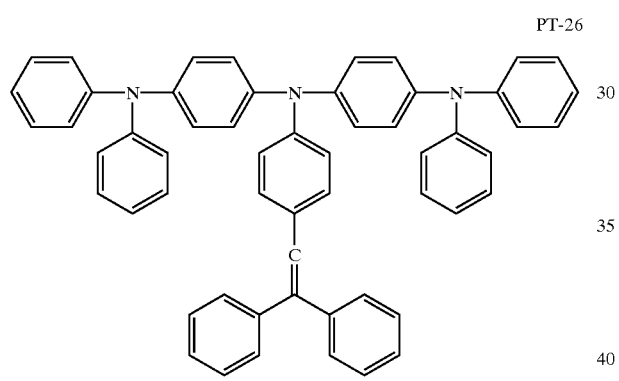
PT-27
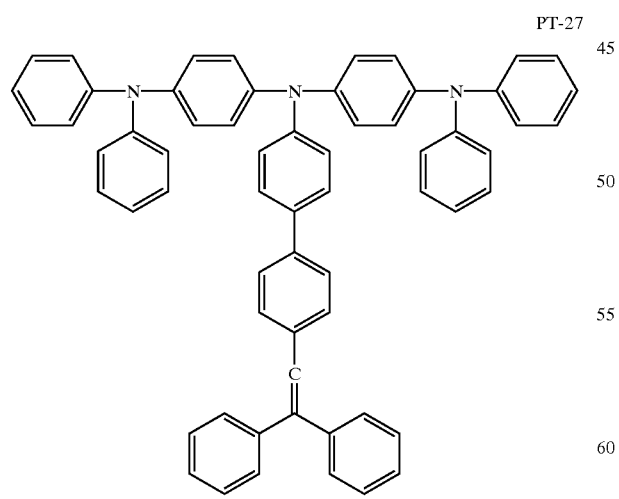
PT-28
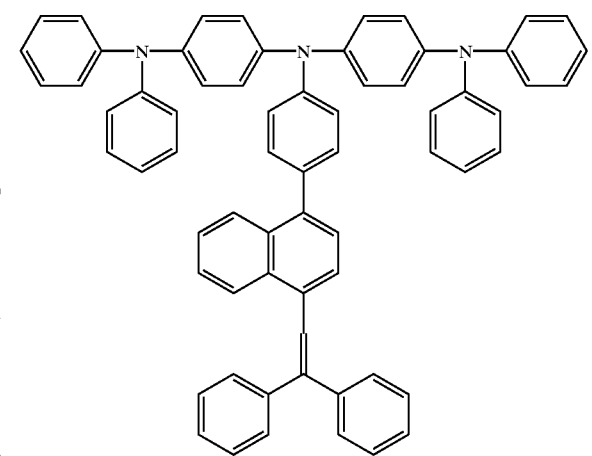
PT-29
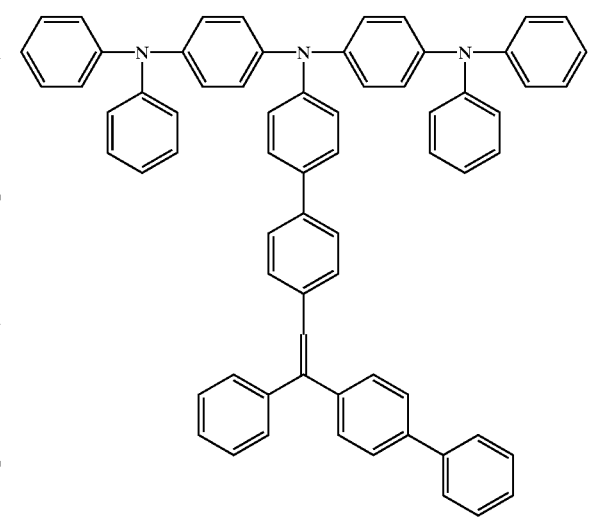
PT-30
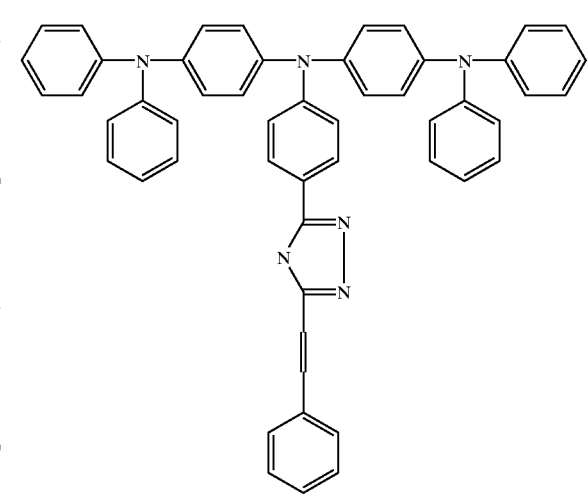

PT-31

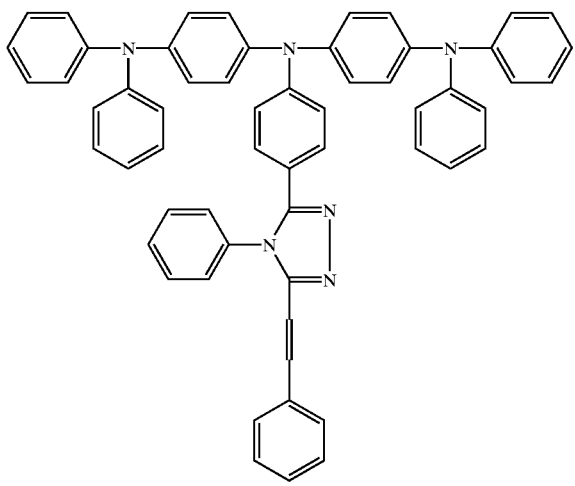

Because the compound of the general formulae (I), (II) and (II)' has a small ionization potential, impurities are liable to be mixed, such as oxidation on purifying, and the hole mobility may be decreased by the impurities in some cases That is, in th e method of JP-A-9-301934, because impurities are mixed in the high molecular weight aromatic amine compound as observed in the fluorescent spectrum, a sufficient hole mobility cannot be obtained due to traps and the like.

On the other hand, as a result of earnest investigation by the inventors with respect to the purification method of the compound, it has been found that a pure compound can be obtained by using a toluene/hexane series solvent as a solvent for column purification. According to the purification method, a compound obtained that has a higher purity than the method disclosed in JP-A-9-301934 using a halogen series solvent on column purification.

Furthermore, by conducting sublimation purification under high vacuum of 0.01 mmHg or less, a pure phenylenediamine dimer exhibiting a fluorescent spectrum, which is shown as in FIG. 1, having a peak wavelength within the range of from 400 to 480 nm can be obtained. The inventors have confirmed that a hole mobility of $10^{-4}$ cm$^2$/V·s or more is obtained only by the phenylenediamine dimer of the invention exhibiting blue or violet fluorescence (peak wavelength: 400 to 480 nm).

(B) Structure and Materials of Organic EL Device

Upon producing the organic EL device by using the compound of the invention, the structure and the materials that are generally used for producing an organic EL device can be employed.

Suitable structure and materials therefor will be described below.

(1) Structure of Organic EL Device

Representative examples of the structure of an organic EL device used in the invention are shown below. Of course, the invention is not limited to them.

(i) anode/light emitting layer/cathode
(ii) anode/hole injection layer/light emitting layer/cathode
(iii) anode/light emitting layer/electron injection layer/cathode
(iv) anode/hole injection layer/light emitting layer/electron injection layer/cathode
(v) anode/organic semiconductor layer/light emitting layer/cathode
(vi) anode/organic semiconductor layer/electron barrier layer/light emitting layer/cathode
(vii) anode/organic semiconductor layer/light emitting layer/adhesion improving layer/cathode
(viii) anode/hole injection layer/hole transporting layer/light emitting layer/electron injection layer/cathode Among these, the structure (viii) is generally preferred.

The compound of the invention is contained in the hole transporting zone of these constituting components. The amount to be contained is selected from the range of from 30 to 100 mol %.

(2) Light Transmitting Substrate

The organic EL device of the invention is produced on a light transmitting substrate. The light transmitting substrate herein is a substrate supporting the organic EL device, and is preferably a flat substrate having a transmittance to a visible light of from 400 to 700 nm of 50% or more.

Specific examples thereof include a glass plate, a polymer plate and the like. Examples of the glass plate particularly include soda lime glass, barium-strontium-containing glass, lead glass, aluminosilicate glass, borosilicate glass, barium borosilicate glass, quartz and the like. Examples of the polymer plate include polycarbonate, acryl, polyethyleneterephthalate, polyether sulfone, polysulfone and the like.

(3) Anode

As the anode, a metal, an alloy, an electroconductive compound and a mixture thereof having a large work function (4 eV or more) are preferably employed. Specific examples of such an electrode material include a metal, such as Au and the like, and an electroconductive material, such as CuI, ITO, SnO$_2$, ZnO and the like.

The anode can be produced by forming a thin film of the electrode material by a vapor deposition method, a sputtering method or the like.

In the case where the light emitted from the light emitting layer is obtained from the anode, it is preferred that the transmittance of the anode to the emitted light is 10% or more. The sheet resistance of the anode is preferably several hundreds ohm per square or less. The film thickness of the anode is generally selected, while depending on the material, from the range of from 10 nm to 1 µm, and preferably from 10 to 200 nm.

(4) Organic Light Emitting Layer

The light emitting layer of the organic EL device has the following functions in combination. That is, there are (i) injection function; a function in that under an electric field, a hole can be injected from a hole injection layer, and an electron can be injected from a cathode or an electron injection layer, (ii) transporting function; a function of transporting the injected charges (the electron and the hole) by the force of the electric field, and (iii) light emitting function; a function of providing a field of recombination between the electron and the hole to promote light emission.

There may be a difference between the liability of injecting the hole and the liability of injecting the electron, and there may be variety in transporting abilities represented by mobility of the hole and the electron, but it is preferred that one of the charges migrates.

The light emitting material of the organic EL device is mainly an organic compound, and specific examples are shown below depending on desired colors.

In the case where light emission from ultraviolet to violet region is obtained, the compounds represented by the following general formula can be exemplified.

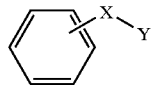

In the general formula, X represents the following compound.

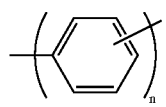

Herein, n is 2, 3, 4 or 5.

Y represents the following compound.

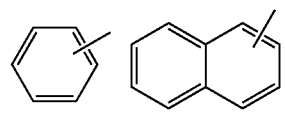

The compounds represented by the general formulae may be a phenyl group, a phenylene group or a naphthyl group substituted with a single or plural groups, such as an alkyl group having from 1 to 4 carbon atom(s), an alkoxy group, a hydroxyl group, sulfonyl, a carbonyl group, an amino group, a dimethylamino group, a diphenylamino group and the like.

They may be bonded to each other to form a saturated 5-membered ring or a saturated 6-membered ring. Those bonded to a phenyl group, a phenylene group or a naphthyl group at the para-position is preferred for forming a flat vapor deposition film owing to the good bonding property.

Specifically, the following compounds are exemplified. In particular, a p-quarterphenyl derivative and a p-quinquephenyl derivative are preferred.

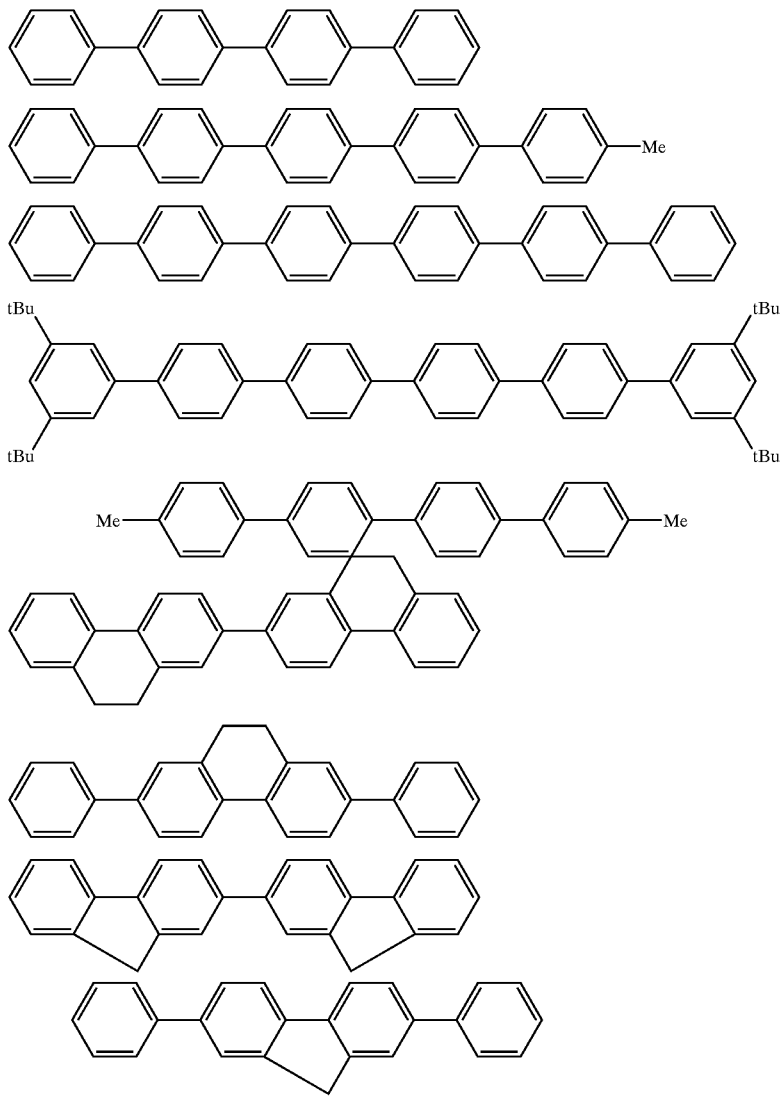

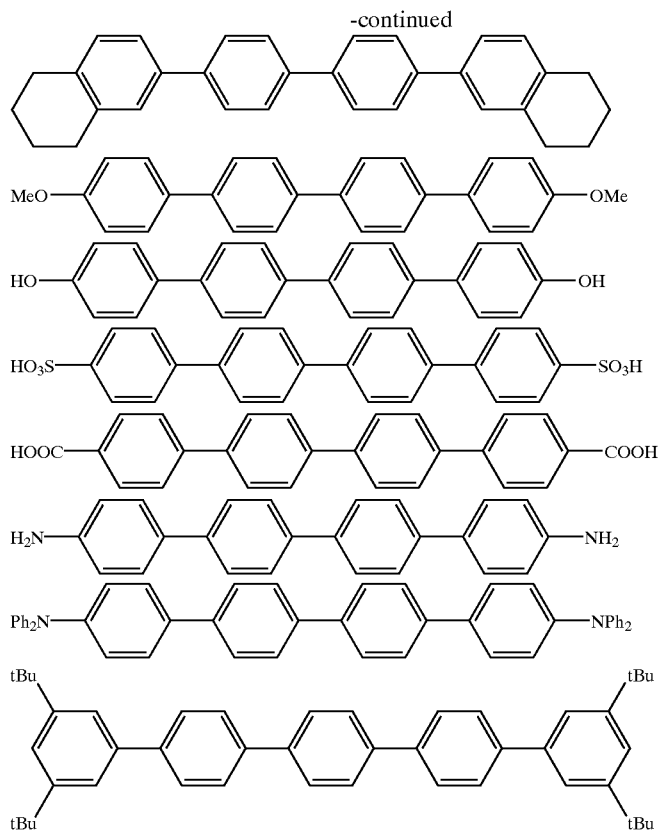

In order to obtain light emission of from blue color to green color, a fluorescent whitening agent, such as a benzothiazole series, a benzoimidazole series, a benzoxazole series and the like, a metal-chelated oxinoid compound, and a styrylbenzene series compound.

As shown by the specific compound names, for example, those disclosed in JP-A-59-194393 can be exemplified. Other useful compounds are listed in *Chemistry of Synthetic Dyes*, 1971, pp. 628 to 637 and 640.

As the metal-chelated oxinoid compound, for example, those disclosed in JP-A-63-295695 can be used. Representative examples thereof include an 8-hydroxyquinoline series metallic complex, such as tris(8-quinolyl)aluminum (hereinafter abbreviated as Alq) and the like, dilithiumepndolidione and the like.

As the styrylbenzene series compound, for example, those disclosed in European Patent No. 0,319,881 and European Patent No. 0,373,582 can be used.

A distyrylpyrazine derivative disclosed in JP-A-2-252793 can be used as a material for the light emitting layer.

As other examples, for example, a polyphenyl series compound disclosed in European Patent No. 0,387,715 can also be used as a material for the light emitting layer.

Other than the fluorescent whitening agent, the metal-chelated oxinoid compound, the styrylbenzene series compound and the like, for example, 12-phthaloperinone (*J. Appl. Phys.*, vol. 27, L713 (1988)), 1,4-diphenyl-1,3-butadiene and 1,1,4,4-tetraphenyl-1,3-butadiene (*Appl. Phys. Lett.*, vol. 56, L799 (1990)), a naphthalimide derivative (JP-A-2-305886), a perylene derivative (JP-A-2-189890), an oxadiazole derivative (JP-A-2-216791, or an oxadiazole derivative disclosed by Hamada et al. in the 38th United Lectures relating to Applied Physics), an aldazine derivative (JP-A-2-220393), a pyraziline derivative (JP-A-2-220394), a cyclopentadiene derivative (JP-A-2-289675), a pyrrolopyrrol derivative (JP-A-2-296891), a styrylamine derivative (*Appl. Phys. Lett.*, vol. 5, L799 (1990)), a coumalin series compound (JP-A-2-191694), a high molecular weight compound disclosed in International Patent Publication WO90/13148 and *Appl. Phys. Lett.*, vol. 158, 18, p. 1982 (1991) and the like may also be used as a material for the light emitting layer.

In the invention, it is preferred to use an aromatic dimethylidyne series compound (those disclosed in European Patent No. 0,388,768 and JP-A-3-231970) as a material for the light emitting layer. Specific examples thereof include 4,4'-bis(2,2-di-t-butylphenylvinyl)biphenyl (hereinafter abbreviated as DTBPBBi), 4,4'-bis(2,2-diphenylvinyl)biphenyl (hereinafter abbreviated as DPVBi) and the like, as well as an derivative thereof.

Furthermore, a compound represented by the general formula $(Rs—Q)_2—Al—O—L$ disclosed in JP-A-5-258862 can be exemplified. (In the formula, L represents a hydrocarbon having from 6 to 24 carbon atoms containing a phenyl part, O—L represents a phenolate ligand, Q represents a substituted 8-quinolinolate ligand, and Rs represents a substituent on the 8-quinolinolate ring selected to inhibit by steric hindrance two or more of the substituted B-quinolinolate ligands bonded to the aluminum atom.)

Specific examples thereof include bis(2-methyl-8-quinolilate)(para-phenylphenolate)aluminum(III) (hereinafter referred to as PC-7), bis(2-methyl-8-quinolilate)(1-naphtholate)aluminum(III) (hereinafter referred to as PC-17) and the like.

Additionally, a method for obtaining mixed light emission of blue color and green color with high efficiency using doping according to JP-A-6-9953 can be exemplified. In this case, the light emitting materials described in the foregoing can be exemplified as the host, and a strong fluorescent dye of from blue color to green color, for example, a coumalin series and the similar fluorescent dye used as the host, can be exemplified as the dopant.

Specifically, examples of the host include a light emitting material having a distyrylarylene skeleton, and particularly preferably DPVBi, and examples of the dopant include diphenylaminovinylarylene, and particularly preferably, for example, N,N-diphenylaminovinylbenzene (DPAVB).

A light emitting layerobtaining emission of white light is not particularly limited, and examples thereof include the following.

(i) Energy levels of the respective layers of the organic EL laminated structure are specified, and light emission is conducted by utilizing tunnel injection. (European Patent No. 0,390,551)

(ii) A device utilizes tunnel injection similar to (i) with a white light emitting device disclosed as an example. (JP-A-3-230584)

(iii) A light emitting layer having a 2-layer structure is disclosed. (JP-A-2-220390 and JP-A-2-216790)

(iv) A light emitting layer is divided into plural parts, each of which is constituted by materials having different light emission wavelengths. (JP-A-4-51491)

(v) A blue light emitting substance (fluorescent peak: 380 to 480 nm) and a green light emitting substance (480 to 580 nm) are accumulated, and a red fluorescent substance is contained. (JP-A-6-207170)

(vi) A blue light emitting layer contains a blue fluorescent dye, a green light emitting layer contains a red fluorescent dye and a green fluorescent substance. (JP-A-7-142169)

Among these, the structure (v) is preferably employed.

Examples of the red fluorescent substance are shown below.

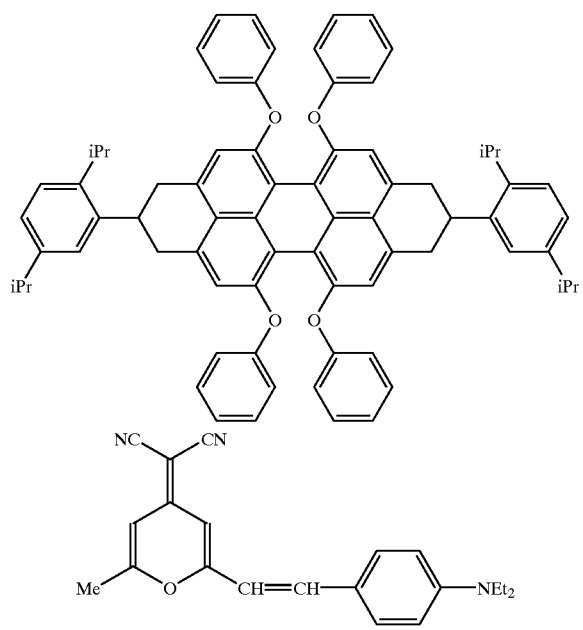

-continued

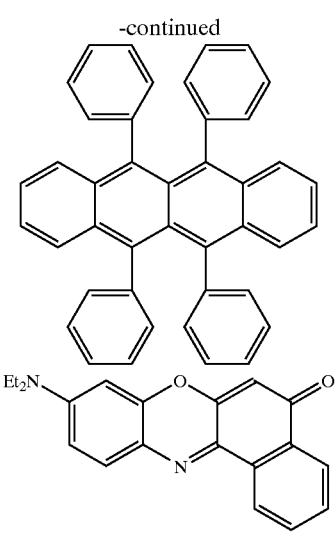

As a method for forming the light emitting layer using the material described in the foregoing, a known method, such as a vapor deposition method, a spin coating method, an LB method and the like, can be applied.

It is particularly preferred that the light emitting layer is a molecular accumulated film. The molecular accumulated film herein means a thin film formed by depositing from the material compound in a gaseous state and a film formed by solidifying from the material compound in a solution state or a liquid state, and the molecular accumulated film can be distinguished from a thin film formed by an LB method (molecular accumulated film) by the difference in aggregation structure and high dimensional structure and the functional difference derived therefrom.

Furthermore, as disclosed in JP-A-57-51781, the light emitting layer can be formed by dissolving a binder, such as a resin, and the material compound in a solvent to form a solution, and then making it to a thin film by a spin coating method or the like.

The film thickness of the light emitting layer thus formed is not particularly limited, and is appropriately selected depending on the circumstances, and in general, it is preferably in the range of from 5 nm to 5 $\mu$m. The light emitting layer may be constituted by a single layer comprising one or two or more of the materials, or may be formed by accumulating with a light emitting layer comprising a compound of a different kind from the light emitting layer described above.

(5) Hole Injection Layer and Hole Transporting Layer

The hole injection and transporting layers are layers assisting the injection of a hole to the light emitting layer and transporting it to a light emitting region, and has a large hole mobility and a small ionization energy, which is generally 5.5 eV or less. As the hole injection and transporting layers, a material transporting a hole to the light emitting layer under a lower electric field intensity is preferred, and the hole mobility thereof is preferably at least $10^{-4}$ cm$^2$/V·s under an electric field of from $10^4$ to $10^6$ V/cm.

As the hole injection and transporting material, the phenylenediamine derivative represented by the general formula (I) or the general formula (II) is preferably used. In this case, the sole compound of the invention is used for forming the hole injection and transporting layers, or the material may be used by mixing with other materials.

As the material that is mixed with the compound of the invention to form the hole injection and transporting layers is not particularly limited as far as they have the preferred properties described in the foregoing, and an arbitrary one may be used selected from those conventionally used as the charge transporting material of a hole in the photoconductive material and known ones used in a hole injection layer of an EL device.

Specific examples thereof include a triazole derivative (see U.S. Pat. No. 3,112,197), an oxadiazole derivative (see U.S. Pat. No. 3,189,447), an imidazole derivative (see JP-B-37-16096), a polyarylalkane derivative (see U.S. Pat. No. 3,615,402, U.S. Pat. No. 3,820,989, U.S. Pat. No. 3,542,544, JP-B-45-555, JP-B-51-10983, JP-A-51-93224, JP-A-55-17105, JP-A-56-4148, JP-A-55-108667, JP-A-55-156953 and JP-A-56-36656), a pyrazoline derivative and a pyrazolone derivative (see U.S. Pat. No. 3,180,729, U.S. Pat. No. 4,278,749, JP-A-55-88064, JP-A-55-88065, JP-A-49-105537, JP-A-55-51086, JP-A-56-80051, JP-A-56-88141, JP-A-57-45545, JP-A-54-112637 and JP-A-55-74546), a phenylenediamine derivative (see U.S. Pat. No. 3,615,404, JP-B-51-10105, JP-B-46-3712, JP-B-47-25336, JP-A-54-53435, JP-A-54-110536 and JP-A-54-119925), an arylamine derivative (see U.S. Pat. No. 3,567,450, U.S. Pat. No. 3,180,703, U.S. Pat. No. 3,240,597, U.S. Pat. No. 3,658,520, U.S. Pat. No. 4,232,103, U.S. Pat. No. 4,175,961, U.S. Pat. No. 4,012,376, JP-B-49-35702, JP-B-39-27577, JP-A-55-144250, JP-A-56-119132, JP-A-56-22437 and West German Patent No. 1,110,518), an amino-substituted chalcone derivative (see U.S. Pat. No. 3,526,501), an oxazole derivative (those disclosed in U.S. Pat. No. 3,257,203), a styrylanthracene derivative (see JP-A-56-46234), a fluorenone derivative (see JP-A-54-110837), a hydrazone derivative (see U.S. Pat. No. 3,717,462, JP-A-54-59143, JP-A-55-52063, JP-A-55-52064, JP-A-55-46760, JP-A-55-85495, JP-A-57-11350, JP-A-57-148749 and JP-A-2-311591), a stilbene derivative (see JP-A-61-210363, JP-A-61-228451, JP-A-61-14642, JP-A-61-72255, JP-A-62-47646, JP-A-62-36674, JP-A-62-10652, JP-A-62-30255, JP-A-60-93455, JP-A-60-94462, JP-A-60-174749 and JP-A-60-175052), a silazane derivative (U.S. Pat. No. 4,950,950), a polysilane series (JP-A-2-204996), an aniline series copolymer (JP-A-2-282263), an electroconductive high molecular weight oligomer (particularly a thiophene oligomer) disclosed in JP-A-1-211399, and the like.

Those described in the foregoing can be used as the material for the hole injection layer, and the use of a porphyrin compound (those disclosed in JP-A-63-2956965), and an aromatic tertiary amine compound and a styrylamine compound (see U.S. Pat. No. 4,127,412, JP-A-53-27033, JP-A-54-58445, JP-A-54-149634, JP-A-54-64299, JP-A-55-79450, JP-A-55-144250, JP-A-56-119132, JP-A-61-295558, JP-A-61-98353 and JP-A-63-295695) is preferred, with the use of the aromatic tertiary amine compound being particularly preferred.

Furthermore, a compound having two condensed aromatic rings in the molecule disclosed in U.S. Pat. No. 5,061,569, such as 4,4'-bis(N-(1-naphthyl)-N-phenylamino) biphenyl (hereinafter abbreviated as NPD), and 4,4',4"-tris (N-(3-methylphneyl)-N-phenylamino)triphenylamine (hereinafter abbreviated as MTDATA), in which three triphenylamine units are bonded in a star-burst type disclosed in JP-A-4-308688 can be exemplified.

As the material for the light emitting layer, in addition to the aromatic dimethylidyne compound, an inorganic compound, such as p-type Si, p-type SiC and the like, can be used as the material for the hole injection layer.

The hole injection and transporting layers can be formed by making the compound into a thin film by a known method, such as a vacuum vapor deposition method, a spin coating method, a casting method, an LB method and the like. The film thickness of the hole injection and transporting layers is not particularly limited, and is generally from 5 nm to 5 μm. When the compound of the invention is contained in the hole transporting zone, the hole injection and transporting layers may be constituted by one layer comprising one or two or more kinds of the materials, or may be formed by accumulating another hole injection and transporting layers comprising the other compound than the hole injection and transporting layers described above.

The organic semiconductor layer is a layer assisting injection of a hole or injection of an electron into the light emitting layer, and preferably has a conductivity of $10^{-10}$ S/cm or more. Examples of the material for the organic semiconductor layer include a conductive dendrimer, such as a thiophene-containing oligomer, an arylamine-containing oligomer disclosed in JP-A-8-193191, an arylamine-containing dendrimer and the like.

(6) Electron Injection Layer

The electron injection layer is a layer assisting injection of an electron into the light emitting layer, and has a large electron mobility, and the adhesion improving layer is a layer exhibiting particularly good adhesion to the cathode among the electron injection layers. As the material used in the electron injection layer, 8-hydroxyquinoline and a metallic complex of a derivative thereof.

Specific examples of 8-hydroxyquinoline and the metallic complex of a derivative thereof include a metallic chelate oxinoid compound containing a chelate of oxine (in general, 8-quinolinol or 8-hydroxyquinoline).

For example, Alq disclosed for the light emitting material can be used as the electron injection layer.

On the other hand, examples of the oxadiazole derivative include the following electron transmitting compounds.

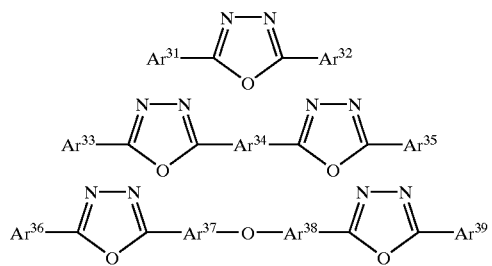

(In the formulae, $Ar^{31}$, $Ar^{32}$, $Ar^{33}$, $Ar^{35}$, $Ar^{36}$ and $Ar^{39}$ each represents a substituted or unsubstituted aryl group, which may be the same or different. $Ar^{34}$, $Ar^{37}$ and $Ar^{38}$ represent a substituted or unsubstituted arylene group, which may be the same or different.)

Examples of the aryl group include a phenyl group, a biphenyl group, an anthranyl group, a perylenyl group and a pyrenyl group. Examples of the arylene group include a phenylene group, a naphthylene group, a biphenylene group, an anthranylene group, a perylenylene group, a pyrenylene group and the like. Examples of the substituent include an alkyl group having from 1 to 10 carbon atom(s), an alkoxy group having from 1 to 10 carbon atom(s), a cyano group and the like. The electron transmitting compound is preferably those that can be formed into a thin film.

Specific examples of the electron transmitting compound include the following.

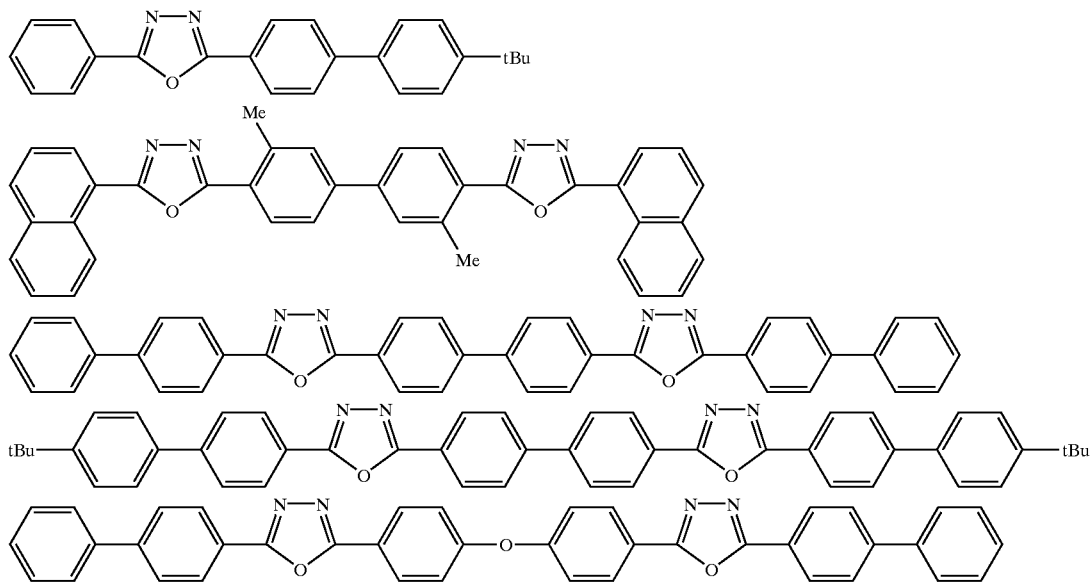

(7) Cathode

As the cathode, those comprising a metal, an alloy and an electroconductive compound having a small work function (4 eV or less), as well as a mixture thereof as an electrode substance are employed. Specific examples of the electrode substance include sodium, a sodium-potassium alloy, magnesium, lithium, a magnesium-silver alloy, aluminum/aluminum oxide, an aluminum-lithium alloy, indium, a rare earth metal and the like.

The cathode can be produced by forming the electrode substance into a thin film by amethod, such as vapor deposition, sputtering or the like.

In the case where the light emitted from the light emitting layer is obtained from the cathode, it is preferred that the transmittance of the cathode to the emitted light is 10% or more.

The sheet resistance of the cathode is preferably several hundreds ohm per square or less, and the film thickness is generally from 10 nm to 1 $\mu$m, and preferably from 50 to 200 nm.

(8) Production of Organic EL Device

According to the materials and methods described in the foregoing, an anode, a light emitting layer, a hole injection layer depending on necessity, and an electron injection layer depending on necessity are formed, and then a cathode is further formed, so as to produce the organic EL device. Alternatively, the organic EL device can be produced from the cathode to the anode in the order contrary to the above.

A production example will be described below, which has a structure comprising a light transmitting substrate having thereon an anode/a hole injection layer/a light emitting layer/an electron injection layer/a cathode in this order.

On a suitable light transmitting substrate, a thin film comprising an anode material is formed to have a film thickness of 1 $\mu$m or less, preferably from 10 to 200 nm, by a method, such as vapor deposition, sputtering or the like, so as to produce an anode.

A hole injection layer is then formed on the anode. While the formation of the hole injection layer can be conducted by a method, such as a vacuum vapor deposition method, a spin coating method, a casting method, an LB method and the like, as described in the foregoing, it is preferred to form by a vacuum vapor deposition method since a uniform film can be easily obtained and a pinhole is difficult to form. In the case where the hole injection layer is produced by the vacuum vapor deposition method, the vapor deposition conditions vary depending on the compound used (the material for the hole injection layer), the crystalline structure and the association structure of the objective hole injection layer, and the like. In general, it is preferred that the conditions are appropriately selected from the temperature of the vapor deposition source of from 50 to 450° C., the degree of vacuum of from $10^{-7}$ to $10^{-3}$ torr, the vapor deposition rate of from 0.01 to 50 nm/sec, the substrate temperature of from −50 to 300° C., and the film thickness of from 5 nm to 5 $\mu$m.

The formation of the light emitting layer, in which the light emitting layer is provided on the hole injection layer, can be conducted by forming the desired organic light emitting material into a thin film by a method, such as a vacuum vapor deposition method, sputtering, a spin coating method, a casting method and the like, and it is preferred to form by a vacuum vapor deposition method since a uniform film can be easily obtained and a pinhole is difficult to form. In the case where the light emitting layer is produced by the vacuum vapor deposition method, the vapor deposition conditions vary depending on the compound used, and can be generally selected from the similar ranges of the conditions as the hole injection layer.

The electron injection layer is provided on the light emitting layer. As similar to the hole injection layer and the light emitting layer, it is preferred to form by a vacuum vapor deposition method to necessarily obtain a uniform film. The vapor deposition conditions may be selected from the similar ranges of the conditions as the hole injection layer and the light emitting layer.

While depending on the layer containing the hole transporting zone, the compound of the invention can be subjected to co-vapor deposition with other materials when the vacuum vapor deposition method is used. When the spin coating method is used, the other materials can be contained by mixing.

The cathode is finally accumulated to obtain the organic EL device.

The cathode comprises a metal and can be formed by a vapor deposition method or sputtering. However, in order to protect the underlying organic layer from damage on forming the film, the vacuum vapor deposition method is preferred.

The organic EL device described in the foregoing is preferably produced with a single shot of evacuation continuously from the anode through the cathode.

In the case where a direct current voltage is applied to the organic EL device, light emission can be observed when a voltage of from 5 to 40 V is applied with the anode being positive and the cathode being negative. When the voltage is applied with the reverse polarity, no electric current flows, and light emission does not occur. Furthermore, when a alternating current voltage is applied, uniform light emission is observed when the polarity becomes such a state that the anode is positive and the cathode is negative. The wave form of the alternating current may be arbitrary.

Phenylenediamine Derivative

Examples of substituents, which may be added to the aryl group having from 6 to 24 nucleus carbon atoms in the general formulae (III), (IV) and (V) representing the phenylenediamine dimer of the invention, include an alkyl group having from 1 to 6 carbon atom(s), an alkoxy group, a styryl group and the like.

Examples of the aryl group having from 6 to 24 nucleus carbon atoms include a phenyl group, a biphenyl group, a naphthyl group, an anthranyl group, a terphenyl group, a pyrenyl group and the like, and a phenyl group and a naphthyl group are preferred.

Examples of the alkyl group having from 1 to 6 carbon atom(s) include methyl, ethyl, n-propyl, i-propyl, n-butyl, s-butyl, t-butyl, n-pentyl, n-hexyl and the like.

Examples of the alkoxy group having from 1 to 6 carbon atom(s) include methoxy, ethoxy, n-propyloxy, i-propyloxy, n-butoxy, s-butoxy, t-butoxy, n-pentyloxy, n-hexyloxy groups and the like.

Examples of the styryl group include 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl groups and the like. In particular, a 2,2-diphenylvinyl-1-yl group is preferred.

X in the general formula (III), Y in the general formula (IV) and Y in the general formula (V) each is a linking group, which is a single bond, arylene having from 6 to 24 nucleus carbon atoms, alkylene having from 1 to 6 carbon atoms, diphenylmethylene, an ether bond, a thioether bond, an aromatic heterocyclic ring or a substituted or unsubstituted vinyl bond.

Examples of the arylene having from 6 to 24 nucleus carbon atoms include phenylene, biphenylene, naphtylene, anthranylene, terphenylene, pyrenylene and the like.

Examples of the alkylene having from 1 to 6 carbon atom(s) include methylene, isopropylene, cyclopropylene and the like.

The diphenylmethylene may be substituted with the alkyl having from 1 to 6 carbon atom(s) or an alkoxy group.

Examples of the aromatic heterocyclic ring include pyrrole, furan, thiophene, schirole, triazine, oxadiazole, triazole, oxazole, quinoline, quinoxaline, pyrimidine and the like.

At least one of $Ar^{13}$ to $Ar^{18}$ in the general formula (III) represents an aryl group having from 10 to 24 nucleus carbon atoms, which is substituted with a styryl group, or one of $Ar^{15}$, $Ar^{18}$ and X is a condensed aromatic ring having from 10 to 24 nucleus carbon atoms, an aromatic heterocyclic ring or a substituted or unsubstituted vinyl group.

Examples of the condensed aromatic ring include naphthyl, anthranyl, pytenyl, phenanoryl and the like, and in particular, a naphthyl group is preferred.

Examples of the styryl group include 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl groups and the like. In particular, a 2,2-diphenylvinyl-1-yl group is preferred. Examples of the aromatic heterocyclic ring include pyrrole, furan, thiophene, schirole, triazine, oxadiazole, triazole, oxazole, quinoline, quinoxaline, pyrimidine and the like.

Preferred examples of the alkyl group as $R^7$ and $R^8$ include methylethyl, i-propyl, t-butyl and the like, and preferred examples of the alkoxy group include methoxy, ethoxy, i-propoxy, t-butoxy and the like.

In the case where X is a single bond, it is preferred that $R^7$ and $R^8$ are bonded to form a divalent group comprising substituted or unsubstituted fluorene.

At least one of $Ar^{19}$ to $Ar^{24}$ in the general formula (IV) represents an aryl group having from 10 to 24 nucleus carbon atoms, which is substituted with a styryl group, or one of $Ar^{19}$ to $Ar^{24}$ and Y is a condensed aromatic ring having from 10 to 24 nucleus carbon atoms, an aromatic heterocyclic ring or a substituted or unsubstituted vinyl group.

Examples of the condensed aromatic ring include naphthyl, anthranyl, pyrenyl, phenanthryl and the like, and in particular, a naphthyl group is preferred.

Examples of the styryl group include 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl groups and the like. In particular, a 2,2-diphenylvinyl-1-yl group is preferred.

Examples of the aromatic heterocyclic ring include pyrrole, furan, thiophene, schirole, triazine, oxadiazole, triazole, oxazole, quinoline, quinoxaline, pyrimidine and the like.

Preferred examples of the alkyl group as $R^9$ and $R^{10}$ include methylethyl, i-propyl, t-butyl and the like, and preferred examples of the alkoxy group include methoxy, ethoxy, i-propoxy, t-butoxy and the like.

In the case where Y is a single bond, it is preferred that $R^9$ and $R^{10}$ are bonded to form a divalent group comprising substituted or unsubstituted fluorene.

At least one of $Ar^{25}$ to $Ar^{30}$ in the general formula (V) represents an aryl group having from 10 to 24 nucleus carbon atoms, which is substituted with a styryl group, or one of $Ar^{25}$ to $Ar^{30}$ and Y is a condensed aromatic ring having from 10 to 24 nucleus carbon atoms, an aromatic heterocyclic ring or a substituted or unsubstituted vinyl group.

Examples of the condensed aromatic ring include naphthyl, anthranyl, pyrenyl, phenanthryl and the like, and in particular, a naphthyl group is preferred.

Examples of the styryl group include 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl groups and the like. In particular, a 2,2-diphenylvinyl-1-yl group is preferred.

Examples of the aromatic heterocyclic ring include pyrrole, furan, thiophene, schirole, triazine, oxadiazole, triazole, oxazole, quinoline, quinoxaline, pyrimidine and the like.

Preferred examples of the alkyl group as $R^{11}$ and $R^{12}$ include methylethyl, i-propyl, t-butyl and the like, and preferred examples of the alkoxy group include methoxy, ethoxy, i-propoxy, t-butoxy and the like.

In the case where Y is a single bond, it is preferred that $R^{11}$ and $R^{12}$ are bonded to form a divalent group comprising substituted or unsubstituted fluorene.

Specific examples of the phenylenediamine dimer represented by the general formula (III) include compound shown by the following chemical formulae (PD-01') to (PD-56'). The invention is not limited to them.

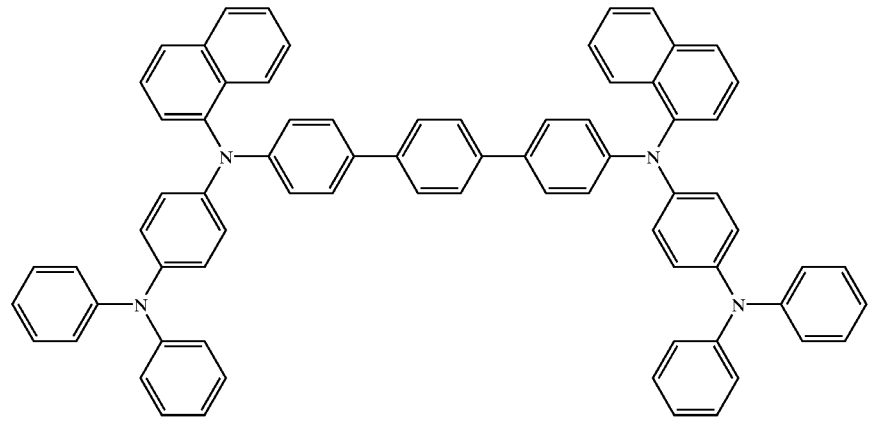

PD-01'

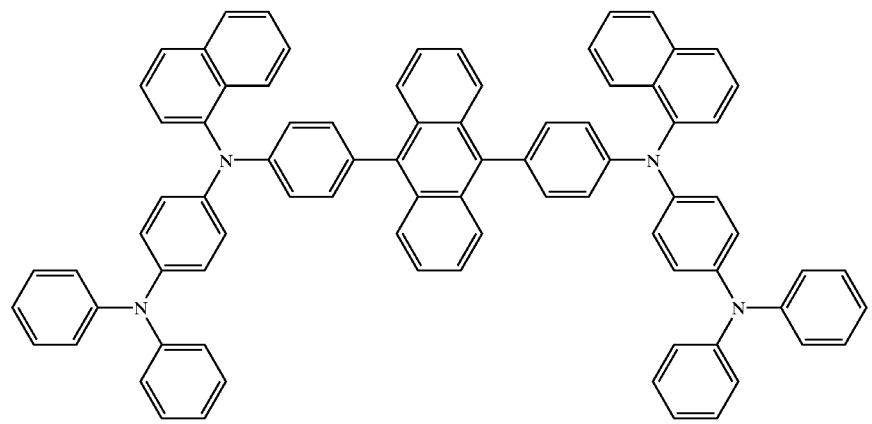

PD-02'

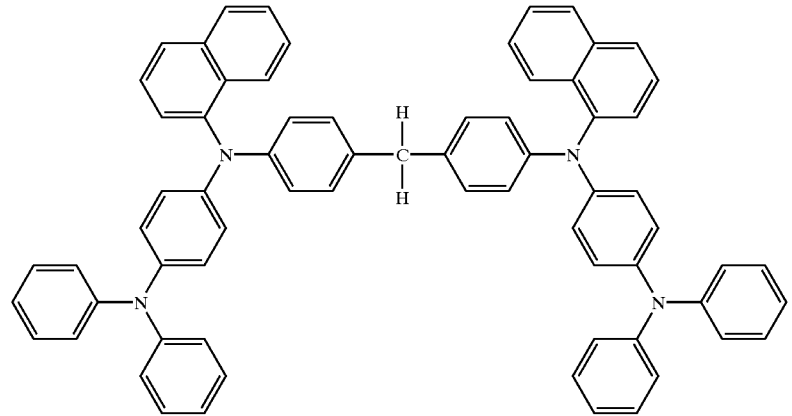

PD-03'

-continued
PD-04'
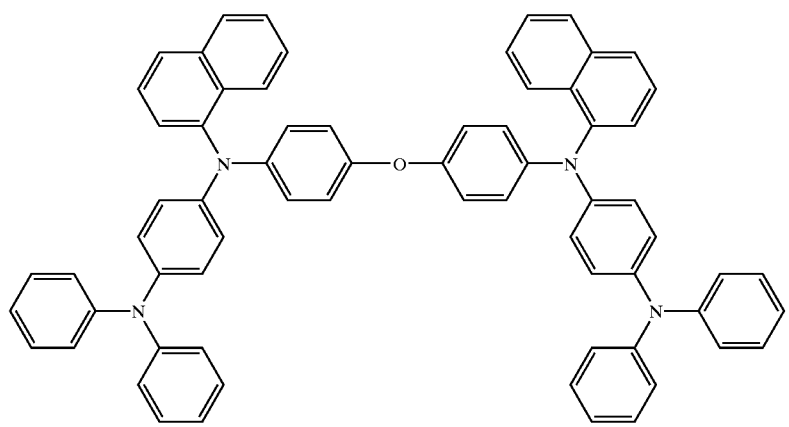
PD-05'
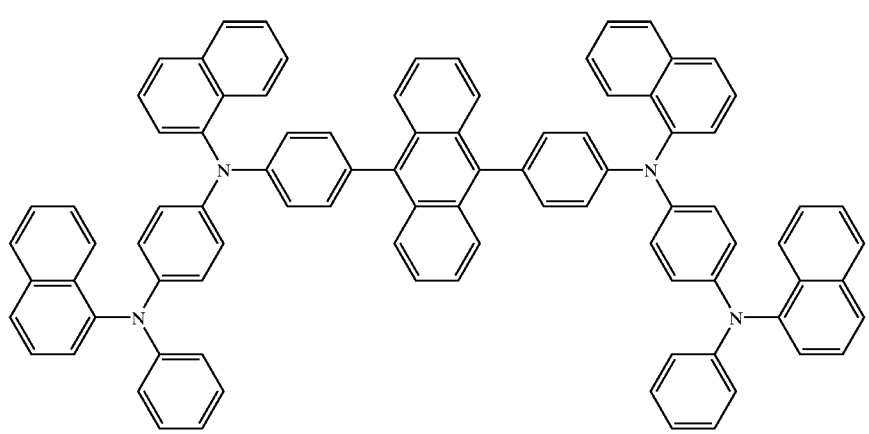
PD-06'
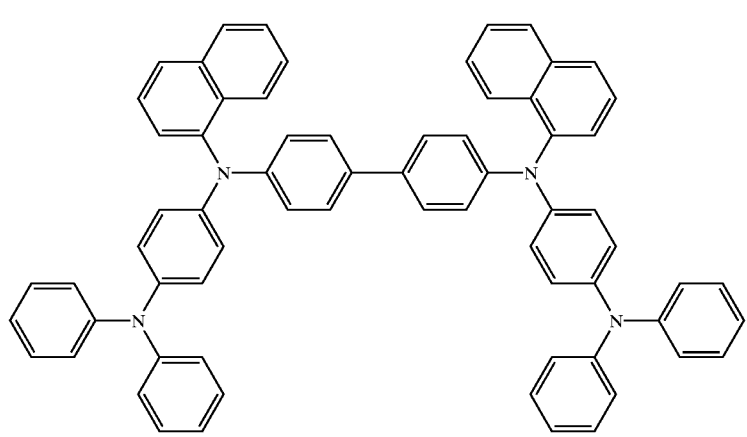
PD-07'
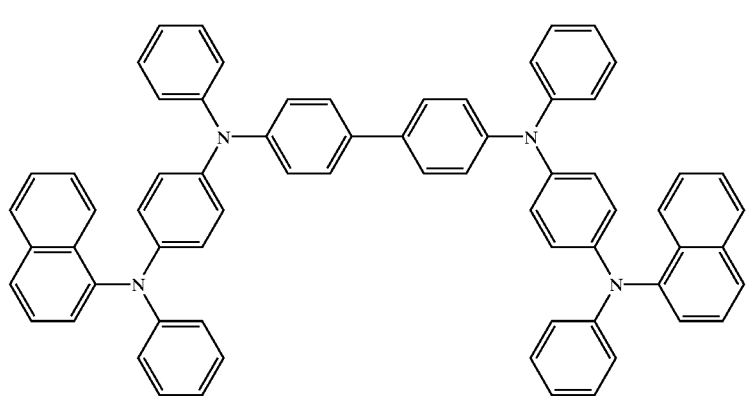

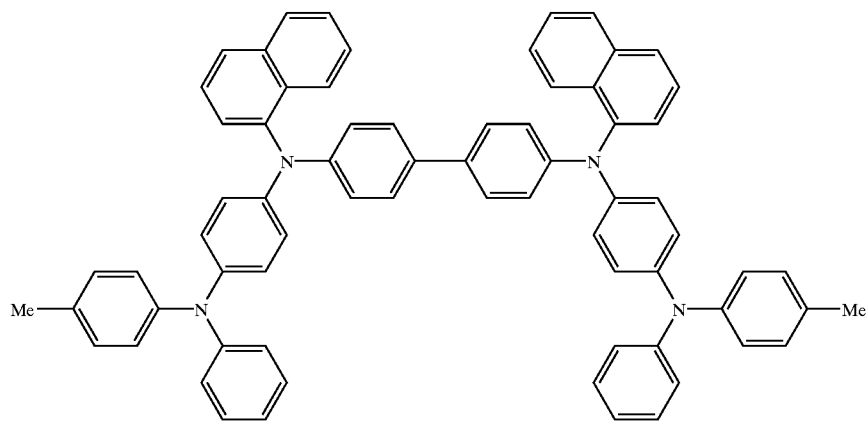
PD-08'
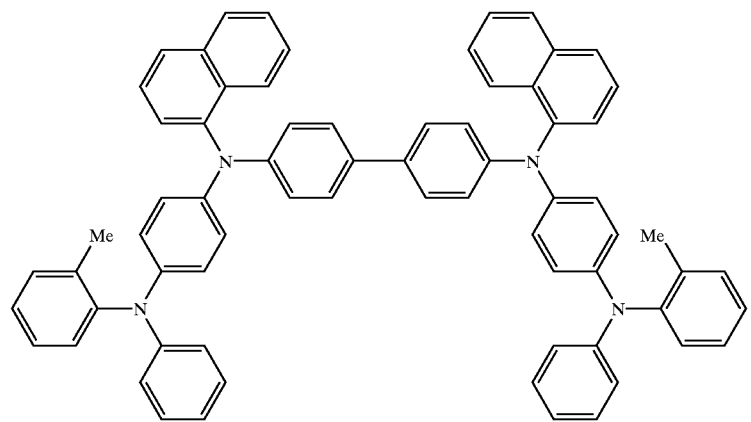
PD-09'
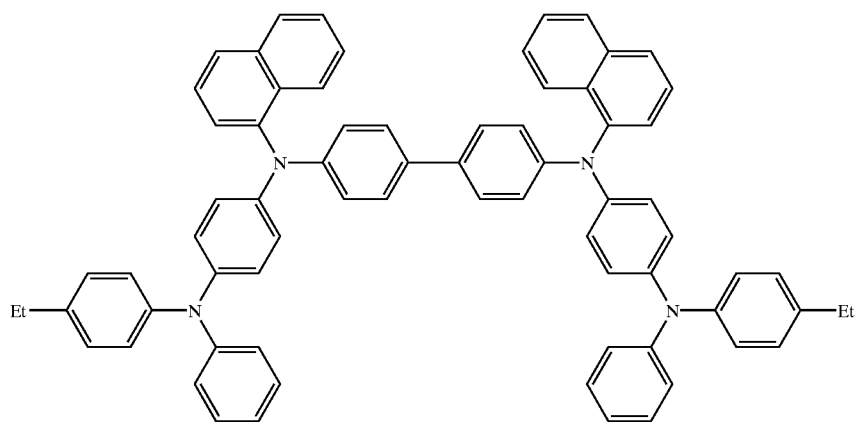
PD-10'

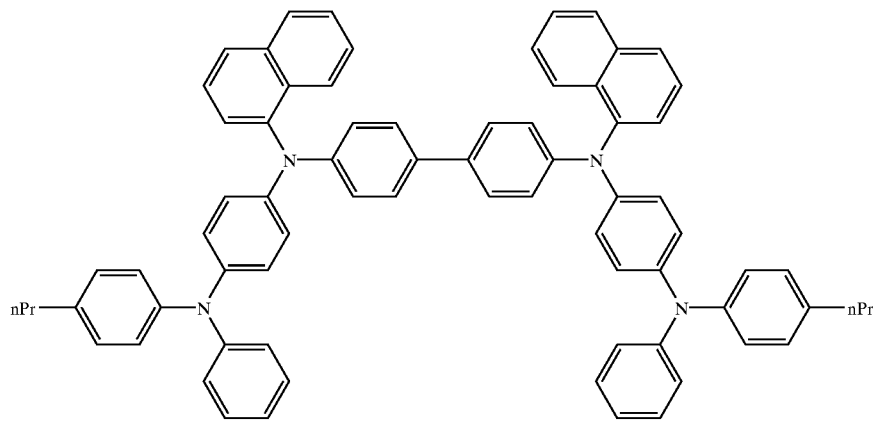
PD-11'
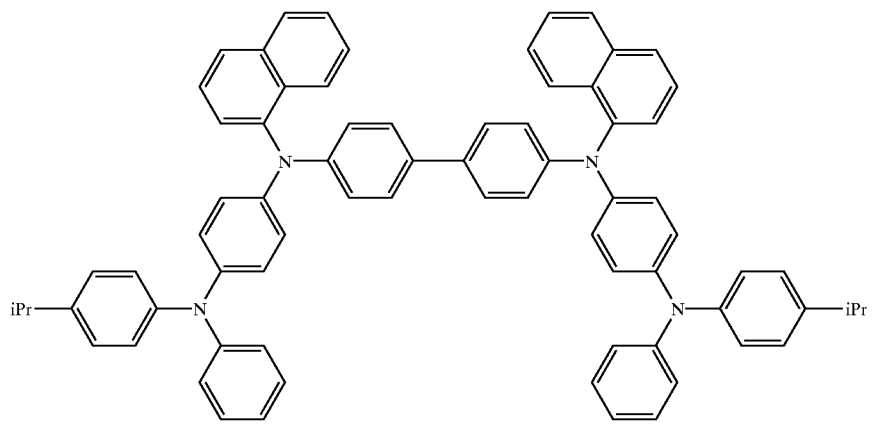
PD-12'
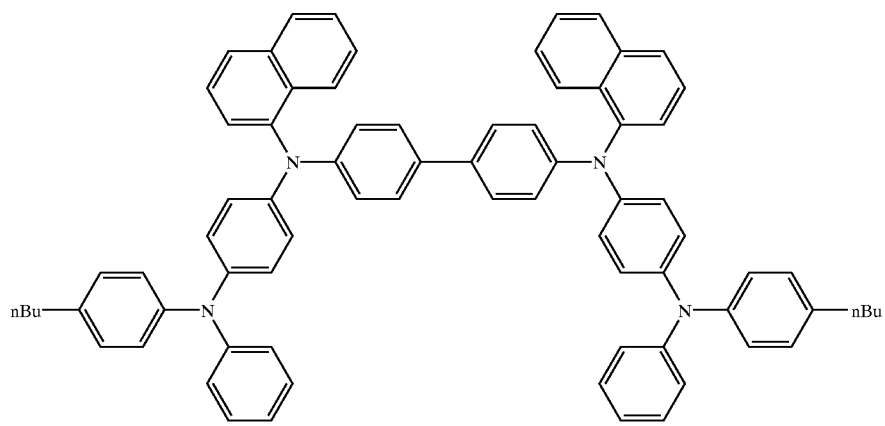
PD-13'

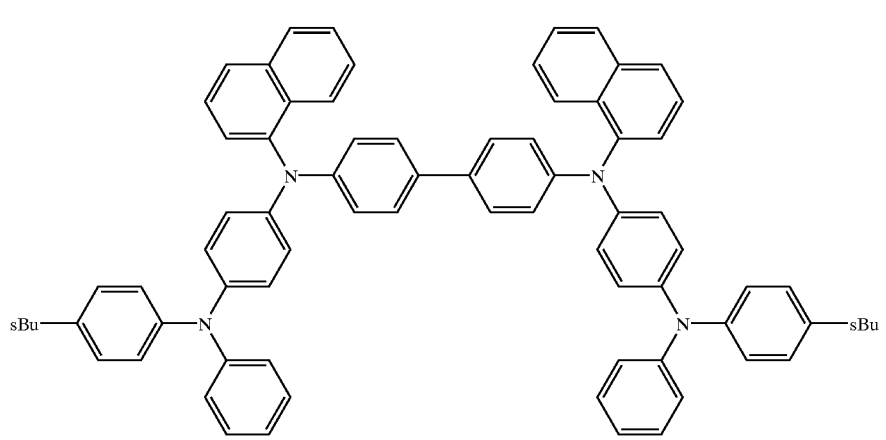
PD-14'
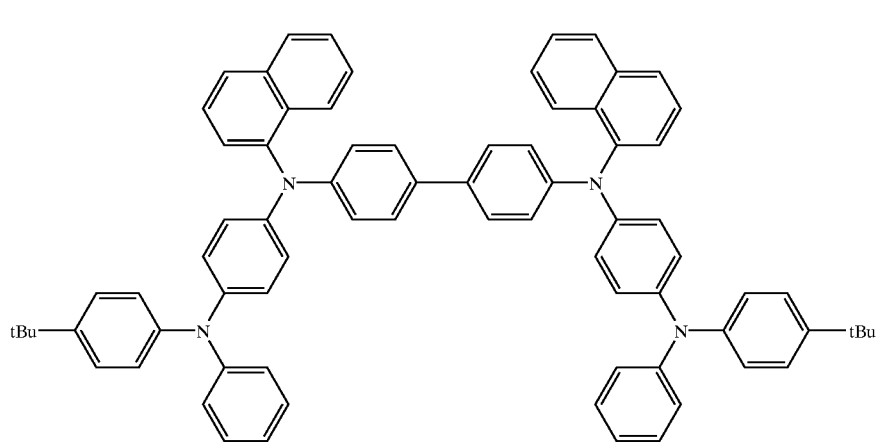
PD-15'
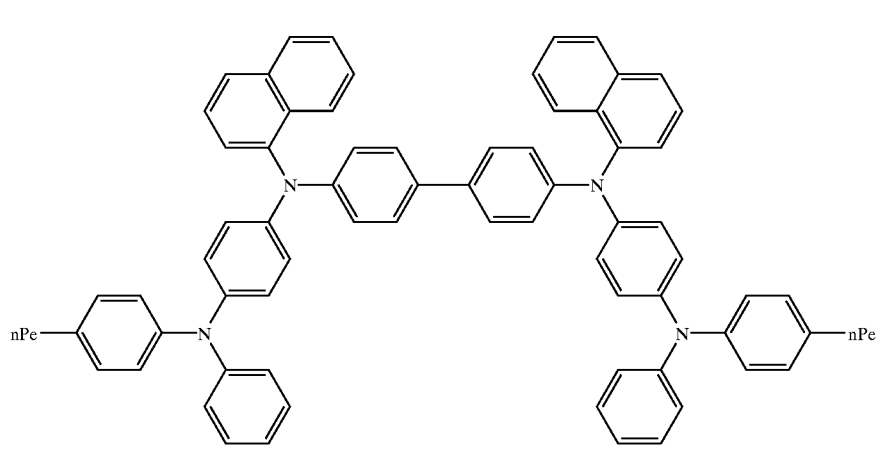
PD-16'

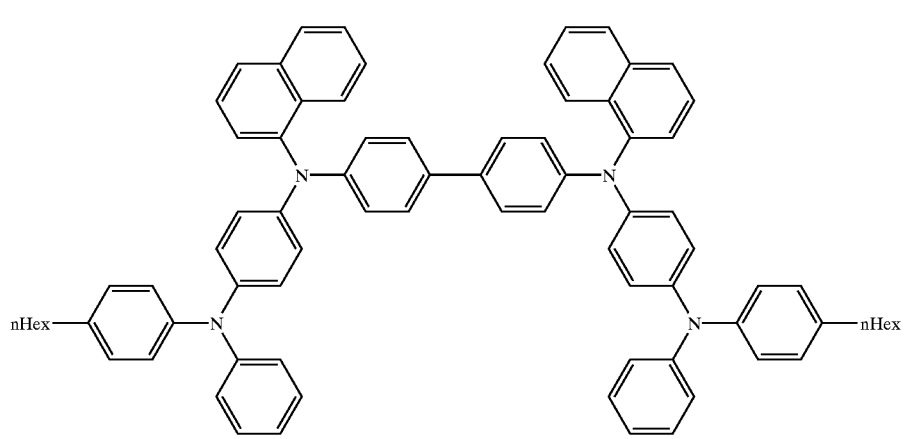
PD-17'
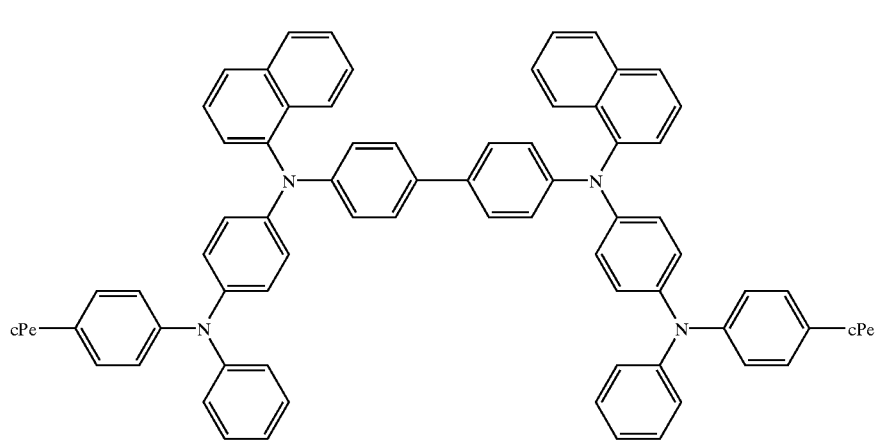
PD-18'
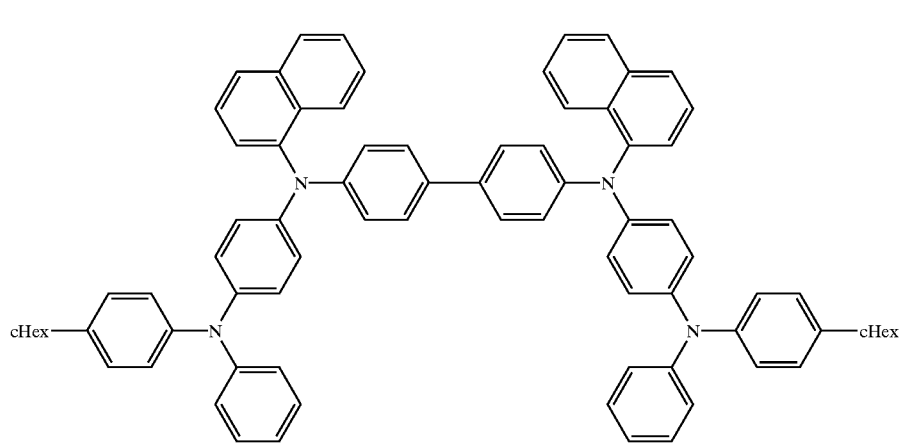
PD-19'

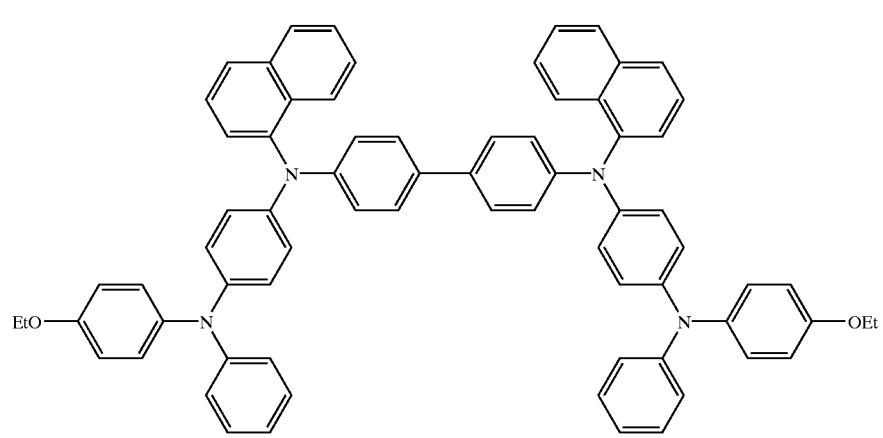
PD-20'
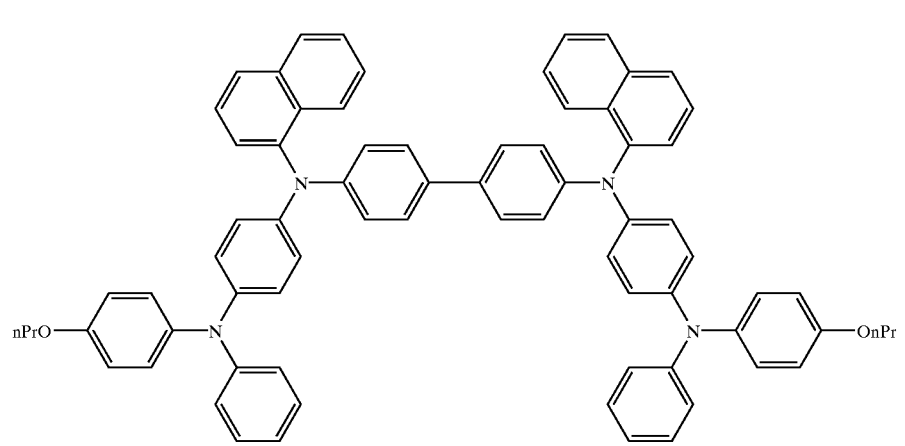
PD-21'
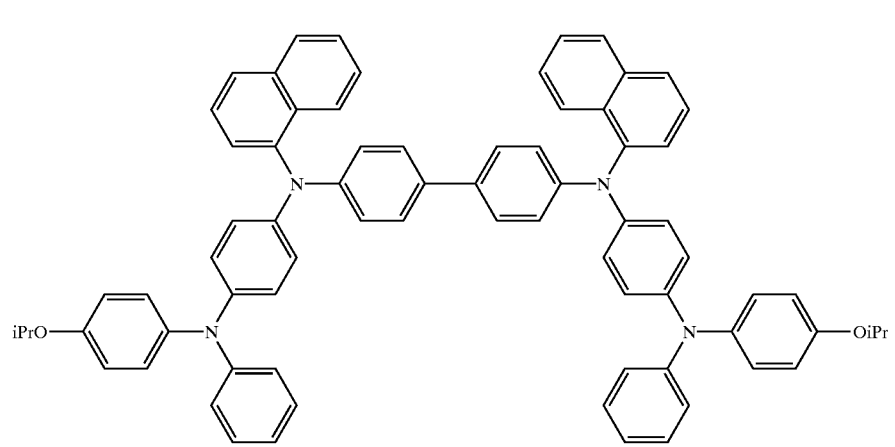
PD-22'

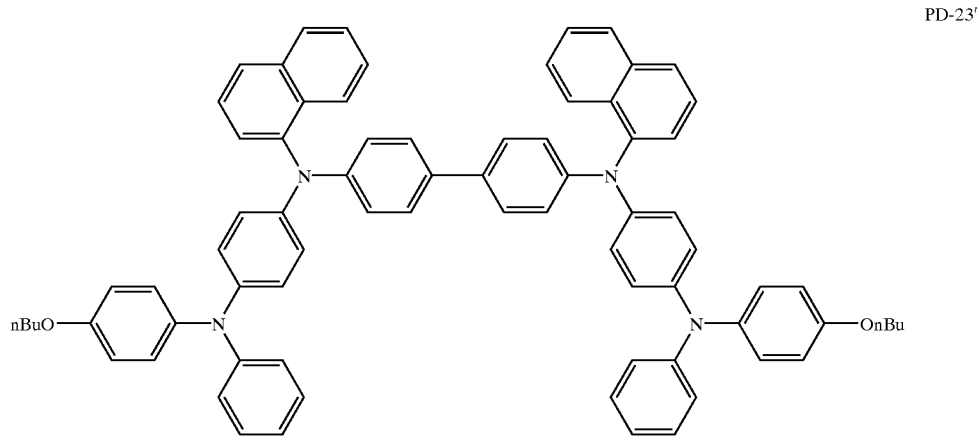
PD-23'
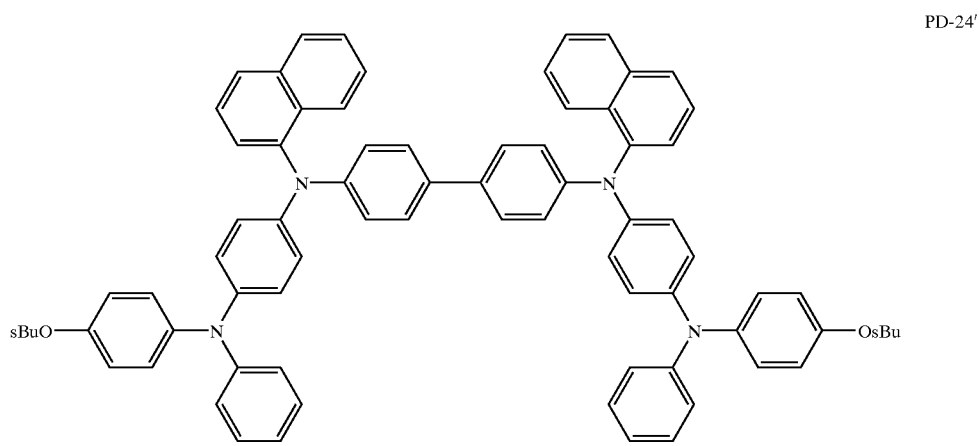
PD-24'
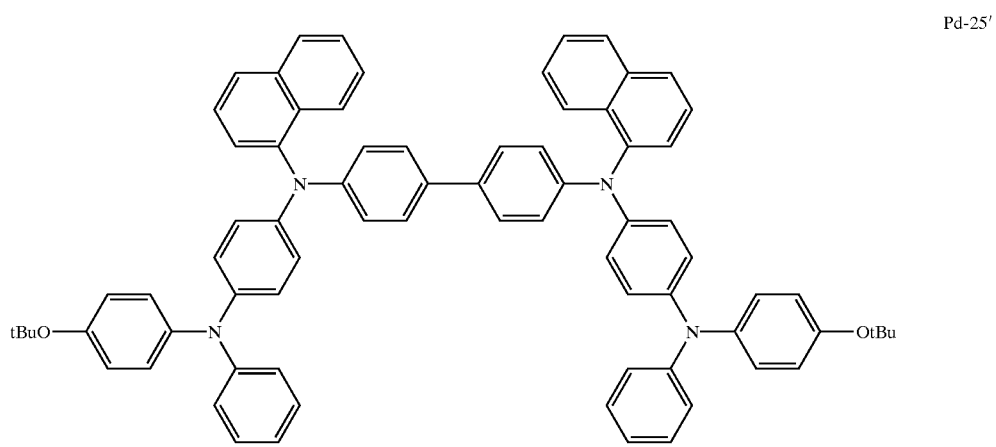
Pd-25'

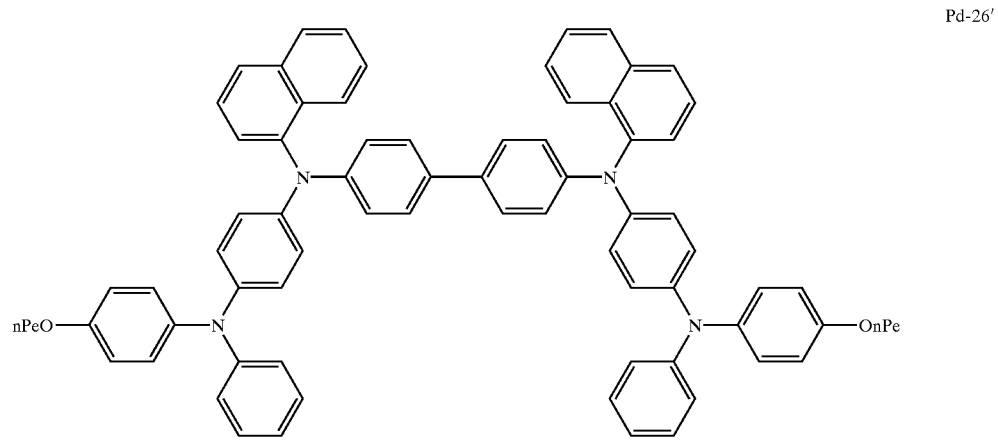
Pd-26'
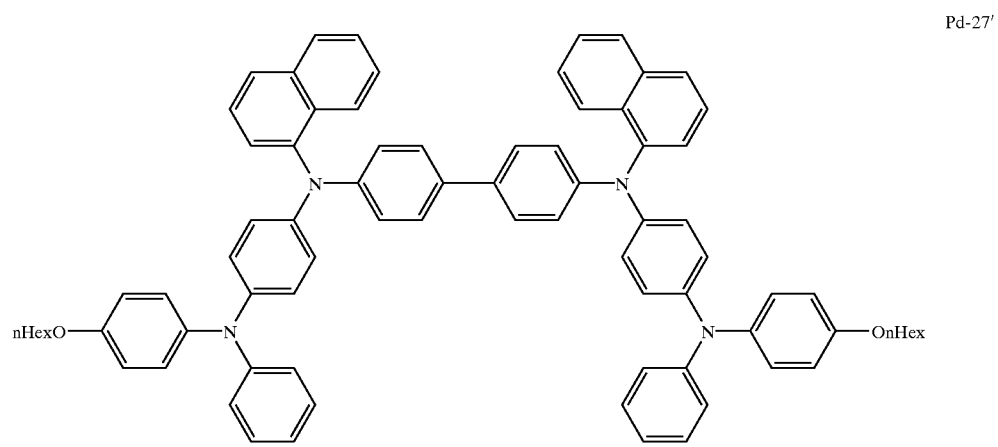
Pd-27'
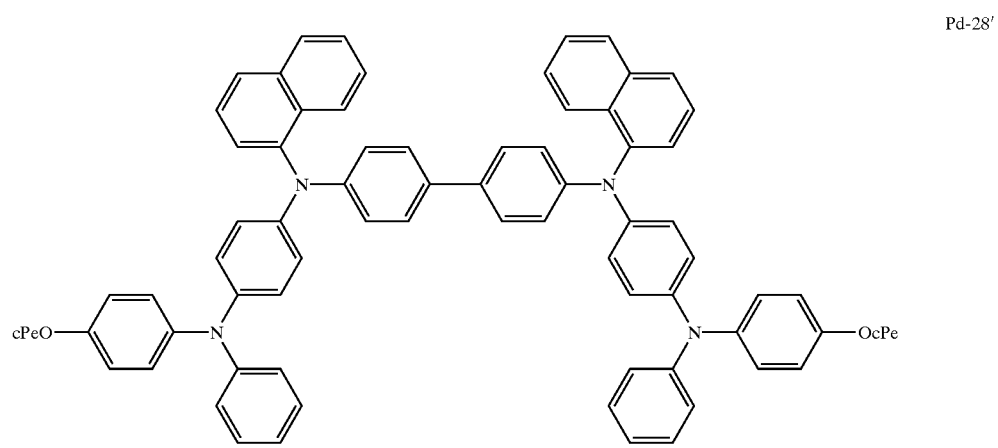
Pd-28'

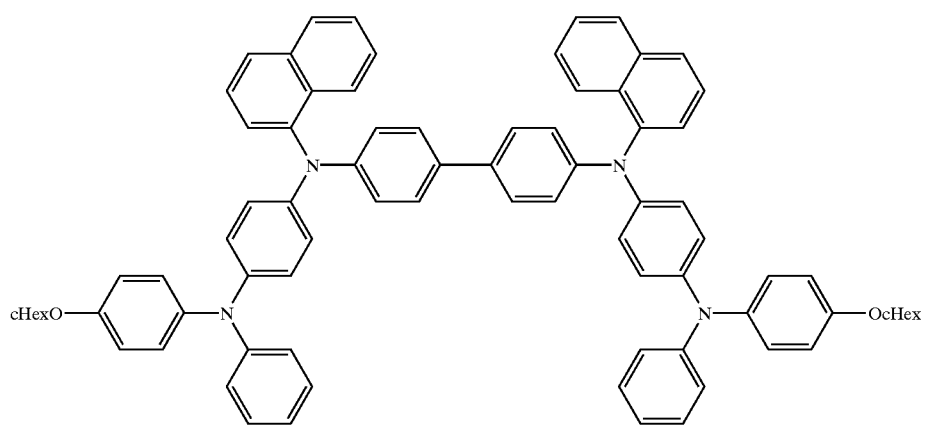
PD-29'
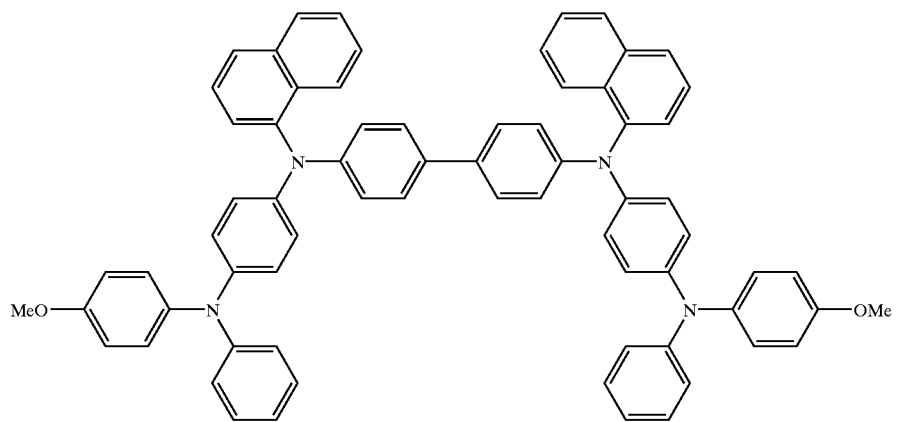
PD-30'
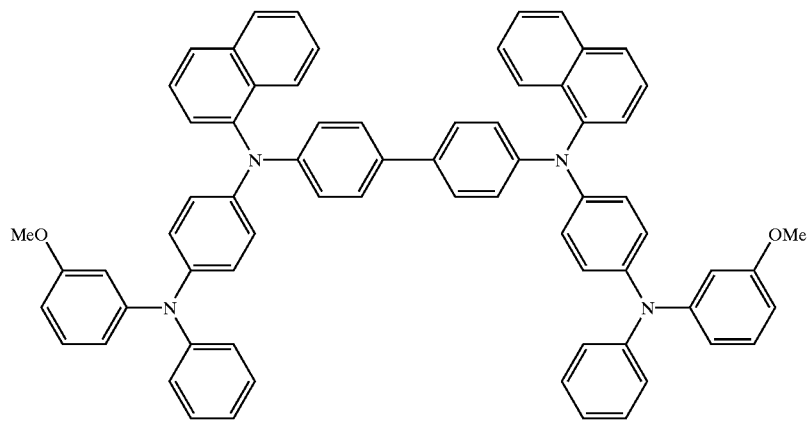
PD-31'

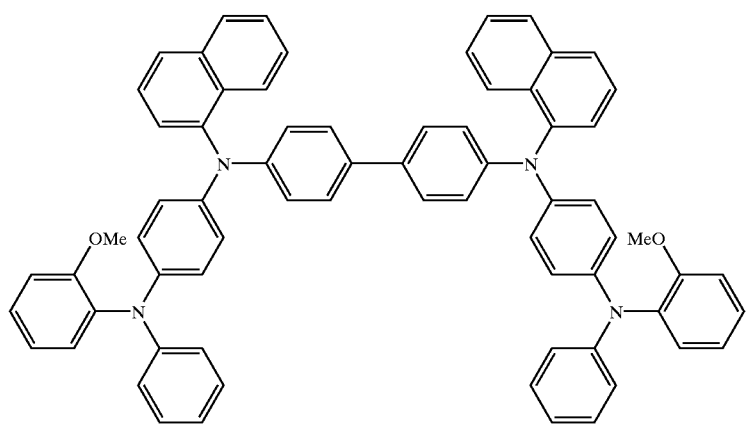
PD-32'
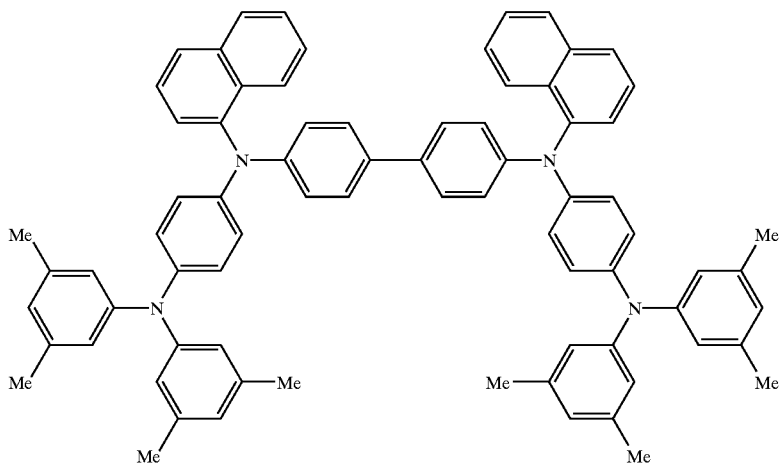
PD-33'
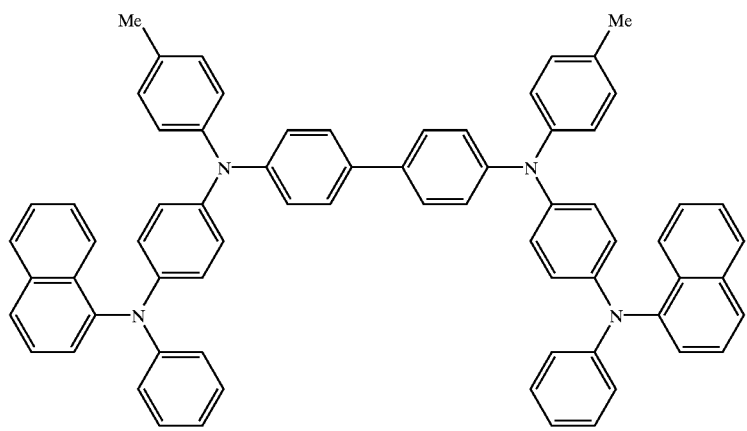

-continued
PD-35'
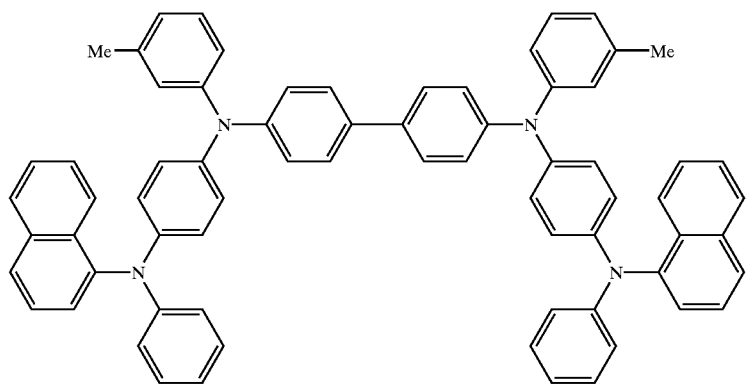
PD-36'
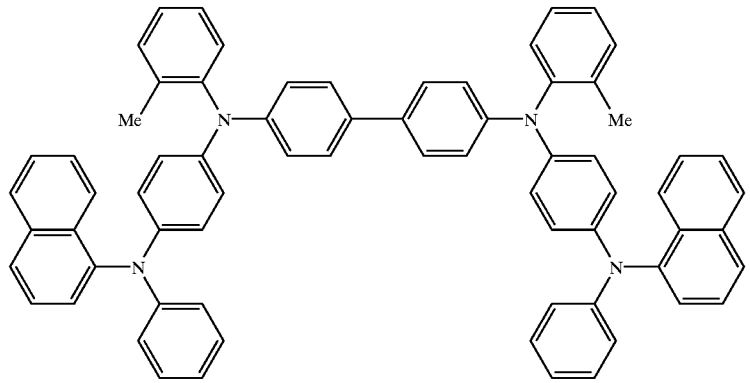
PD-37'
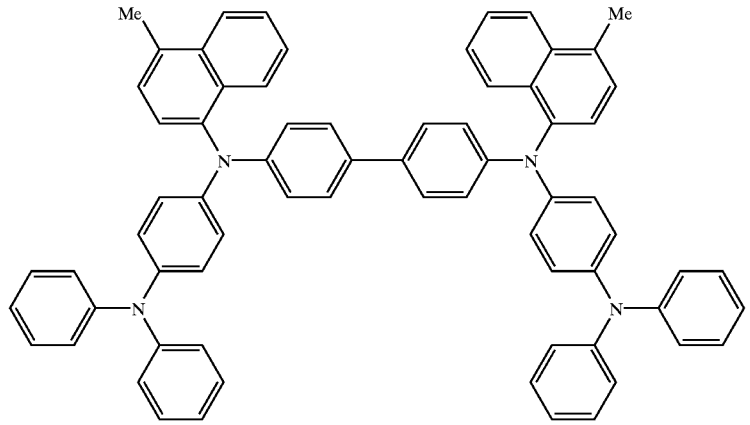
PD-38'
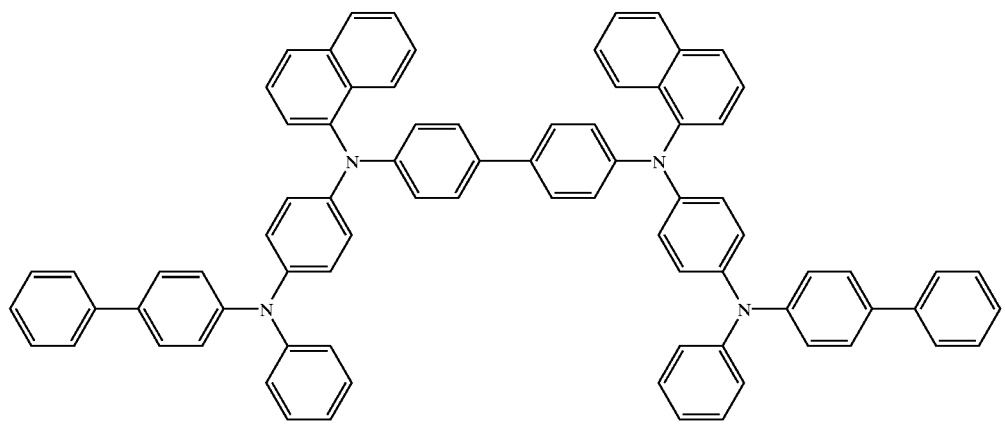

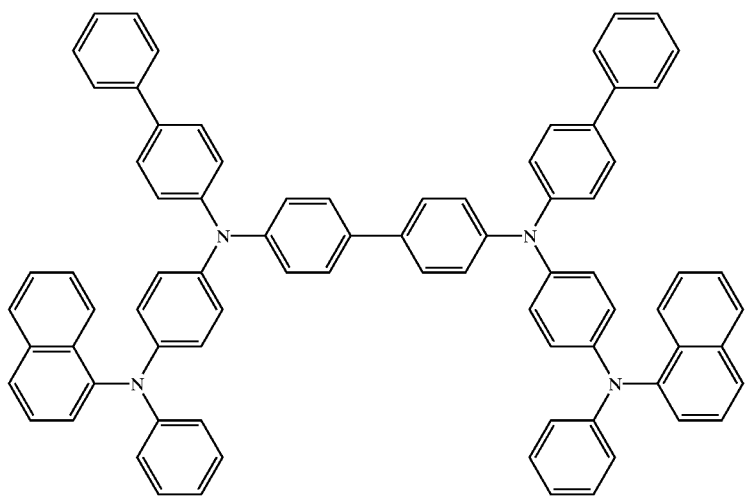
PD-39'
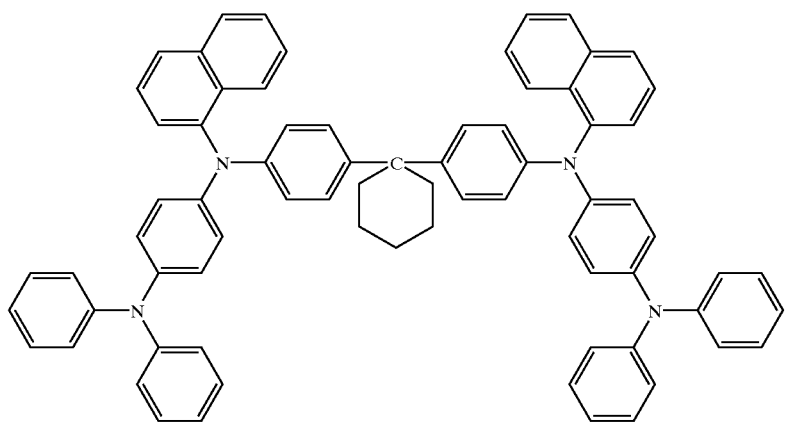
PD-40'
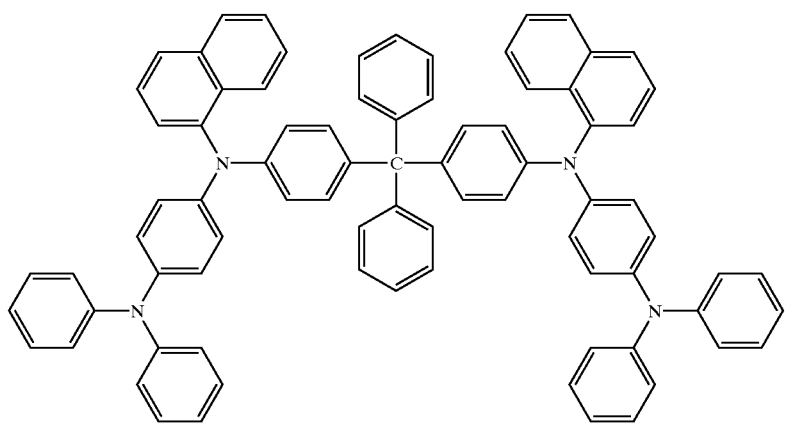
PD-41'

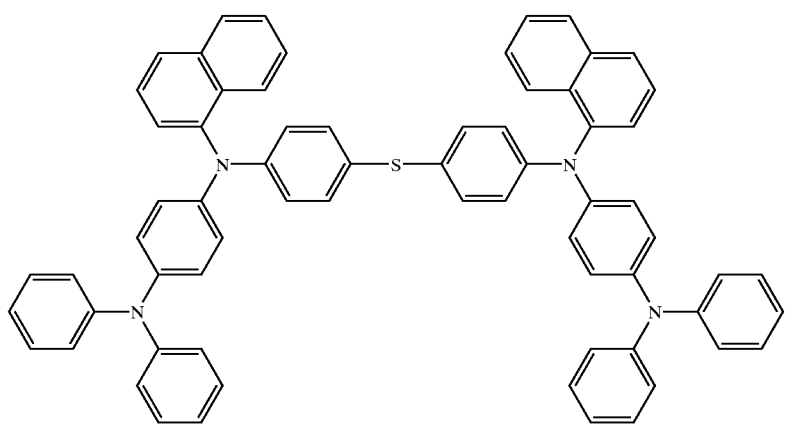
PD-42'
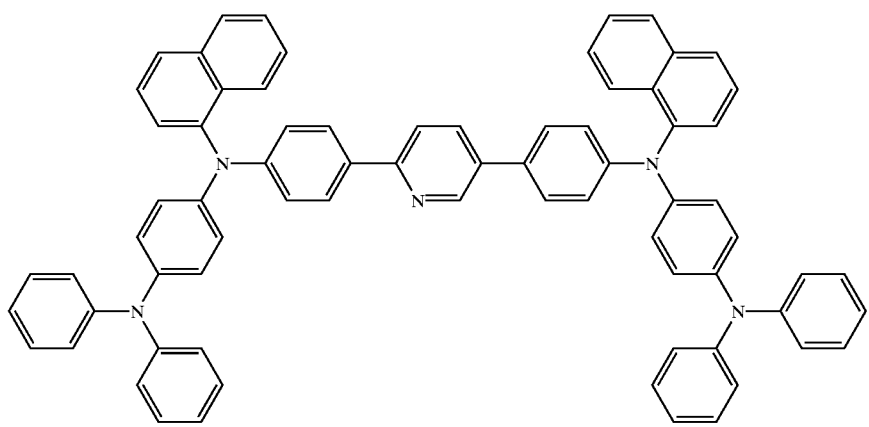
PD-43'
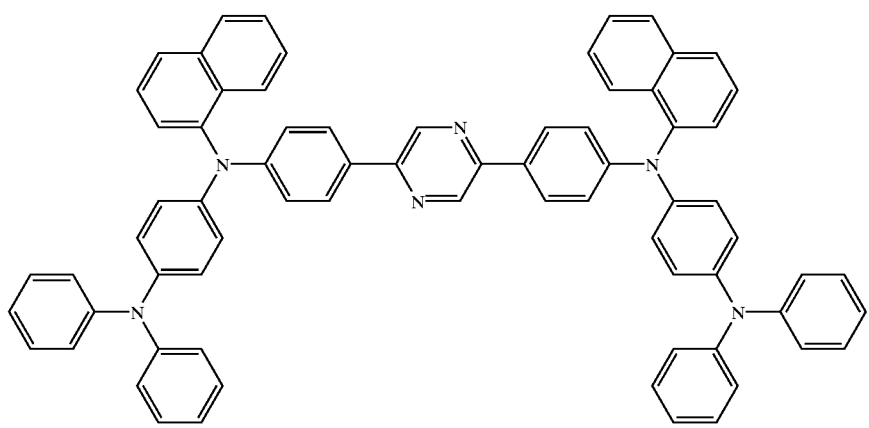
PD-44'

PD-45'
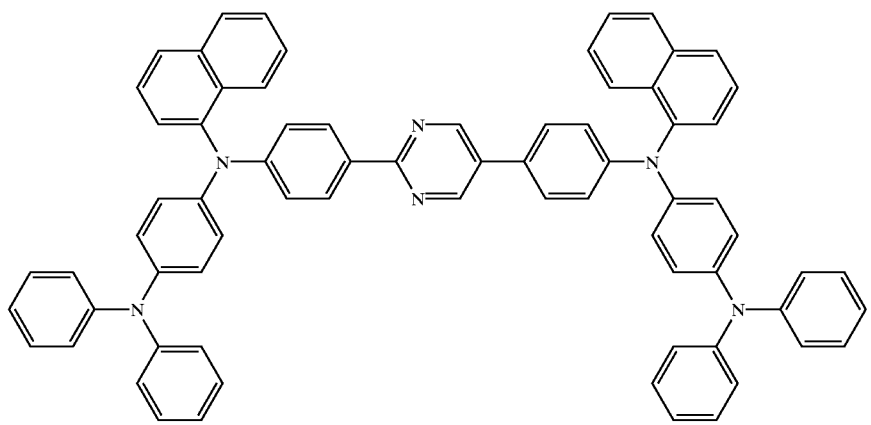
PD-46'
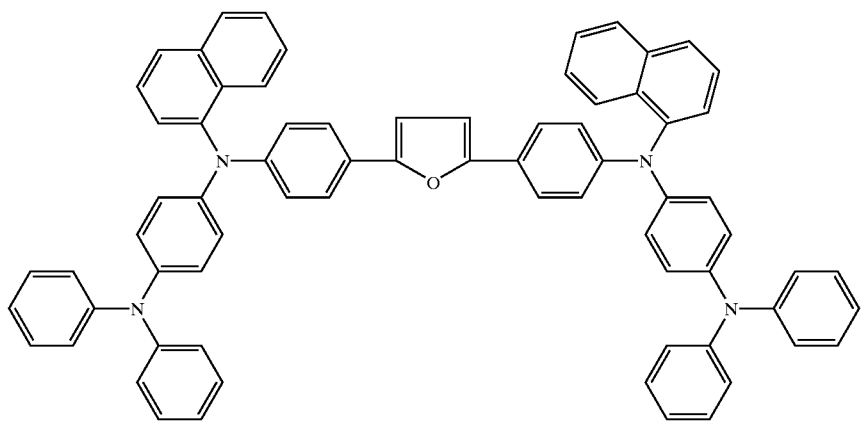
PD-47'
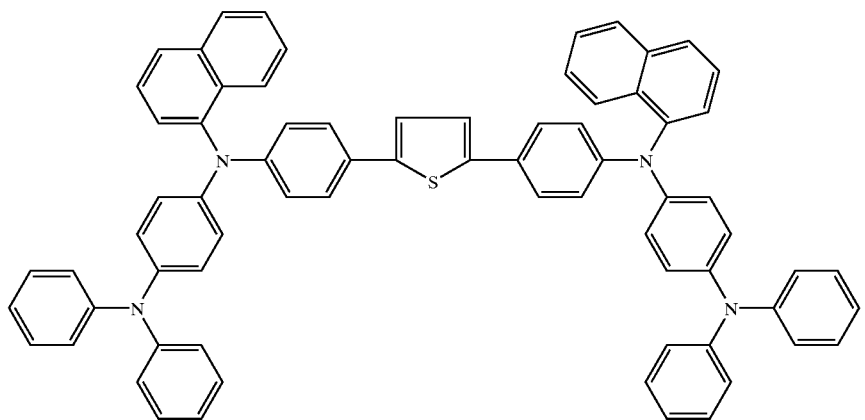

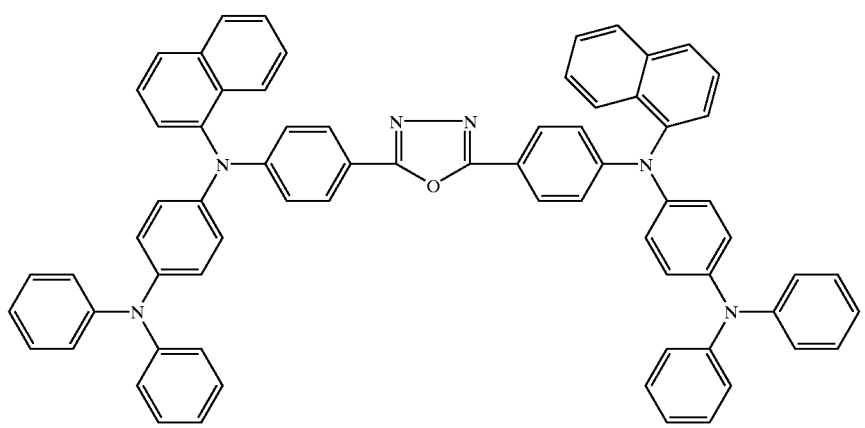
PD-48'
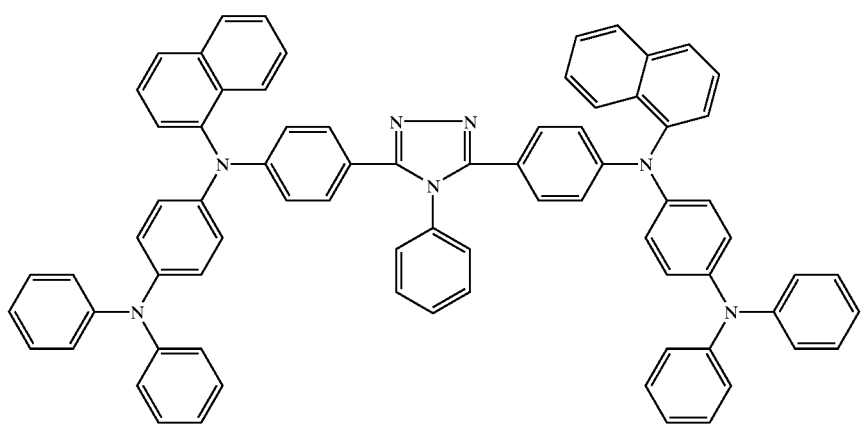
PD-49'
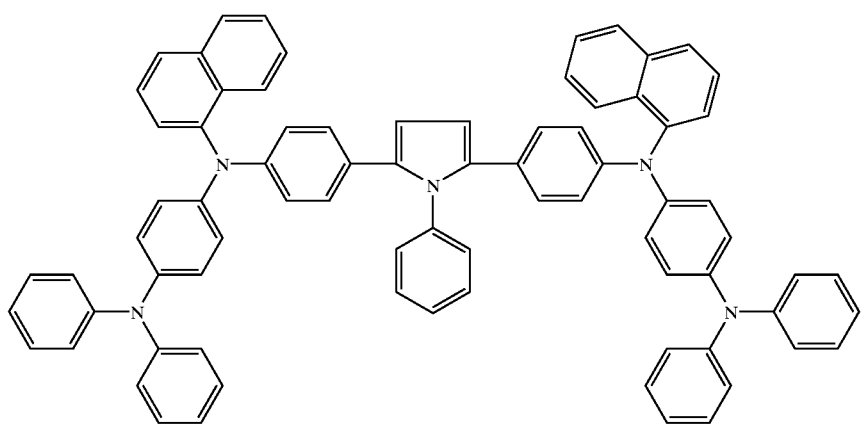
PD-50'

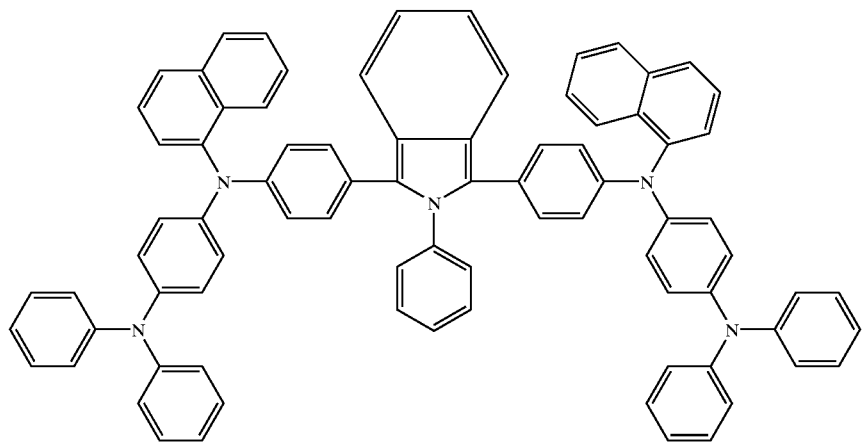
PD-51'
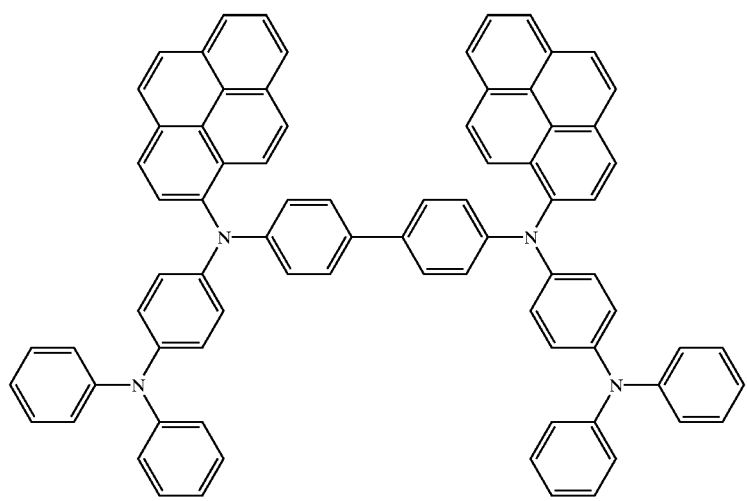
PD-52'
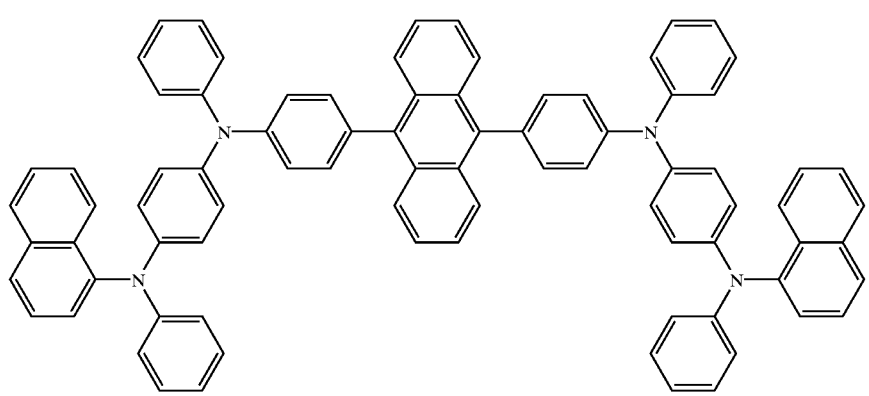
PD-53'

-continued

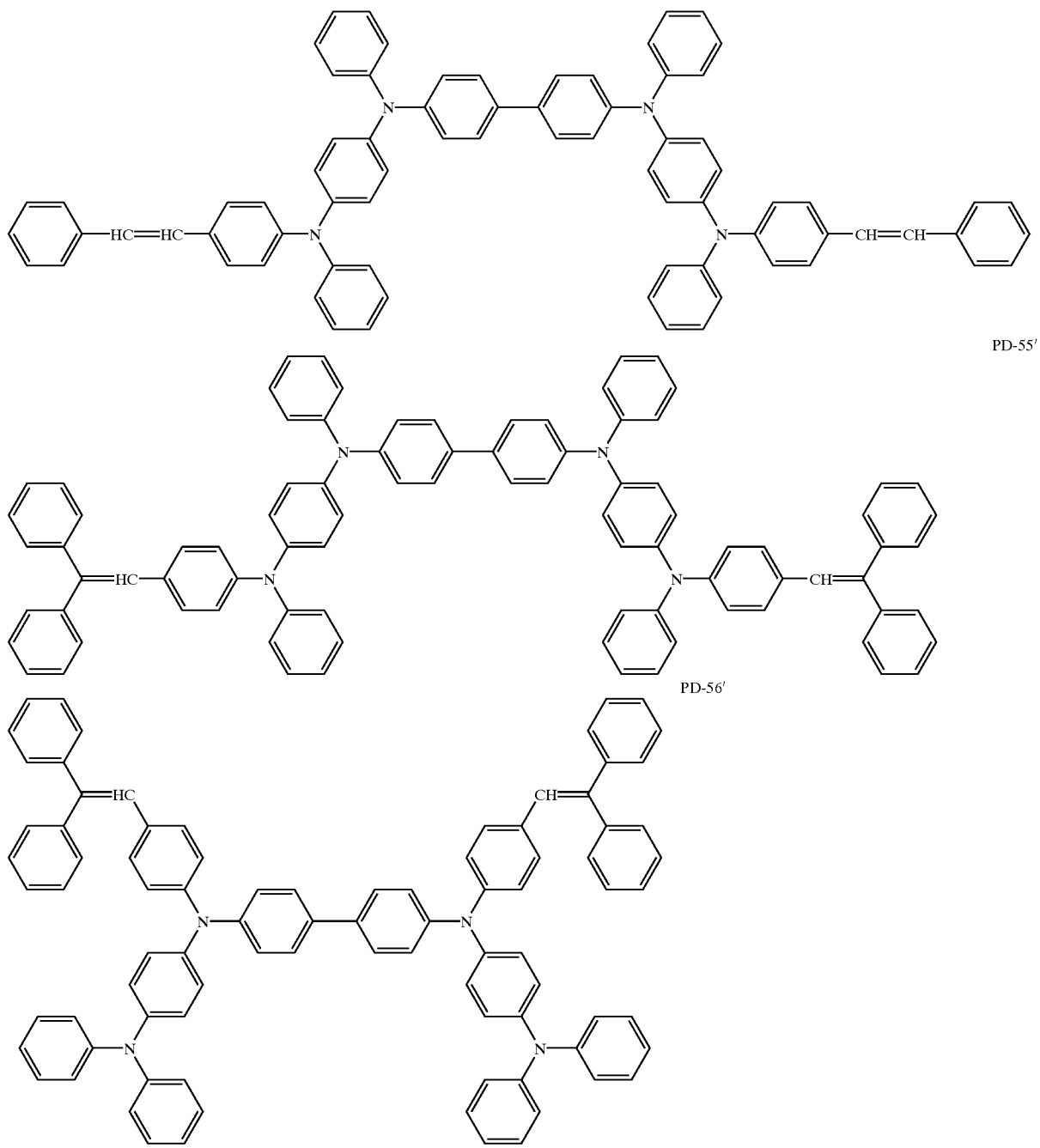

PD-54'

PD-55'

PD-56'

It has been found that the phenylenediamine derivative represented by the general formula (III) is particularly preferred among the derivatives represented by the general formula (I). That is, in comparison to the conventionally known ones disclosed in International Patent Publication WO98/30071, characteristics can be obtained that are not obtained by the conventional ones, i.e., (1) the compound having an aryl group containing a styryl group exhibits a long life time and high fluorescent property upon injection of an electron, and thus it can be used as a light emitting material., and (2) when an electron is injected to the compound where one of $Ar^{15}$, $Ar^{18}$ and the basic skeleton shown by the following chemical formula contains a condensed aromatic ring, an aromatic heterocyclic ring or a substituted or unsubstituted vinyl group, it is difficult to be degraded and the life time is long.

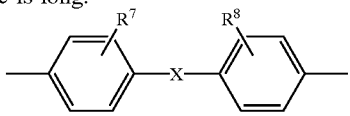

Specific examples of the phenylenediamine dimer represented by the general formula (IV) include compound shown by the following chemical formulae (PT-01') to (PT-11') and (PT-23') to (PT-31'). The invention is not limited to them.

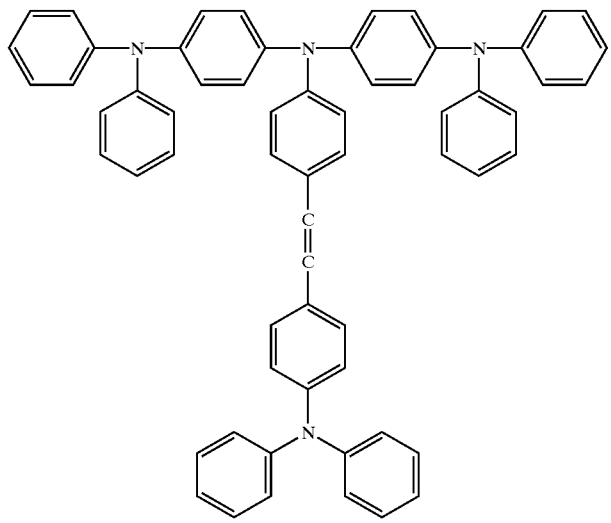
PT-01'
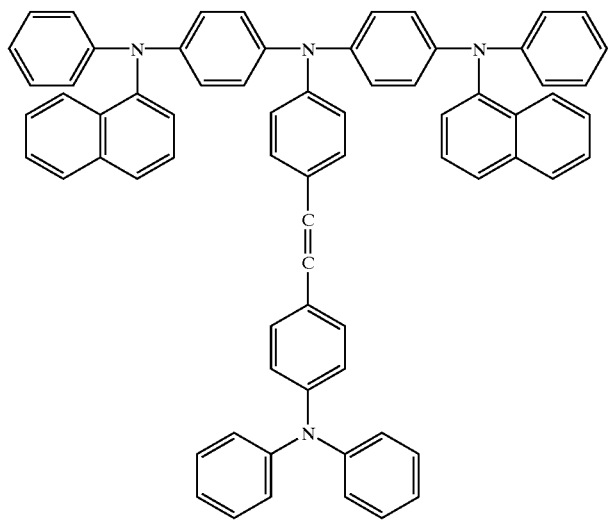
PT-02'
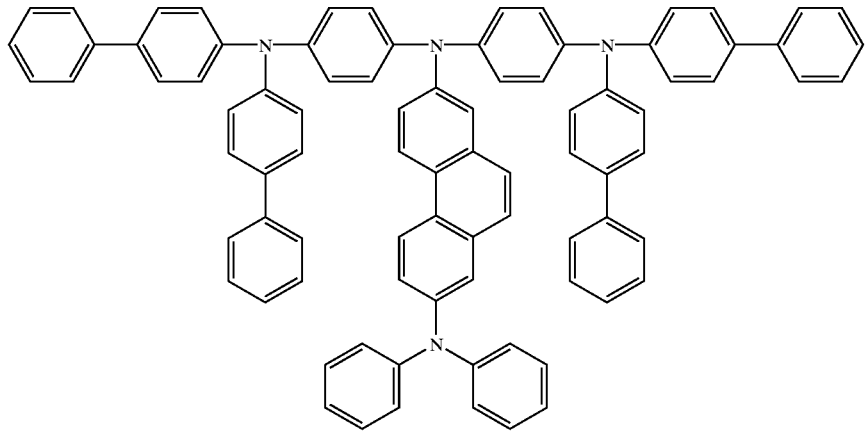
PT-03'

PT-04'
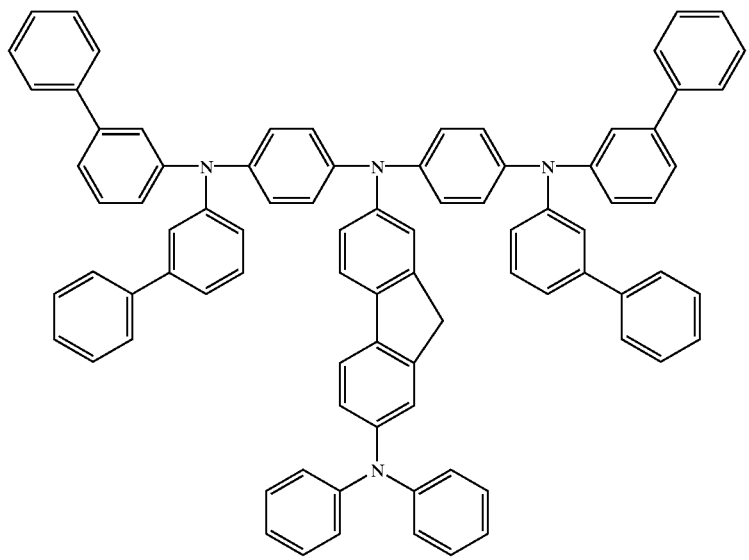
PT-05'
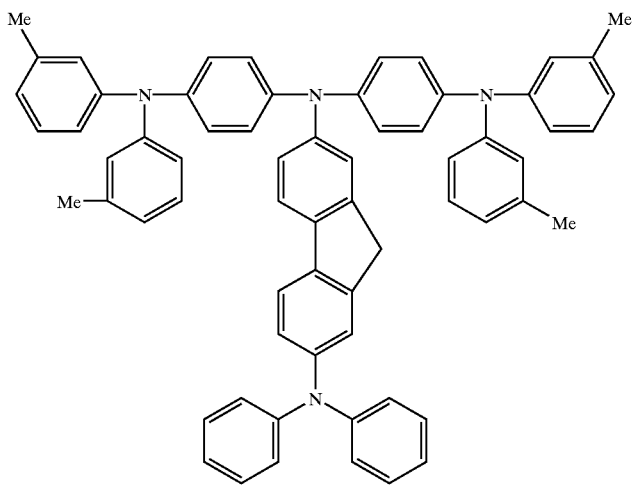
PT-06'
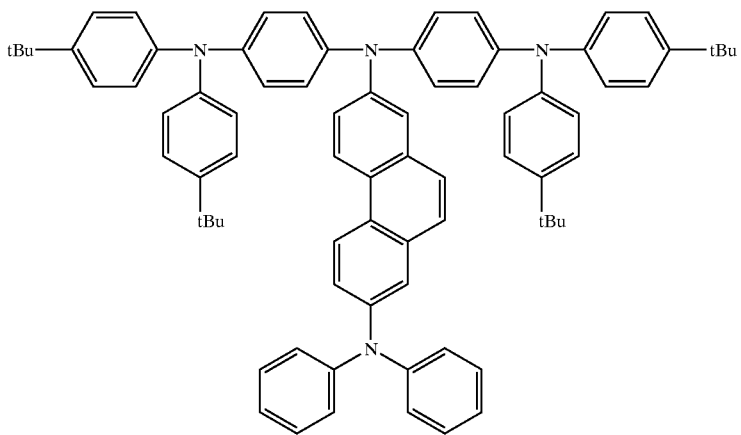

-continued
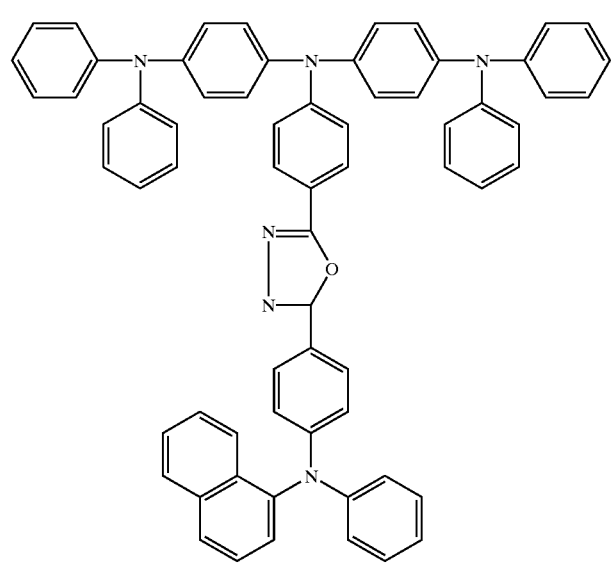
PT-07'
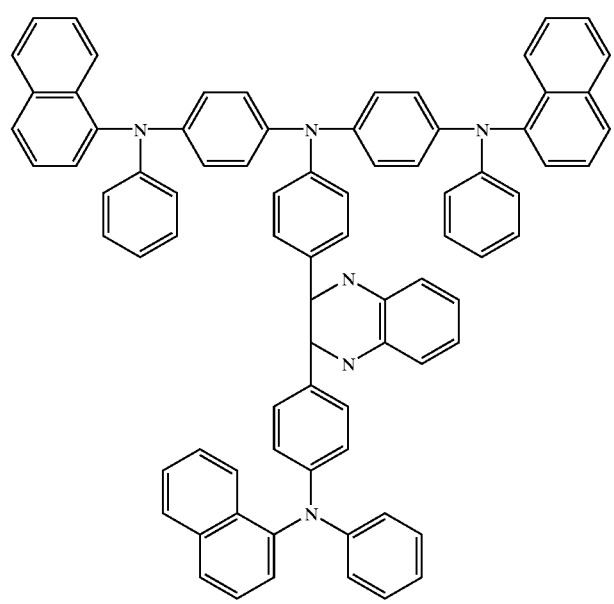
PT-08'

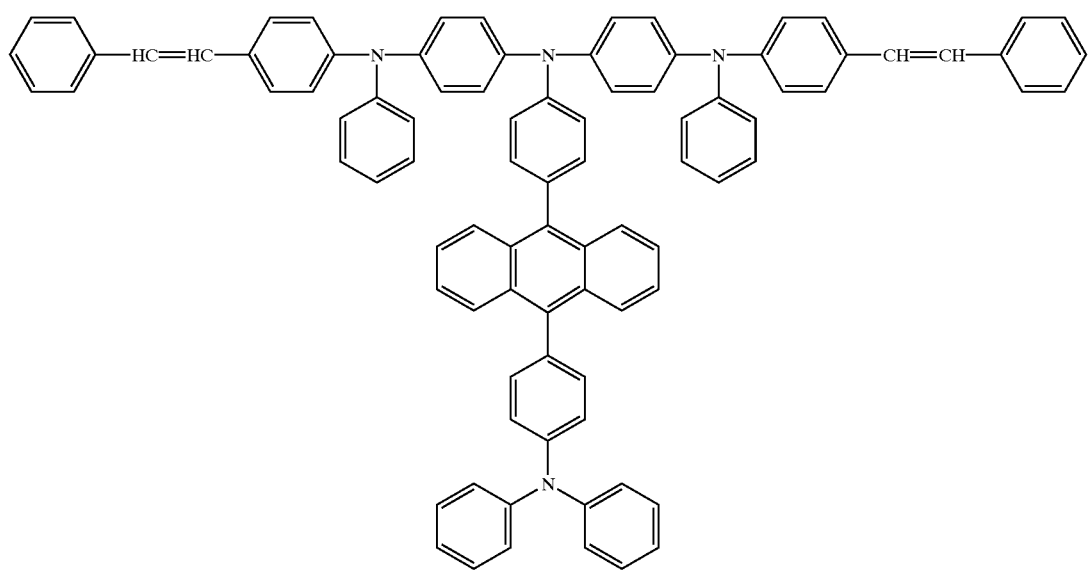
PT-09'
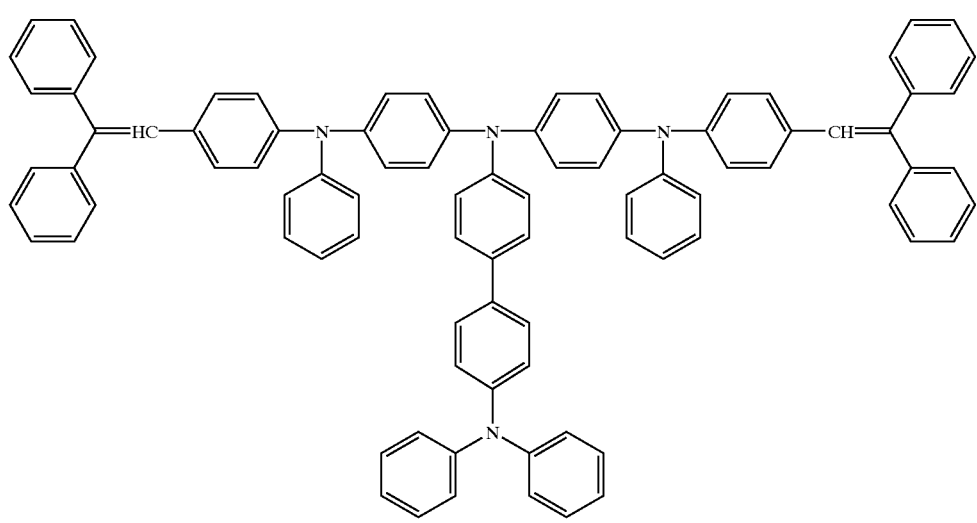
PT-10'
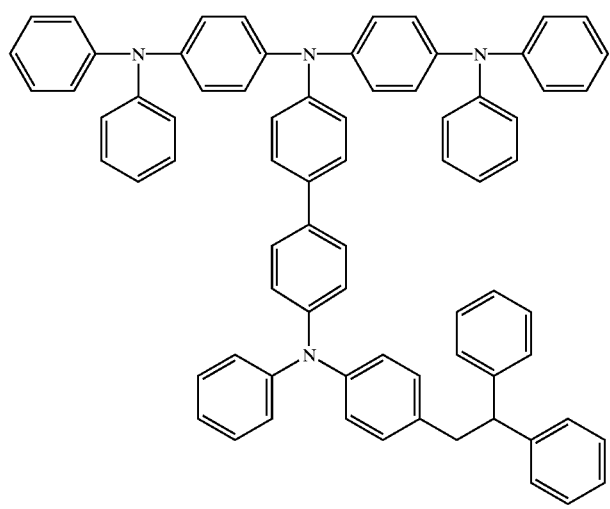
PT-11'

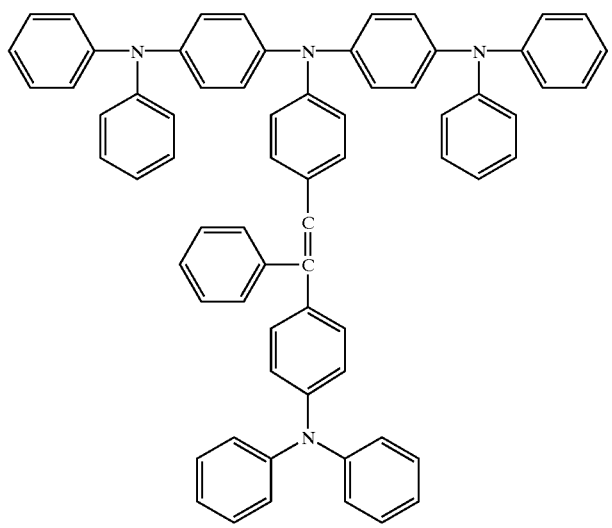
PT-23'
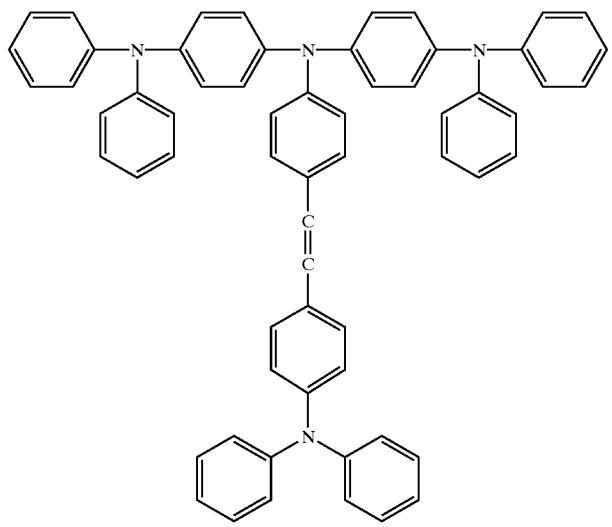
PT-24'
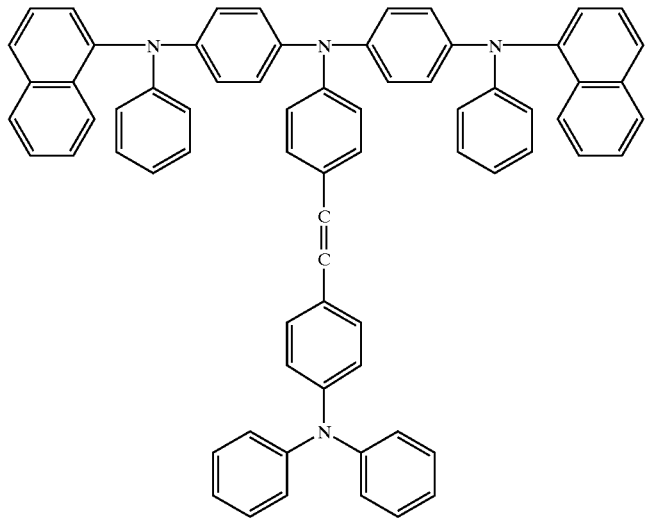
PT-25'

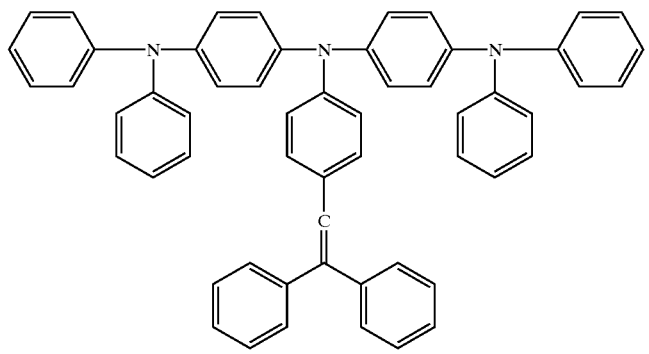
PT-26'
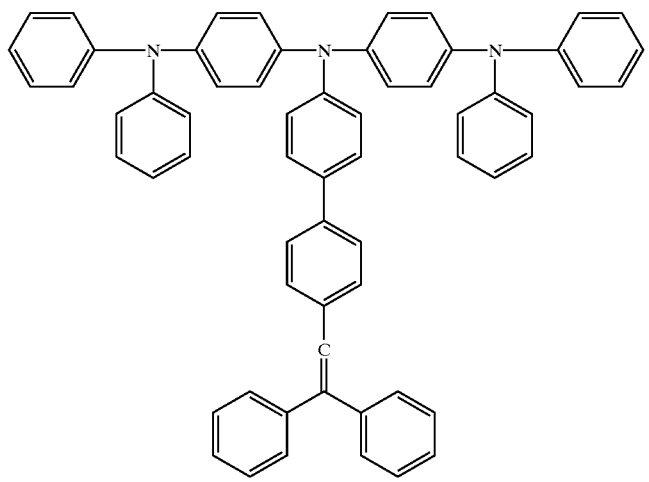
PT-27'
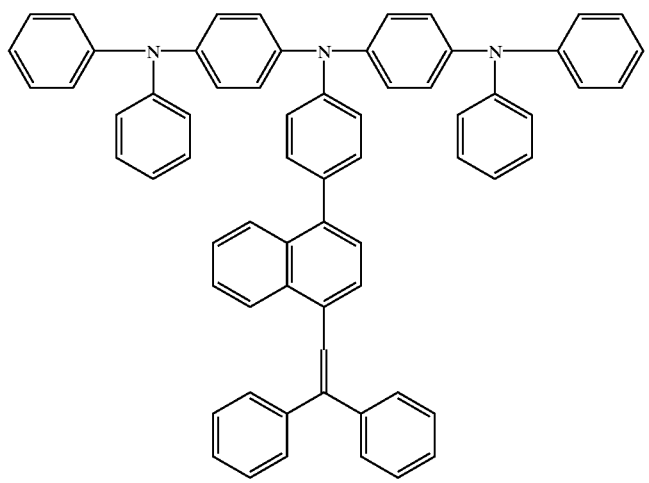
PT-28'

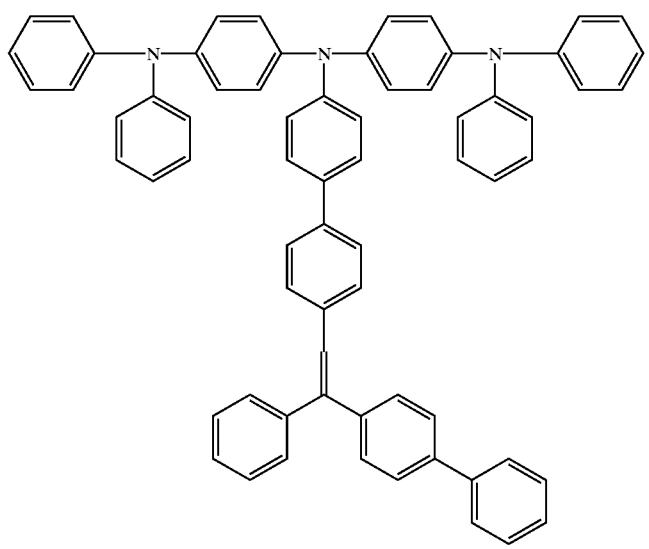
PT-29'
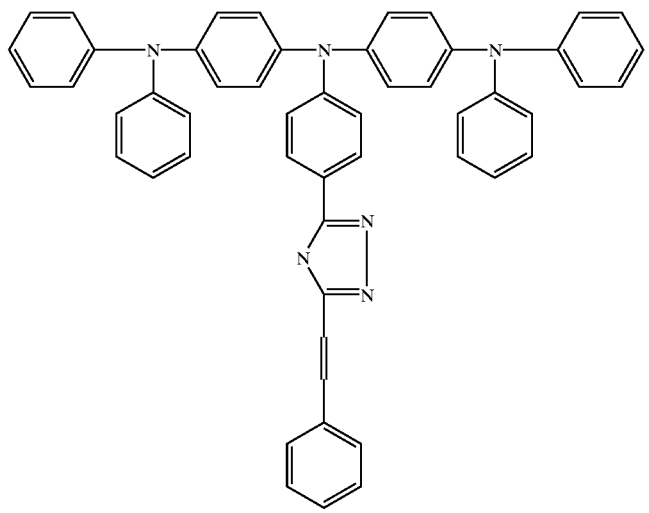
PT-30'
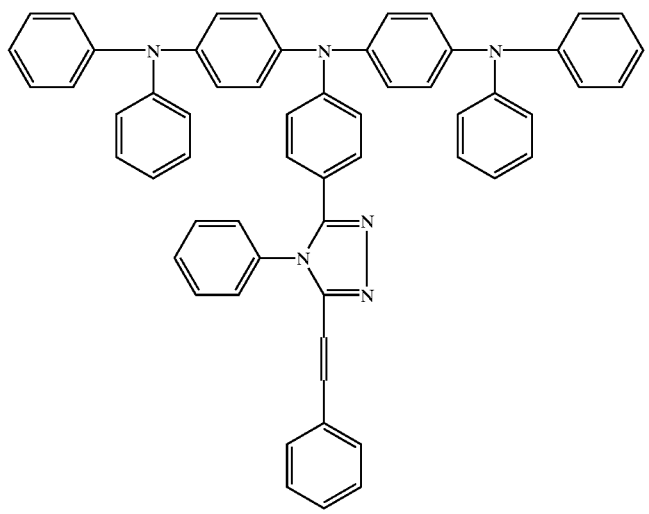
PT-31'
It has been found that the phenylenediamine derivatives represented by the general formula (IV) and the general formula (V) are particularly preferred. It has been found that because these compounds is not degraded with high fluorescent property upon electron injection, it can be used as a light emitting material, and further a long life time can be obtained as a hole injection layer and a hole transporting layer owing to the resistance to electron injection.

The effect of the invention will be described based on specific examples.

EXAMPLE 1

Synthesis of 4-Iodotriphenylamine 125 g of triphenylamine (produced by Hiroshima Wako & Co., Ltd.) was dissolved in 5 L of ethanol by heating, to which 150 g of mercury oxide was added at 60° C., and then 100 g of iodine was gradually added. Thereafter, the reaction was conducted for 2 hours at a reflux temperature.

After the reaction, the system was filtered under hot, and the residue was washed with acetone. The filtrate was cooled, and crystals thus deposited were filtered out.

It was purified by using a column carrying silica gel with toluene as a developing solvent, so as to obtain 52 g of objective substance.

Synthesis of PD-01

10 g of 4,4"-diamino-p-terphenylene (produced by Lancaster Synthesis, Ltd.), 20 g of 1-iodonaphthalene (produced by Hiroshima Wako & Co., Ltd.), 20 g of potassium carbonate, 1 g of copper powder and 100 ml of nitrobenzene were placed in a 300-ml three-neck flask, and were heated under stirring at 200° C. for 48 hours.

After the reaction, inorganic matters were filtered out, and the solvents in the mother liquid were distilled off. The residue was purified by using a column carrying silica gel (C-200 produced by Hiroshima Wako & Co., Ltd.) with toluene as a developing solvent, so as to obtain 8.4 g of 4,4"-bis(1-naphthylamino)-p-terphenylene.

5 g thereof, 15 g of 4-iodotriphenylamine, 20 g of potassium carbonate, 1 g of copper powder and 100 ml of nitrobenzene were placed in a 300-ml three-neck flask, and were heated at 200° C. for 60 hours.

After the reaction, inorganic matters were filtered out, and the solvents in the mother liquid were distilled off. The residue was purified by using a column carrying silica gel (C-200 produced by Hiroshima Wako & Co. Ltd.) with toluene/hexane=1/2 as a developing solvent. It was further purified by sublimation under vacuum of 0.01 mmHg, so as to obtain 0.8 g of pale yellow powder.

As a result of FD-MS, peaks of 999(M+1) and 499(1/2·M) were obtained with respect to $C_{74}H_{54}N_4=998$, and it was thus determined as PD-01.

EXAMPLE 2

Synthesis of PD-02

10 g of 9,10-diaminophenylanthracene (produced by Wakayama Seika Industries, Ltd.), 20 g of 1-iodonaphthalene (produced by Hiroshima Wako & Co., Ltd.), 20 g of potassium carbonate, 1 g of copper powder and 100 ml of nitrobenzene were placed in a 300-ml three-neck flask, and were heated under stirring at 200° C. for 48 hours.

After the reaction, inorganic matters were filtered out, and the solvents in the mother liquid were distilled off. The residue was purified by using a column carrying silica gel (C-200 produced by Hiroshima Wako & Co., Ltd.) with toluene as a developing solvent, so as to obtain 7.7 g of 9,10-bis(1-naphthylaminophenyl)anthracene.

5 g thereof, 15 g of 4-iodotriphenylamine, 20 g of potassium carbonate, 1 g of copper powder and 100 ml of nitrobenzene were placed in a 300-ml three-neck flask, and were heated at 200° C. for 60 hours.

After the reaction, inorganic matters were filtered out, and the solvents in the mother liquid were distilled off. The residue was purified by using a column carrying silica gel (C-200 produced by Hiroshima Wako & Co., Ltd.) with toluene/hexane=1/2 as a developing solvent. It was further purified by sublimation under vacuum of 0.01 mmHg, so as to obtain 0.8 g of pale yellow powder.

As a result of FD-MS, peaks of 1,099(M+1) and 549(1/2·M) were obtained with respect to $C_{82}H_{58}N_4=1,098$, and it was thus determined as PD-02

EXAMPLE 3

Synthesis of PD-03

10 g of 4,4'-diaminodiphenylmethane (produced by Hiroshima Wako & Co., Ltd.), 20 g of 1-iodonaphthalene (produced by Hiroshima Wako & Co., Ltd.), 20 g of potassium carbonate, 1 g of copper powder and 100 ml of nitrobenzene were placed in a 300-ml three-neck flask, and were heated under stirring at 200° C. for 48 hours.

After the reaction, inorganic matters were filtered out, and the solvents in the mother liquid were distilled off. The residue was purified by using a column carrying silica gel (C-200 produced by Hiroshima Wako & Co., Ltd.) with toluene as a developing solvent, so as to obtain 9.6 g of bis(4-(naphthyl-1-yl)aminophenyl)methane.

5 g thereof, 15 g of 4-iodotriphenylamine, 20 g of potassium carbonate, 1 g of copper powder and 100 ml of nitrobenzene were placed in a 300-ml three-neck flask, and were heated at 200° C. for 60 hours.

After the reaction, inorganic matters were filtered out, and the solvents in the mother liquid were distilled off. The residue was purified by using a column carrying silica gel (C-200 produced by Hiroshima Wako & Co., Ltd.) with toluene/hexane=1/2 as a developing solvent. It was further purified by sublimation under vacuum of 0.01 mmHg, so as to obtain 1.2 g of pale yellow powder.

As a result of FD-MS, peaks of 937(M+1) and 468(1/2·M) were obtained with respect to $C_{69}H_{52}N_4=936$, and it was thus determined as PD-03.

EXAMPLE 4

Synthesis of PD-04

10 g of 4,4'-diaminodiphenylether (produced by Hiroshima Wako & Co., Ltd.), 20 g of 1-iodonaphthalene (produced by Hiroshima Wako & Co., Ltd.), 20 g of potassium carbonate, 1 g of copper powder and 100 ml of nitrobenzene were placed in a 300-ml three-neck flask, and were heated under stirring at 200° C. for 48 hours.

After the reaction, inorganic matters were filtered out, and the solvents in the mother liquid were distilled off. The residue was purified by using a column carrying silica gel (C-200 produced by Hiroshima Wako & Co., Ltd.) with toluene as a developing solvent, so as to obtain 9.2 g of bis(4-(naphthyl-1-yl)aminophenyl)ether.

5 g thereof, 15 g of 4-iodotriphenylamine, 20 g of potassium carbonate, 1 g of copper powder and 100 ml of nitrobenzene were placed in a 300-ml three-neck flask, and were heated at 200° C. for 60 hours.

After the reaction, inorganic matters were filtered out, and the solvents in the mother liquid were distilled off. The residue was purified by using a column carrying silica gel (C-200 produced by Hiroshima Wako & Co., Ltd.) with toluene/hexane=1/2 as a developing solvent. It was further purified by sublimation under vacuum of 0.01 mmHg, so as to obtain 1.0 g of pale yellow powder.

As a result of FD-MS, peaks of 939(M+1) and 469(1/2·M) were obtained with respect to $C_{68}H_{50}N_4=938$, and it was thus determined as PD-04.

EXAMPLE 5

Synthesis of N-(1-Naphthyl)-4-iododiphenylamine 10 g of N-phenyl-N-(1-naphthyl)amine (produced by Hiroshima Wako & Co., Ltd.), 20 g of p-fluoronitrobenzene (produced by Hiroshima Wako & Co., Ltd.), 20 g of potassium carbonate, 1 g of copper powder and 100 ml of nitrobenzene were placed in a 300-ml three-neck flask, and were heated under stirring at 200° C. for 48 hours.

After the reaction, inorganic matters were filtered out, and the solvents in the mother liquid were distilled off. The residue was purified by using a column carrying silica gel (C-200 produced by Hiroshima Wako & Co., Ltd.) with toluene as a developing solvent, so as to obtain 9.0 g of N-naphthyl-4-nitrodiphenylamine.

It was placed in an autoclave, to which 100 ml of DMF and 5 g of 5% Pd/C were added, and hydrogen was charged to 5 Kg/cm$^2$, followed by stirring. After filtering the catalyst, 300 ml of a saturated common salt solution was charged therein, and crystals thus deposited were filtered. The crystals were recrystallized from toluene, so as to obtain 6.4 g of N-naphthyl-4-aminodiphenylamine.

20 ml of concentrated sulfuric acid was cooled to 15° C., to which 3 g of sodium nitrite was added at 30° C. or lower to be dissolved, and then 100 ml of acetic acid was added. 5.0 g of N-naphthyl-4-aminodiphenylamine was added thereto under cooling with ice, and then stirred at room temperature for 1 hour. Separately, 10 g of potassium iodide was dissolved in water at 70° C., and the reaction products were added thereto. After stirring at 70° C. for 30 minutes, it was then added into 1 L of water, followed by filtering insoluble matters. It was purified by using a column carrying silica gel (C-200 produced by Hiroshima Wako & Co., Ltd.) with toluene as a developing solvent, so as to obtain 2.7 g of N-(1-naphthyl)-4-iododiphenylamine.

Synthesis of PD-05

1 g of 9,10-bis(1-naphthylaminophenyl)anthracene synthesized in Example 2, 2 g of N-(1-naphthyl)-4-iododiphenylamine, 5 g of potassium carbonate, 1 g of copper powder and 100 ml of nitrobenzene were placed in a 300-ml three-neck flask, and were heated at 200° C. for 60 hours.

After the reaction, inorganic matters were filtered out, and the solvents in the mother liquid were distilled off. The residue was purified by using a column carrying silica gel (C-200 produced by Hiroshima Wako & Co., Ltd.) with toluene/hexane=1/2 as a developing solvent. It was further purified by sublimation under vacuum of 0.01 mmHg, so as to obtain 0.3 g of pale yellow powder.

As a result of FD-MS, peaks of 1,199(M+1) and 599(1/2·M) were obtained with respect to $C_{90}H_{62}N_4=1,198$, and it was thus determined as PD-05.

EXAMPLE 6

Synthesis of 4-Iodo-3'-methyltriphenylamine 3.4 g of 4-iodo-3'-methyltriphenylamine was obtained in the same manner as in Example 5 except that (3-methyl) diphenylamine (produced by Hiroshima Wako & Co., Ltd.) was used instead of N-phenyl(1-naphthyl)amine.

Synthesis of STBA-1

1 g of N,N'-diphenyl-4,4'-benzidine (produced by Tokyo Chemical Industry Co., Ltd.), 3 g of 4-iodo-3'-methyltriphenylamine, 5 g of potassium carbonate, 1 g of copper powder and 100 ml of nitrobenzene were placed in a 300-ml three-neck flask, and were heated at 200° C. for 60 hours.

After the reaction, inorganic matters were filtered out, and the solvents in the mother liquid were distilled off. The residue was purified by using a column carrying silica gel (C-200 produced by Hiroshima Wako & Co., Ltd.) with toluene/hexane=1/2 as a developing solvent. It was further purified by sublimation under vacuum of 0.01 mmHg, so as to obtain 0.2 g of pale yellow powder.

As a result of FD-MS, peaks of 823(M+1) and 411(1/2·M) were obtained with respect to $C_{60}H_{46}N_4=822$, and it was thus determined as STBA-1. The fluorescent spectrum of STBA-1 is shown in FIG. 1.

EXAMPLE 7

Synthesis of 4-Iodo-4'-nitrobiphenyl 1,500 g of biphenyl (produced by Hiroshima Wako & Co., Ltd.), 444 g of orthoperiodic acid (produced by Hiroshima Wako & Co., Ltd.), 987 g of iodine, 5.1 kg of acetic acid, 147 ml of sulfuric acid and 975 g of water were placed in a 10-L flask, and heated under stirring at 70° C. for 2 hours.

After the reaction, 1.3 kg of water was added thereto, and crystals thus deposited were filtered. The crystals were recrystallized from 5.5 kg of ethanol to obtain 2,010 g of crystals.

The crystals were dissolved in 14 kg of acetic acid, and 1.8 L of fuming nitric acid was added dropwise at 80° C., followed by stirring for 8 hours. After cooling to room temperature, 9.5 kg of methanol was added, and crystals thus deposited were filtered, which was then recrystallized from 27 kg of toluene, so as to obtain 580 g of 4-iodo-4'-nitrobiphenyl. cl Synthesis of PT-01

2 kg of diphenylamine (produced by Hiroshima Wako & Co., Ltd.), 500 g of 4-iodo-4'-nitrobiphenyl, 500 g of anhydrous potassium carbonate, 20 g of copper powder and 2 L of nitrobenzene were placed in a 10-L flask, and were heated under stirring at 200° C. for 15 hours.

In After the reaction, inorganic matters were filtered out, and the solvents in the mother liquid were distilled off. The residue was purified by using a column carrying silica gel (C-200 produced by Hiroshima Wako & Co., Ltd.) with toluene as a developing solvent, so as to obtain 340 g of crystals.

The crystals were dissolved in 7 L of DMF, which was placed in a 10-L autoclave along with 30 g of 5% Pd/C. Hydrogen was charged to 25 Kg/cm$^2$, and the temperature was increased to 50° C., followed by stirring for 8 hours with maintaining at 10 to 25 kg/cm$^2$. After filtering the catalyst, the filtrate was put into water, and the deposited matters were filtered, which was then recrystallized from 40 L of tolaene to obtain 283 g of crystals.

250 g of the crystals, 280 g of p-fluoronitrobenzene (produced by Hiroshima Wako & Co., Ltd.), 500 g of anhydrous potassium carbonate, 10 g of copper powder and 1 L of nitrobenzene were placed in a 5-L flask, and were heated under stirring at 200° C. for 32 hours.

After the reaction, inorganic matters were filtered out, and the solvents in the mother liquid were distilled off. The residue was purified by using a column carrying silica gel (C-200 produced by Hiroshima Wako & Co., Ltd.) with toluene as a developing solvent, so as to obtain 194 g of crystals.

The crystals were dissolved in 4 L of DMF, which was placed in a 10-L autoclave along with 30 g of 5% Pd/C. Hydrogen was charged to 25 Kg/cm$^2$, and the temperature was increased to 50° C., followed by stirring for 8 hours with maintaining at 10 to 25 kg/cm$^2$. After filtering the catalyst, the filtrate was put into water, and the deposited matters were filtered, which was then recrystallized from 20 L of toluene to obtain 128 g of crystals.

100 g of the crystals, 200 g of iodobenzene (produced by Hiroshima Wako & Co., Ltd.), 250 g of anhydrous potassium carbonate, 5 g of copper powder and 1 L of nitrobenzene were placed in a 5-L flask, and were heated under stirring at 200° C. for 48 hours.

After the reaction, inorganic matters were filtered out, and the solvents in the mother liquid were distilled off. The of 400 Å. The vapor deposition rate of DPVTP was 50 Å/sec, and the vapor deposition rate of DPAVBi was 1 Å/sec.

Furthermore, Alq was vapor-deposited at a vapor deposition rate of 2 Å/sec. Finally, aluminum and lithium were simultaneously vapor-deposited to form a cathode having a thickness of 2,000 Å. The vapor deposition rate of aluminum was 10 Å/sec, and the vapor deposition rate of lithium was 0.1 Å/sec.

When the resulting device was subjected to light emission of 1,000 nit, the driving voltage was 6.2 V. The voltage increase after driving at a constant current for 100 hours was 0.4 V, the driving voltage increase after 1,000 hours was 0.6 V, and the half life time was 600 hours. The ionization energy of DPVTP is 5.9 eV, and the ionization energy of DPAVBi is 5.5 eV.

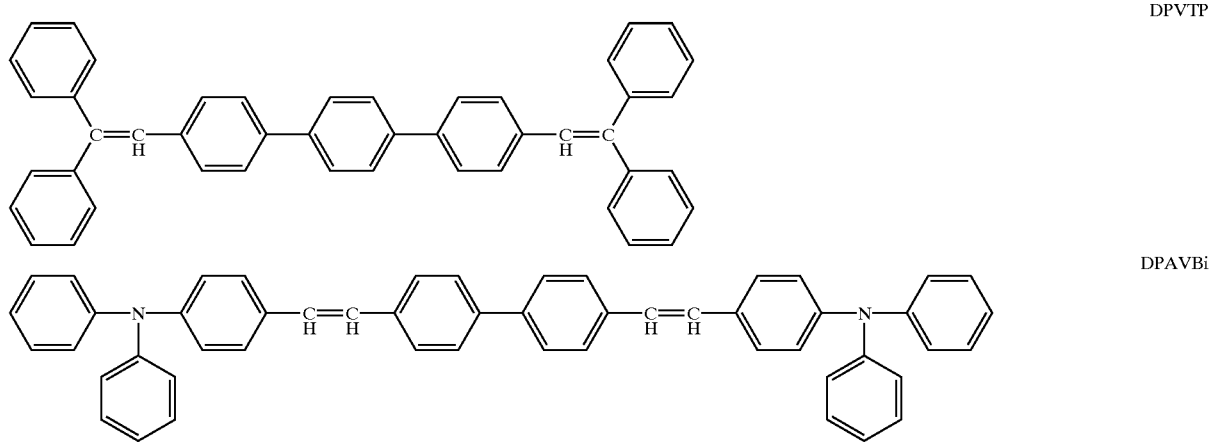

residue was purified by using a column carrying silica gel (C-200 produced by Hiroshima Wako & Co., Ltd.) with toluene/hexane=1/2 as a developing solvent. It was further purified by sublimation under vacuum of 0.01 mmHg, so as to obtain 23 g of pale yellow powder.

As a result of FD-MS, peaks of 823(M+1) and 411(1/2·M) were obtained with respect to $C_{60}H_{46}N_4$=822, and it was thus determined as PT-01.

EXAMPLE 8

An organic EL device was produced by using PD-1 described in the foregoing.

A transparent anode of indium tin oxide was provided by coating on glass. The indium tin oxide had a thickness of about 750 Å, and the glass has a size of 25 mm×75 mm×1.1 mm.

This was placed in a vacuum vapor deposition apparatus (produced by ULVAC Japan, Ltd.) and the pressure was reduced to about 10$^{-6}$ torr. PD-01 was vapor-deposited thereon to a thickness of 600 Å. The vapor deposition rate herein was 2 Å/sec.

NPD was then vapor-deposited to a thickness of 200 Å. The vapor deposition rate herein was 2 Å/sec.

DPVTP as a light emitting material and DPAVBi as an carrier injection auxiliary were simultaneously vapor-deposited to form a light emitting layer having a thickness

EXAMPLE 9

An organic EL device was produced in the same manner as in Example 8 except that PD-02 was used instead of PD-01.

When the resulting device was subjected to light emission of 1,000 nit, the driving voltage was 6.0 V. The voltage increase after driving at a constant current for 100 hours was 0.5 V, the driving voltage increase after 1,000 hours was 0.7 V, and the half life time was 2,000 hours.

EXAMPLE 10

An organic EL device was produced in the same manner as in Example 8 except that PD-03 was used instead of PD-01.

When the resulting device was subjected to light emission of 1,000 nit, the driving voltage was 6.3 V. The voltage increase after driving at a constant current for 100 hours was 0.4 V, and the driving voltage increase after 1,000 hours was 0.6 V.

EXAMPLE 11

An organic EL device was produced in the same manner as in Example 8 except that PD-04 was used instead of PD-01.

When the resulting device was subjected to light emission of 1,000 nit, the driving voltage was 6.2 V. The voltage increase after driving at a constant current for 100 hours was 0.4 V, and the driving voltage increase after 1,000 hours was 0.7 V.

EXAMPLE 12

An organic EL device was produced in the same manner as in Example 8 except that PD-05 was used instead of PD-01.

When the resulting device was subjected to light emission of 1,000 nit, the driving voltage was 6.1 V. The voltage increase after driving at a constant current for 100 hours was 0.5 V, the driving voltage increase after 1,000 hours was 0.6 V, and the half life time was 2,100 hours.

EXAMPLE 13

An organic EL device was produced in the same manner as in Example 8 except that STBA-1 was used instead of PD-01.

When the resulting device was subjected to light emission of 1,000 nit, the driving voltage was 6.1 V. The voltage increase after driving at a constant current for 100 hours was 0.4 V, the driving voltage increase after 1,000 hours was 0.6 V, and the half life time was 1,200 hours.

As described herein, the compound (III) of the invention exhibited a particularly low driving voltage, a small voltage increase, and a long half life time. The results indicate that the compound (III) of the invention has the excellent characteristics described in the foregoing in comparison to STBA-1.

EXAMPLE 14

A glass substrate having an ITO coating (produced by Asahi Glass Company, 15 ohm per square, 1,500 Å) was cut into 25 mm×25 mm, and a clear tape (width: 12 mm) produced by Scotch Corp. was adhered on the center of the side of the ITO without biting air bubbles. The substrate was immersed in a corrosive liquid to form a pattern.

This was placed in a vacuum vapor deposition apparatus (produced by ULVAC Japan, Ltd.) and the pressure was reduced to about $10^{-6}$ torr. STBA-1 was vapor-deposited thereon to a thickness of 500 Å. The vapor deposition rate herein was 2 Å/sec.

Alq was then vapor-deposited to a thickness of 500 Å at a vapor deposition rate of 2 Å/sec.

Finally, magnesium and silver were simultaneously vapor-deposited to form a cathode having a thickness of 2,000 Å. The vapor deposition rate of magnesium was 10 Å/sec, and the vapor deposition rate of silver was 1 Å/sec.

Furthermore, silver was accumulated by vapor deposition to 1,000 Å as an oxidation protective film. The area of the electrode was 5 mm×5 mm.

When the resulting device was subjected to light emission of 100 nit, the driving voltage was 4.8 V.

The voltage increase after driving at a constant current for 100 hours was 0.8 V, and the driving voltage increase after 1,000 hours was 1.3 V.

EXAMPLE 15

An organic EL device was produced in the same manner as in Example 8 except that PT-01 was used instead of PD-01.

When the resulting device was subjected to light emission of 1,000 nit, the driving voltage was 6.2 V. The voltage increase after driving at a constant current for 100 hours was 0.3 V, and the driving voltage increase after 1,000 hours was 0.5 V.

EXAMPLE 16

An organic EL device was produced in the same manner as in Example 8. However, STBA-1 was used instead of PD-01, and as a blue color light emitting material, DPA2 shown by the following chemical formula disclosed in International Patent Publication WO98/30071 (published on Jul. 9, 1998) was used instead of DPVTP. DPAVBi was added as a charge injection auxiliary.

In this case, when the resulting device was subjected to light emission of 1,000 nit, the driving voltage was 6.3 V. The voltage increase after driving at a constant current for 100 hours was 0.4 V, the driving voltage increase after 1,000 hours was 0.7 V, and the half life time was 1,200 hours.

As comparing an organic EL device in Comparative Example 4 described later, to which no charge injection auxiliary, DPAVBi, was added, to the organic EL device of this example, because in the organic EL device of the invention, the charge injection auxiliary was added to the light emitting material, and the compound represented by the general formula (I) was used in the hole transporting zone, such characteristics were obtained in that it could be driven at a low voltage with a low voltage increase after the constant current driving, and the life time was long.

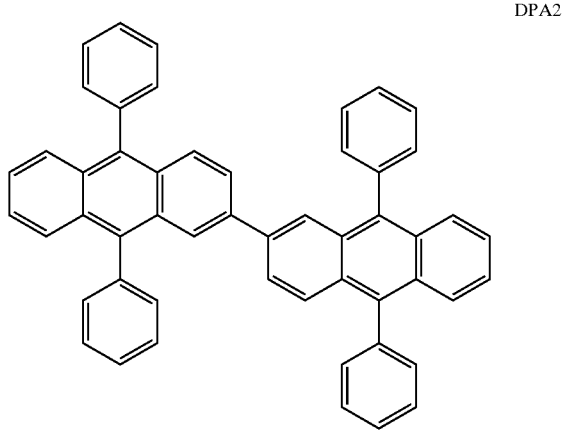

DPA2

EXAMPLE 17

This example is a use example as a light emitting material. PD-05' was vapor-deposited to a thickness of 800 Å on glass having indium tin oxide coated thereon. Aluminum and lithium were then simultaneously vapor-deposited to form a cathode comprising an aluminum-lithium alloy containing 3 wt % of lithium.

When a voltage of 6.0 V was applied on the resulting light emitting device, a light emission luminance of 400 nit was obtained. The half life time was 300 hours.

EXAMPLE 18

A light emitting device was produced in the same manner as in Example 17 except that PD-35' was used instead of PD-05'.

When a voltage of 5.5 V was applied on the resulting light emitting device, a light emission luminance of 400 nit was obtained. The half life time was 340 hours.

EXAMPLE 19

A light emitting device was produced in the same manner as in Example 17 except that PD-36' was used instead of PD-05'.

When a voltage of 7.0 V was applied on the resulting light emitting device, a light emission luminance of 350 nit was obtained. The half life time was 250 hours.

EXAMPLE 20

A light emitting device was produced in the same manner as in Example 17 except that PD-38' was used instead of PD-05'.

When a voltage of 6.2 V was applied on the resulting light emitting device, a light emission luminance of 280 nit was obtained. The half life time was 400 hours.

EXAMPLE 21

A light emitting device was produced in the same manner as in Example 17 except that PD-44' was used instead of PD-05'.

When a voltage of 8.0 V was applied on the resulting light emitting device, a light emission luminance of 440 nit was obtained. The half life time was 460 hours.

EXAMPLE 22

A light emitting device was produced in the same manner as in Example 17 except that PD-49' was used instead of PD-05'.

When a voltage of 4.7 V was applied on the resulting light emitting device, a light emission luminance of 380 nit was obtained. The half life time was 340 hours.

EXAMPLE 23

A light emitting device was produced in the same manner as in Example 17 except that PD-54' was used instead of PD-05'.

When a voltage of 6.2 V was applied on the resulting light emitting device, a light emission luminance of 250 nit was obtained. The half life time was 280 hours.

EXAMPLE 24

A light emitting device was produced in the same manner as in Example 17 except that PT-01' was used instead of PD-05'.

When a voltage of 5.3 V was applied on the resulting light emitting device, a light emission luminance of 450 nit was obtained. The half life time was 400 hours.

EXAMPLE 25

A light emitting device was produced in the same manner as in Example 17 except that PT-04' was used instead of PD-05'.

When a voltage of 5.6 V was applied on the resulting light emitting device, a light emission luminance of 280 nit was obtained. The half life time was 320 hours.

EXAMPLE 26

A light emitting device was produced in the same manner as in Example 17 except that PT-08' was used instead of PD-05'.

When a voltage of 4.8 V was applied on the resulting light emitting device, a light emission luminance of 340 nit was obtained. The half life time was 250 hours.

EXAMPLE 27

A light emitting device was produced in the same manner as in Example 17 except that PT-10' was used instead of PD-05'.

When a voltage of 5.7 V was applied on the resulting light emitting device, a light emission luminance of 300 nit was obtained. The half life time was 280 hours.

EXAMPLE 28

A light emitting device was produced in the same manner as in Example 17 except that PT-25' was used instead of PD-05'.

When a voltage of 6.2 V was applied on the resulting light emitting device, a light emission luminance of 320 nit was obtained. The half life time was 360 hours.

COMPARATIVE EXAMPLE 1

An organic EL device was produced in the same manner as in Example 8 except that NPDATA was used instead of PD-01.

When the resulting device was subjected to light emission of 1,000 nit, the driving voltage was 8.4 V. The voltage increase after driving at a constant current for 100 hours was 0.5 V, and the driving voltage increase after 1,000 hours was 0.7 V.

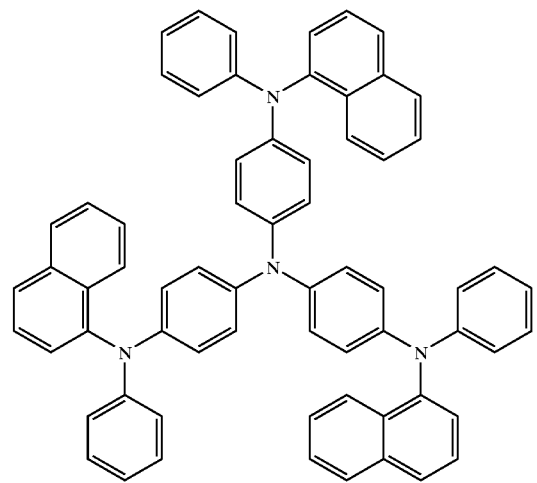

NPDATA

COMPARATIVE EXAMPLE 2

An organic EL device was produced in the same manner as in Example 8 except that NPD was used instead of PD-01.

When the resulting device was subjected to light emission of 1,000 nit, the driving voltage was 11.8 V. The voltage increase after driving at a constant current for 100 hours was 1.4 V, and the driving voltage increase after 1,000 hours was 3.8 V.

COMPARATIVE EXAMPLE 3

An organic EL device was produced in the same manner as in Example 8 except that HI-01 was used instead of PD-01.

When the resulting device was subjected to light emission of 1,000 nit, the driving voltage was 8.1 V. The voltage increase after driving at a constant current for 100 hours was 0.5 V, and the driving voltage increase after 1,000 hours was 0.8 V..

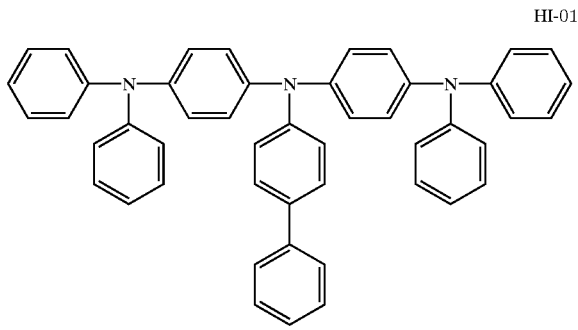

HI-01

COMPARATIVE EXAMPLE 4

An organic EL device was produced in the same manner as in Example 16, provided that the charge injection auxiliary, DPAVBi, was not added.

In this case, when resulting device was subjected to light emission of 1,000 nit, the driving voltage was 7.0 V. The voltage increase after driving at a constant current for 100 hours was 1.2 V, and the driving voltage-increase after 1,000 hours was 2.0 V. The half life time herein was 800 hours.

COMPARATIVE EXAMPLE 5

A light emitting device was produced in the same manner as in Example 17 except that STBA-1 was used instead of PD-05'.

When a voltage of 9.4 V was applied on the resulting light emitting device, a light emission luminance of 170 nit was obtained. The half life time was 20 hours.

It was found from the comparison between the results obtained in the light emitting device of Comparative Example 5 and the results obtained in the light emitting devices of Example 18 to Example 23 that in the case where STBA-1 was used, it had an extremely short life time as a light emitting material. This is because the material is degraded upon injection of an electron into STBA-1.

However, the compound represented by the general formula (III) of the invention has a long half life time and is difficult to be degraded on electron injection.

Therefore, because a small amount of electrons are injected even in the hole transporting zone, it is preferred that the compound represented by the general formula (III) having resistance to electron injection is used in the hole transporting zone.

COMPARATIVE EXAMPLE 6

A light emitting device was produced in the same manner as in Example 17 except that PT-01 was used instead of PD-05'.

When a voltage of 8.9 V was applied on the resulting light emitting device, a light emission luminance of 120 nit was obtained. The half life time was 30 hours.

It was found from the comparison between the result obtained in the light emitting device of Comparative Example 6 and the results obtained in the light emitting devices of Example 24 to Example 28 that while the compound shown by PT-01 exhibited no resistance to electron injection, the compounds represented by the general formula (IV) and the general formula (V) other than PT-01 exhibited resistance to electron injection. However, in the case where PT-01 is used in the hole transporting zone as in the embodiment described above, no problem arises since the electron injection amount is small and substantially no degrading occur. Furthermore, when the compounds represented by the general formulae (III), (IV) and (V) having high resistance to electron injection are used, the life time of the light emitting device itself can be prolonged.

It was understood from the foregoing results that by using the compound of the invention in the hole transporting zone, the production of a long-life organic EL device having an extremely reduced voltage required for exhibiting constant light emission could be realized.

As a result of purification to avoid impurities, the voltage increase on driving became extremely small.

INDUSTRIAL UTILITY FIELD

As described in the foregoing, according to the invention, a phenylenediamine derivative having a small ionization potential and a large hole mobility can be obtained. When the phenylenediamine derivative is contained in the hole transporting layer in the organic light emitting layer between a pair of electrodes, and the organic light emitting layer of the organic EL device is formed with addition of a charge injection auxiliary, decrease in driving voltage and prolongation of the life time of the device are realized.

What is claimed is:
1. A phenylenediamine derivative represented by the general formula (III)

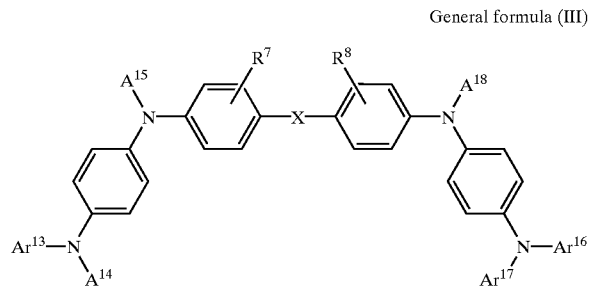

General formula (III)

wherein $Ar^{13}$ to $Ar^{18}$ represent an aryl group having from 6 to 24 nucleus carbon atoms, which may be substituted with a hydrogen atom, an alkyl or an alkoxy group having from 1 to 6 carbon atom(s), an aryl group having from 6 to 24 nucleus carbon atoms, or a styryl group; X represents a linking group, which is a single bond, arylene having from 6 to 24 nucleus carbon atoms, alkylene having from 1 to 6 carbon atom(s), diphenylmethylene, an ether bond, a thioether bond, a substituted or unsubstituted vinyl bond, or an aromatic heterocyclic ring; $R^7$ and $R^8$ represent an alkyl group having from 1 to 6 carbon atom(s), an alkoxy group, or a hydrogen atom, which may be bonded to each other to form a substituted or unsubstituted saturated 5-membered ring or a saturated 6-membered ring, provided that at least one of $Ar^{13}$ to $Ar^{16}$ and X represents an aryl group containing a styryl group; or one of $Ar^{15}$, $Ar^{18}$ and a basic skeleton shown by the following chemical formula (1) contains a condensed aromatic ring, an aromatic heterocyclic ring or a substituted or unsubstituted vinyl group;

general formula (1)

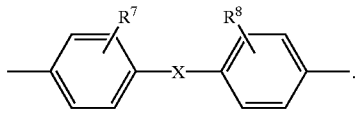

2. A phenylenediamine derivative represented by the general formula (III) according to claim 1, wherein $Ar^{13}$ to $Ar^{18}$ represent an aryl group having from 6 to 24 nucleus carbon atoms, which may be substituted with an alkyl or an alkoxy group having from 1 to 6 carbon atom(s), an aryl group having from 6 to 24 nucleus carbon atoms, or a styryl, group, X reprsents a linking group, which is a single bond, arylene having from 6 to 24 nucleus carbon atoms, alkylene having from 1 to 6 carbon atom(s), diphenylmethylene, an ether bond, a thioether bond, a substituted or unsubstituted vinyl bond, or an aromatic heterocyclic ring; $R^7$ and $R^8$ represent an alkyl group having from 1 to 6 carbon atom(s), an alkoxy group, or a hydrogen atom, which may be bonded to each other to form a substituted or unsubstituted saturated 5-membered ring or a saturated 6-membered ring, provided that one of $Ar^{15}$, $Ar^{18}$ and a basic skeleton shown by the following chemical formula (1) is a naphthyl group, an anthranyl group, a pyrenyl group or phenoanthryl group;

general formula (1)

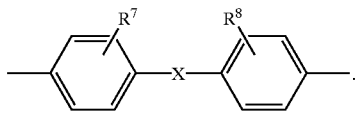

3. A phenylenediamine derivative represented by the general formula (III) according to claim 1, wherein $Ar^{13}$ to $Ar^{18}$ represent an aryl group having from 6 to 24 nucleus carbon atoms, which may be substituted with an aryl group having from 6 to 24 nucleus carbon atoms; X represents a linking group, which is a single bond, arylene having from 6 to 24 nucleus carbon atoms, alkylene having from 1 to 6 carbon atom(s), or an aromatic heterocyclic ring; $R^7$ and $R^8$ represent an alkyl group having from 1 to 6 carbon atom(s), an alkoxy group, or a hydrogen atom, which may be bonded to each other to form a substituted or unsubstituted saturated 5-membered ring or a saturated 6-membered ring, provided that one of $Ar^{15}$, $Ar^{18}$ and a basic skeleton shown by the following chemical formula(1) contains a condensed aromatic ring, an aromatic heterocyclic ring or a substituted or unsubstituted vinyl group;

general formula (1)

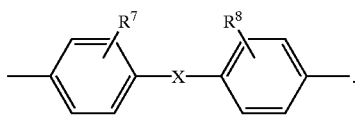

4. A phenylenediamine derivative represented by the general formula (III) according to claim 1, wherein $Ar^{13}$ to $Ar^{18}$ represent an aryl group having from 6 to 24 nucleus carbon atoms, which may be substituted with an aryl group having from 6 to 24 nucleus carbon atoms; X represents a linking group, which is a single bond or arylene group having from 6 to 24 nucleus carbon atoms; $R^7$ and $R^8$ represent a hydrogen atom, provided that $Ar^{15}$ and $Ar^{18}$ are a naphthyl group.

5. A phenylenediamine derivative of claim 1, of the formula:

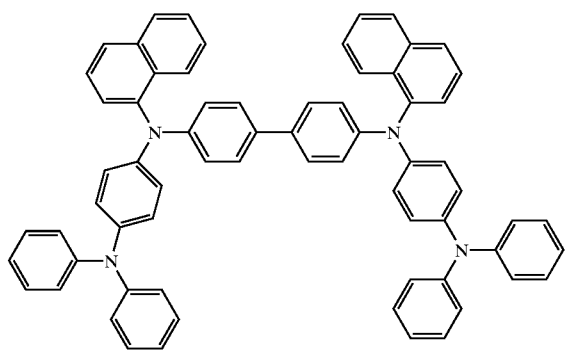

6. An organic electroluminescence device comprising a pair of electrodes and an organic light emitting layer or zone sandwiched in said electrodes, characterized in that a hole transporting layer or, zone provided between said electrodes comprises a phenylenediamine derivative represented by the general formula (III), as defined in claim 1.

7. An organic electroluminescence device according to claim 6, wherein the phenylenediamine derivative is of the formula

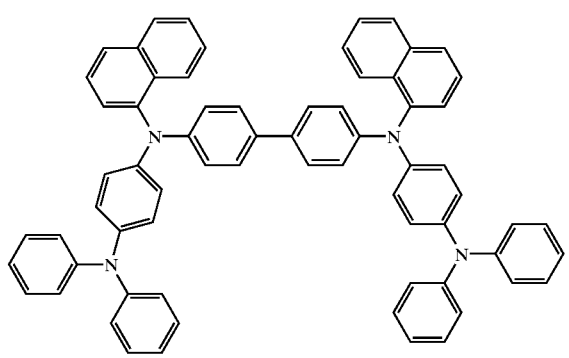

8. An organic electroluminescence device comprising a pair of electrodes and an organic light emitting layer or zone sandwiched in said electrodes, characterized in that a hole transporting layer or zone provided between said electrodes comprises a phenylenediamine derivative of the formula (I):

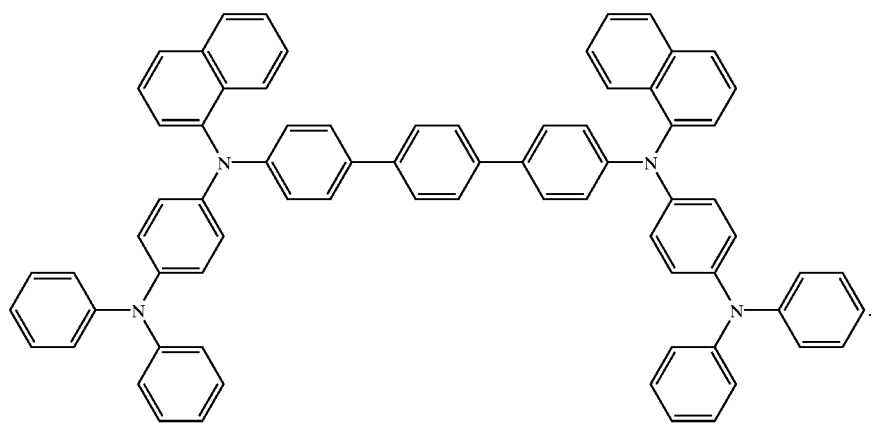
* * * * *